United States Patent
Ju et al.

(10) Patent No.: US 7,345,159 B2
(45) Date of Patent: Mar. 18, 2008

(54) MASSIVE PARALLEL METHOD FOR DECODING DNA AND RNA

(75) Inventors: Jingyue Ju, Englewood Cliffs, NJ (US); Zengmin Li, New York, NY (US); John Robert Edwards, New York, NY (US); Yasuhiro Itagaki, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 399 days.

(21) Appl. No.: 10/702,203

(22) Filed: Nov. 6, 2003

(65) Prior Publication Data

US 2004/0185466 A1 Sep. 23, 2004

Related U.S. Application Data

(60) Division of application No. 09/972,364, filed on Oct. 5, 2001, now Pat. No. 6,664,079, which is a continuation-in-part of application No. 09/684,670, filed on Oct. 6, 2000, now abandoned.

(60) Provisional application No. 60/300,894, filed on Jun. 26, 2001.

(51) Int. Cl.
*C07H 21/00* (2006.01)
*C07H 21/02* (2006.01)
*C07H 21/04* (2006.01)
*C12Q 1/68* (2006.01)

(52) U.S. Cl. .................. 536/23.1; 536/25.3; 536/26.6; 435/6

(58) Field of Classification Search ............... 536/23.1, 536/25.3, 26.6; 435/6
See application file for complete search history.

(56) References Cited

U.S. PATENT DOCUMENTS

| 4,711,955 A | 12/1987 | Ward et al. |
| 4,824,775 A | 4/1989 | Dattagupta |
| 5,118,605 A | 6/1992 | Udrea |
| 5,174,962 A | 12/1992 | Brennan |
| 5,302,509 A | 4/1994 | Cheeseman |

(Continued)

FOREIGN PATENT DOCUMENTS

EP 0992511 4/2000

(Continued)

OTHER PUBLICATIONS

Axelrod, V. D. et al. (1978) Specific termination of RNA polymerase synthesis as a method of RNA and DNA sequencing Nucleic Acids Res. 5(10):3549-3563.

(Continued)

*Primary Examiner*—Jezia Riley
(74) *Attorney, Agent, or Firm*—John P. White; Cooper & Dunham LLP

(57) ABSTRACT

This invention provides methods for attaching a nucleic acid to a solid surface and for sequencing nucleic acid by detecting the identity of each nucleotide analogue after the nucleotide analogue is incorporated into a growing strand of DNA in a polymerase reaction. The invention also provides nucleotide analogues which comprise unique labels attached to the nucleotide analogue through a cleavable linker, and a cleavable chemical group to cap the —OH group at the 3'-position of the deoxyribose.

18 Claims, 28 Drawing Sheets

U.S. PATENT DOCUMENTS

| | | | |
|---|---|---|---|
| 5,599,675 | A | 2/1997 | Brenner |
| 5,654,419 | A | 8/1997 | Mathies |
| 5,728,528 | A | 3/1998 | Mathies |
| 5,763,594 | A | 6/1998 | Hiatt et al. |
| 5,770,367 | A | 6/1998 | Southern |
| 5,789,167 | A | 8/1998 | Konrad et al. |
| 5,804,386 | A | 9/1998 | Ju |
| 5,808,045 | A | 9/1998 | Hiatt et al. |
| 5,814,454 | A | 9/1998 | Ju |
| 5,834,203 | A | 11/1998 | Katzir |
| 5,849,542 | A | 12/1998 | Reeve et al. |
| 5,853,992 | A | 12/1998 | Glazer |
| 5,869,255 | A | 2/1999 | Mathies |
| 5,872,244 | A | 2/1999 | Hiatt et al. |
| 5,876,036 | A | 3/1999 | Mathis |
| 5,885,775 | A | 3/1999 | Haff et al. |
| 5,945,283 | A | 8/1999 | Kwok |
| 5,952,180 | A | 9/1999 | Ju |
| 6,028,190 | A | 2/2000 | Mathies |
| 6,046,005 | A | 4/2000 | Ju |
| 6,074,823 | A | 6/2000 | Koster |
| 6,136,543 | A * | 10/2000 | Anazawa et al. ............ 435/6 |
| 6,197,557 | B1 | 3/2001 | Makarov et al. |
| 6,214,987 | B1 | 4/2001 | Hiatt et al. |
| 6,218,118 | B1 | 4/2001 | Sampson |
| 6,218,530 | B1 | 4/2001 | Rothschild et al. |
| 6,232,465 | B1 | 5/2001 | Hiatt et al. |
| 6,312,893 | B1 | 11/2001 | Van Ness et al. |
| 6,316,230 | B1 | 11/2001 | Egholm |
| 6,361,940 | B1 | 3/2002 | Van Ness et al. |
| 6,613,508 | B1 | 9/2003 | Ness et al. |
| 6,627,748 | B1 | 9/2003 | Ju et al. |
| 6,664,079 | B2 | 12/2003 | Ju et al. |
| 6,664,399 | B1 | 12/2003 | Sabesan |
| 6,787,308 | B2 | 9/2004 | Balasubramanian et al. |
| 6,833,246 | B2 | 12/2004 | Balasubramanian |
| 7,057,026 | B2 | 6/2006 | Barnes et al. |
| 7,074,597 | B2 | 7/2006 | Ju |
| 2002/0168642 | A1 | 11/2002 | Drukier |
| 2003/0008285 | A1 | 1/2003 | Fischer |
| 2003/0022225 | A1 | 1/2003 | Monforte et al. |
| 2003/0027140 | A1 | 2/2003 | Ju et al. |
| 2003/0044781 | A1 | 3/2003 | Korlach |
| 2003/0044871 | A1 | 3/2003 | Cutsforth et al. |
| 2003/0099972 | A1 | 5/2003 | Olejnik et al. |
| 2004/0185466 | A1 | 9/2004 | Ju et al. |
| 2005/0032081 | A1 | 2/2005 | Ju et al. |
| 2006/0003352 | A1 | 1/2006 | Lipkin et al. |
| 2006/0057565 | A1 | 3/2006 | Ju et al. |
| 2006/0252038 | A1 | 11/2006 | Ju et al. |

FOREIGN PATENT DOCUMENTS

| | | |
|---|---|---|
| WO | WO 9106678 | 5/1991 |
| WO | WO 92/10587 | 6/1992 |
| WO | WO 00/53805 | 9/2000 |
| WO | WO 0053805 | 9/2000 |
| WO | WO 01/27625 | 4/2001 |
| WO | WO 0192284 | 12/2001 |
| WO | WO0222883 | 3/2002 |
| WO | WO0229003 | 4/2002 |
| WO | WO02079519 | 10/2002 |
| WO | WO 2004/007773 | 1/2004 |
| WO | WO 2004/055160 | 1/2004 |
| WO | WO 2004/018492 | 3/2004 |
| WO | WO 2004/018497 | 3/2004 |
| WO | WO 2005/084367 | 9/2005 |
| WO | WO 2006/073436 | 7/2006 |
| WO | WO 2007/002204 | 1/2007 |

OTHER PUBLICATIONS

Badman, E. R. et al. (2000) A Parallel Miniature Cylindrical Ion Trap Array. *Anal. Chem.* 72:3291-3297.

Badman, E. R. et al. (2000) Cylindrical Ion Trap Array with Mass Selection by Variation in Trap Dimensions. *Anal. Chem.* 72:5079-5086.

Benson, S. C., Mathies, R. A. and Glazer, A. N. (1993) Heterodimeric DNA-binding dyes designed for energy transfer: stability and applications of the DNA complexes. *Nucleic Acids Res.* 21:5720-5726.

Benson, S. C., Singh, P. and Glazer, A. N. (1993) HeterodimericDNA-binding dyes designed for energy transfer: synthesis and spectroscopic properites. *Nucleic Acids Res.* 21:5727-5735.

Burgess, K. et al. (1997) Photolytic Mass Laddering for Fast Characterization of Oligomers on Single Resin Beads. *J. Org. Chem.* 62:5662-5663.

Conard, B. et al. (1995) Catalytic editing properties of DNA polymerases. *Proc. Natl. Acad. Sci.* USA 92:10859-10863.

Caruthers, M. H. (1985) Gene synthesis machines: DNA chemistry and its uses. *Science* 230:281-285.

Chee, M. et al. (1996) Accessing genetic information with high-density DNA arrays. *Science* 274:610-614.

Chen, X. and Kwok, P.-Y. (1997) Template-directed dye-terminator incorporation (TDI) assay: a homogeneous DNA diagnostic method based on fluorescence resonance energy transfer. *Nucleic Acids Res.* 25:347-353.

Edwards, J. et al. (2001) DNA sequencing using biotinylated dideoxynucleotides and mass spectrometry. *Nucleic Acids Res.* 29 (21) :e104.

Griffin, T. J. et al. (1999) Direct Genetic Analysis by Matrix-Assisted Laser Desorption/Ionization Mass Spectrometry. *Proc. Nat. Acad. Sci.* USA 96:6301-6306.

Hacia, J. G., Edgemon, K., Sun, B., Stern, D., Fodor, S. A.,and Collins, F.S. (1998) Two Color Hybridization Analysis Using High Density Oligonucleotide Arrays and Energy Transfer Dyes. *Nucleic Acids Res.* 26:3865-6.

Haff, L. A. et al. (1997) Multiplex Genotyping of PCR Products with Mass Tag-Labeled Primers. *Nucleic Acids Res.* 25(18) :3749-3750.

Hyman, E. D. (1988) A new method of sequencing DNA. *Analytical Biochemistry* 174:423-436.

Ireland, R. E. and Varney M. D. (1986) Approach to the total synthesis of chlorothricolide—synthesis of (+/−)-19.20-dihydro-24-O-methylchlorothricolide, methyl-ester,ethyl carbonate. *J. Org. Chem.* 51: 635-648.

Jiang-Baucom, P. et al. (1997) DNA Typing of Human Leukocyte Antigen Sequence Polymorphisms by Peptide Nucleic Acid Probes and MALDI-TOF Mass Spectrometry. *Anal. Chem.* 69:4894-4896.

Ju, J., Glazer, A. N. and Mathies, R. A. (1996) Energy transfer primers: A new fluorescence labeling paradigm for DNA sequencing and analysis. *Nature Medicine* 2:246-249.

Ju, J., Ruan, C., Fuller, C. W., Glazer, A. N. and Mathies, R. A. (1995) Fluorescence energy transfer dye-labeled primers for DNA sequencing and analysis. *Proc. Natl. Acad. Sci.* USA 92:4347-4351.

Kamal, A., Laxman, E., and Rao, N. V. (1999) A mild and rapid regeneration of alcohols from their allylic ethers by chlorotrimethylsilane/sodium iodide, *Tetrahedron Lett.* 40:371-372.

Lee, L. G. et al. (1997) New energy transfer dyes for DNA Sequencing. *Nucleic Acids Res.* 25:2816-2822.

Li, J. (1999) Single Oligonucleotide Polymorphism Determination Using Primer Extension and Time-of-Flight Mass Spectrometry. *Electrophoresis*, 20:1258-1265.

Liu, H. et al. (2000) Development of Multichannel Devices with an Array of Electrospray Tips for High-Throughput Mass Spectrometry. *Anal. Chem.* 72:3303-3310.

Lyamichev, A. et al. (1999) Polymorphism Identification andQuantitative Detection of Genomic DNA by Invasive Cleavage of Oligonucleotide Probes. *Nat. Biotech.* 17:292-296.

Metzker, M. L., et al. (1994) Termination of DNA synthesis by novel 3'-modified deoxyribonucleoside 5'-triphosphates. Nucleic Acids Res. 22:4259-4267.

Olejnik, J., et al. (1995) Photocleavable biotin derivatives: a versatile approach for the isolation of biomolecules. Proc. Natl. Acad. Sci. USA. 92:7590-7594.

Pelletier, H., Sawaya, M. R., Kumar, A., Wilson, S. H., and Kraut J. (1994) Structures of ternary complexes of rat DNA polymerase β, a DNA template-primer, and ddCTP. Science 264:1891-1903.

Prober, J. M., Trainor, G. L., Dam, R. J., Hobbs, F. W., Robertson, C. W., Zagursky, R. J., Cocuzza, A. J., Jensen, M. A., Baumeister K. (1987) A system for rapid DNA sequencing with fluorescent chain-terminating dideoxynucleotides. Science 238:336-341.

Ronaghi, M., Uhlen, M., and Nyren, P. (1998) A sequencing Method based on real-time pyrophosphate. Science 281:364-365.

Rosenblum, B. B. et al. (1997) New dye-labeled terminators for improved DNA sequencing patterns. Nucleic Acids Res. 25:4500-4504.

Ross, P. et al. (1998) High Level Multiplex Genotyping by MALDI-TOF Mass Spectrometry. Nat. Biotech. 16:1347-1351.

Ross, P. L. et al. (1997) Discrimination of Single-Nucleotide Polymorphisms in Human DNA Using Peptide Nucleic Acid Probes Detected by MALDI-TOF Mass Spectrometry. Anal. Chem. 69:4197-4202.

Saxon, E. and Bertozzi, C. R. (2000) Cell surface engineering by a modified Staudinger reaction. Science 287:2007-2010.

Schena, M., Shalon, D., Davis, R., and Brown, P. O. (1995) Quantitative monitoring of gene expression patterns with a complementary DNA microarray. Science 270:467-470.

Speicher, M. R., Ballard, S. G. and Ward, D. C. (1996) Karyotyping human chromosomes by combinatorial multi-fluor FISH. Nature Genetics 12:368-375.

Stoerker, J. et al. (2000) Rapid Genotyping by MALDI-monitored nuclease selection from probe libraries. Nat. Biotech. 18:1213-1216.

Welch, M. B.,and Burgess, K. (1999) Synthesis of fluorescent, photolabile 3'-O-protected nucleoside triphosphates for the base addition sequencing scheme. Nucleosides and Nucleotides 18:197-201.

Woolley, A. T. et al. (1997) High-Speed DNA Genotyping Using Microfabricated Capillary Array Electrophoresis Chips. Anal. Chem. 69:2181-2186.

Fei, Z. et al. (1998) MALDI-TOF mass spectrometric typing of single nucleotide polymorphisms with mass-tagged ddNTPs. Nucleic Acids Research 26(11) :2827-2828.

Olejnik, J. et al. (1999) Photocleavable peptide-DNA conjugates:synthesis and applications to DNA analysis using MALDI-MS. Nucleic Acids Res. 27(23) :4626-4631; Arbo, et al. (1993) Solid Phase Synthesis of Protected Petides Using New Cobalt (III) Amine Linkers, Int. J. Peptide Protein Res. 42:138-154.

Arbo, et al. (1993) Solid Phase Synthesis of Protected Peptides Using New Cobalt (III) Amine Linkers, Int. J. Peptide Protein Res. 42:138-154.

Chiu, N. H., Tang, K., Yip, P., Braun, A., Koster, H., and Cantor C. R. (2000) Mass spectrometry of single-stranded restriction fragments captured by an undigested complementary sequence. Nucleic Acids Res. 28:E31.

Fu, D. J., Tang, K., Braun, A., Reuter, D., Darnhofer-Demar, B., Little D. P., O'Donnell, M. J., Cantor, C.R., and Koster, (1998) Sequencing exons 5 to 8 of the p53 gene by MALDI-TOF mass spectrometry. Nat. Biotechnol. 16:381-384.

Monforte, J. A., and Becker, C. H. (1997) High-throughput DNA analysis by time-of-flight mass spectrometry. Nat. Med. 3(3) :360-362.

Roskey, M. T, Juhasz P., Smirnov, I. P., Takach, E.J., and Martin S.A. (1996) Haff L.A., DNA sequencing by delayed extraction-matrix-assisted laser desorption/ionization time of flight mass spectrometry. Proc. Natl. Acad. Sci. USA. 93:4724-4729.

Tang, K., Fu, D. J., Julien, D., Braun, A., Cantor, C. R., and Koster H.1999) Chip-based genotyping by mass spectrometry. Proc. Natl. Acad. Sci. USA. 96:10016-10020.

Tong, X. and Smith L. M. (1992) Solid-Phase Method for the Purification of DNA Sequencing Reactions. Anal. Chem. 64:2672-2677.

Jurinke, C., van de Boom, D., Collazo, V., Luchow, A., Jacob, A, Koster, H., (1997) Recovery of nucleic acids from immobilized biotin-streptavidin complexes using ammonium hydroxide and application in MALDI-TOF mass spectrometry. Anal. Chem. 69:904-910.

Lee, L. G., Spurgeon, S. L., Heiner, C. R., Benson, S. C., Rosenblum, B. B., Menchen, S. M., Graham, R. J., Constantinescu, A., Upadhya, K. G. and Cassel, J.M. (1997) New energy transfer dyes for DNA sequencing. Nucleic Acids Res. 25:2816-2822.

U.S. Appl. No. 09/972,364, filed Oct. 5, 2001.
U.S. Appl. No. 09/823,181, filed Mar. 30, 2001.
U.S. Appl. No. 09/684,670, filed Oct. 6, 2001.
U.S. Appl. No. 10/194,882, filed Mar. 30, 2001.
U.S. Appl. No. 09/658,077, filed Sep. 11, 2000.
U.S. Appl. No. 10/380,256, filed Mar. 30, 2001.
U.S. Appl. No. 11/810,509, filed Jun. 5, 2007, Ju et al.

Preliminary Amendment filed wih U.S. Appl. No. 11/810,509, filed Jun. 5, 2007, Ju et al.

Kraevskii, A.A. et al., (1987), Substrate Inhibitors of DNA Biosynthesis, Molecular Biology, 21:25-29.

Office Action issued Oct. 25, 2002 in connection with U.S. Appl. No. 09/972,364.

Office Action issued Mar. 14, 2003 in connection with U.S. Appl. No. 09/972,364.

Jingyue Ju, et al. "Cassette labeling for facile construction of energy transfer fluorescent primers", Nuc. Acids Res. 24(6) :1144-1148 (1996).

Lee LG, et al. "DNA sequencing with dye labeled terminators and T7 DNA polymerase effect of dyes and dNTPs on incorporation of dye terminators and probability analysis of termination fragments". Nucleic Acids Res. 20: 2471 2483 (1992).

Bergseid M., Baytan A. R., Wiley J. P., Ankener W.M., Stolowitz, Hughs K.A., Chestnut J.D., "Small-molecule base chemical affinity system for the purification of proteins", BioTechniques 29:1126-1133 (2000).

Buschmann et al., "The Complex Formation of α, ω-Dicarboxylic Acids and α, ω-Diols with Cucurbituril and α-Cyclodextrin", Acta Chim. Slov. 46(3) :405-411 (1999).

Kolb et al., "Click Chemistry: Diverse Chemical Function From a Few Good Reactions", Angew. Chem. Int. Ed. 40:2004-2021 (2001).

Lewis et al., "Click Chemistry in Situ: Acetylcholinesterase as a Reaction Vessel for the Selective Assembly of a Femtomolar Inhibitor from an Array of Building Blocks", Angew. Chem. Int. Ed., 41(6) :1053-1057 (2002).

Seo et al., "Click Chemistry to Construct Fluorescent Oligonucleotides for DNA Sequencing", J. Org. Chem. 68 :609-612 (2003).

Fallahpour, "Photochemical and Thermal reactions of Azido-Oligopyridines: Diazepinones, a New Class of Metal-Complex Ligands", Helvetica Chimica Acta. 83:384-393 (2000).

Ikeda, K. et al. "A Non-Radioactive DNA Sequencing Method Using Biotinylated Dideoxynucleoside Triphosphates and Delta TTH DNA Polymerase" DNA Research, 2(31) :225-227 (1995).

Kim Sobin et al. "Solid Phase Capturable Dideoxynucleotides for Multiplex Genotyping Using Mass Spectrometry" Nucleic Acids Research, 30(16) :e85.1-e85.6, (2002).

Wendy S Jen, John J.M. Wiener, and David W.C. MacMillan "New Strategies for Organic Catalysis: The First Enantioselective Orgacnocatalytic 1,3-Dipolar Cycloaddition" J. Am. Chem. Soc., 122, 9874-9875 (2000).

Supplementary European Search Report issued Feb. 16, 2004 in connection with European Patent Application No. 01 97 7533.

Supplementary European Search Report issued Feb. 9, 2007 in connection with European Patent Application No. 03 76 4568.6.

Supplementary European Search Report issued May 25, 2005 in connection with European Patent Application No. 02 72 8606.1.

Supplementary European Search Report issued Jun. 7, 2005 in connection with European Patent Application No. 01 96 8905.

International Preliminary Examination Report issued on Mar. 18, 2005 in connection with PCT/US03/21818.

International Preliminary Examination Report issued on Apr. 3, 2003 in connection with PCT/US01/31243.

International Preliminary Examination Report issued on Feb. 25, 2003 in connection with PCT/US01/28967.

International Preliminary Examination Report issued on Mar. 17, 2003 in connection with PCT/US02/09752.

International Preliminary Report on Patentability issued on Sep. 5, 2006 in connection with PCT/US05/006960.

International Search Report issued May 13, 2002 in connection with PCT/US01/31243.

International Search Report issued Jan. 23, 2002 in connection with PCT/US01/28967.

International Search Report issued Sep. 18, 2002 in connection with PCT/US02/09752.

International Search Report issued Sep. 26, 2003 in connection with PCT/US03/21818.

International Search Report issued Jun. 8, 2004 in connection with PCT/US03/39354.

International Search Report issued Nov. 4, 2005 in connection with PCT/US05/06960.

International Search Report issued Dec. 15, 2006 in connection with PCT/US05/13883.

Written Opinion of the International Searching Authority issued Oct. 27, 2005 in connection with PCT/US05/06960.

Written Opinion of the International Searching Authority issued Dec. 15, 2006 in connection with PCT/US05/13883.

Elango et al. (1983) Amino Acid Sequence of Human Respiratory Syncitial Nucleocaspid Protein, Nucleic Acids Research 11(17):5491-5951.

Buck et al. (1999) Design Strategies and Performance of Custom DNA Sequencing Primers, Biotechniques 27 (3) 528-536.

Hafliger et al. (1997) Semi-nested RT-PCR Systems for Small Round Structured Viruses and Detection of Enteric Viruses in Seafood. Int. J. Food Microbiol. 37:27-36.

Leroy et al. (2000) Diagnosis of Ebola Haemorrhagic Fever by RT-PCR in an Epidemic Setting. J. Med. Virol. 60:463-467.

Kokoris et al. (2000) High-Throughput SNP Genotyping with the Masscode System. Molecular Diagnosis 5(4):329-340.

Kim et al. (2003) Multiplex Genotyping of the Human Beta2-adrenergic Receptor Gene Using Solid-Phase Capturable Dideoxynucleotides and Mass Spectrometry 316:251-258.

Partial European Search Report issued Apr. 26, 2007 in connection with European Patent Application No. 07004522.4.

U.S. Appl. No. 10/591,520, Ju et al., filed Sep. 1, 2006.

Hultman et al., Direct Solid Phase Sequencing of Genomic and Plasmid DNA Using Magnetic Beads as Solid Support, *Nucleic Acids Research*, 17(3):4937-4946, 1989.

Henner, W.D. et al., (1983), Enzyme Action at 3' Termini of Ionizing Radiation-Induced DNA Strand Breaks, J. Biol. Chem. 258 (24): 151198-15205.

* cited by examiner

Asp = Aspartic Acid

(Nitro-Benzyl)-dATP

F-(Nitro-Benzyl)-dCTP

2F-(Nitro-Benzyl)-dGTP

2(Meo)-(Nitro-Benzyl)-dTTP

R = H, MOM or Allyl

MASSIVE PARALLEL METHOD FOR DECODING DNA AND RNA

This application is a divisional of U.S. Ser. No. 09/972,364, filed Oct. 5, 2001 now U.S. Pat. No. 6,664,079, which is a continuation-in-part of U.S. Ser. No. 09/684,670, filed Oct. 6, 2000, now abandoned and which claims priority of U.S. Provisional Application No. 60/300,894, filed Jun. 26, 2001, the contents of each of which are hereby incorporated by reference in their entireties into this application.

The invention disclosed herein was made with government support under National Science Foundation award no. BES0097793. Accordingly, the U.S. Government has certain rights in this invention.

BACKGROUND OF THE INVENTION

Throughout this application, various publications are referenced in parentheses by author and year. Full citations, for these references may be found at the end of the specification immediately preceding, the claims. The disclosures of these publications in their entireties are hereby incorporated by reference into this application to more fully describe the state of the art to which this invention pertains.

The ability to sequence deoxyribonucleic acid (DNA) accurately and rapidly is revolutionizing biology and medicine. The confluence of the massive Human Genome Project is driving an exponential growth in the development of high throughput genetic analysis technologies. This rapid technological development involving chemistry, engineering, biology, and computer science makes it possible to move from studying single genes at a time to analyzing and comparing entire genomes.

With the completion of the first entire human genome sequence map, many areas in the genome that are highly polymorphic in both exons and introns will be known. The pharmacogenomics challenge is to comprehensively identify the genes and functional polymorphisms associated with the variability in drug response (Roses, 2000). Resequencing of polymorphic areas in the genome that are linked to disease development will contribute greatly to the understanding of diseases, such as cancer, and therapeutic development. Thus, high-throughput accurate methods for resequencing the highly variable intron/exon regions of the genome are needed in order to explore the full potential of the complete human genome sequence map. The current state-of-the-art technology for high throughput DNA sequencing, such as used for the Human Genome Project (Pennisi 2000), is capillary array DNA sequencers using laser induced fluorescence detection (Smith et al., 1986; Ju et al. 1995, 1996; Kheterpal et al. 1996; Salas-Solano et al. 1998). Improvements in the polymerase that lead to uniform termination efficiency and the introduction of thermostable polymerases have also significantly improved the quality of sequencing data (Tabor and Richardson, 1987, 1995). Although capillary array DNA sequencing technology to some extent addresses the throughput and read length requirements of large scale DNA sequencing projects, the throughput and accuracy required for mutation studies needs to be improved for a wide variety of applications ranging from disease gene discovery to forensic identification. For example, electrophoresis based DNA sequencing methods have difficulty detecting heterozygotes unambiguously and are not 100% accurate in regions rich in nucleotides comprising guanine or cytosine due to compressions (Bowling et al. 1991; Yamakawa et al. 1997). In addition, the first few bases after the priming site are often masked by the high fluorescence signal from excess dye-labeled primers or dye-labeled terminators, and are therefore difficult to identify. Therefore, the requirement of electrophoresis for DNA sequencing is still the bottleneck for high-throughput DNA sequencing and mutation detection projects.

The concept of sequencing DNA by synthesis without using electrophoresis was first revealed in 1988 (Hyman, 1988) and involves detecting the identity of each nucleotide as it is incorporated into the growing strand of DNA in a polymerase reaction. Such a scheme coupled with the chip format and laser-induced fluorescent detection has the potential to markedly increase the throughput of DNA sequencing projects. Consequently, several groups have investigated such a system with an aim to construct an ultra high-throughput DNA sequencing procedure (Cheeseman 1994, Metzker et al. 1994). Thus far, no complete success of using such a system to unambiguously sequence DNA has been reported. The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi 1998). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. This procedure can only sequence up to 30 base pairs (bps) of nucleotide sequences, and each of the 4 nucleotides needs to be added separately and detected separately. Long stretches of the same bases cannot be identified unambiguously with the pyrosequencing method.

More recent work in the literature exploring DNA sequencing by a synthesis method is mostly focused on designing and synthesizing a photocleavable chemical moiety that is linked to a fluorescent dye to cap the 3'-OH group of deoxynucleoside triphosphates (dNTPs) (Welch et al. 1999). Limited success for the incorporation of the 3'-modified nucleotide by DNA polymerase is reported. The reason is that the 3'-position on the deoxyribose is very close to the amino acid residues in the active site of the polymerase, and the polymerase is therefore sensitive to modification in this area of the deoxyribose ring. On the other hand, it is known that modified DNA polymerases (Thermo Sequenase and Taq FS polymerase) are able to recognize nucleotides with extensive modifications with bulky groups such as energy transfer dyes at the 5-position of the pyrimidines (T and C) and at the 7-position of purines (G and A) (Rosenblum et al. 1997, Zhu et al. 1994). The ternary complexes of rat DNA polymerase, a DNA template-primer, and dideoxycytidine triphosphate (ddCTP) have been determined (Pelletier et al. 1994) which supports this fact. As shown in FIG. 1, the 3-D structure indicates that the surrounding area of the 3'-position of the deoxyribose ring in ddCTP is very crowded, while there is ample space for modification on the 5-position the cytidine base.

The approach disclosed in the present application is to make nucleotide analogues by linking a unique label such as a fluorescent dye or a mass tag through a cleavable linker to the nucleotide base or an analogue of the nucleotide base, such as to the 5-position of the pyrimidines (T and C) and to the 7-position of the purines (G and A), to use a small cleavable chemical moiety to cap the 3'-OH group of the deoxyribose to make it nonreactive, and to incorporate the nucleotide analogues into the growing DNA strand as terminators. Detection of the unique label will yield the sequence identity of the nucleotide. Upon removing the label and the 3'-OH capping group, the polymerase reaction will proceed to incorporate the next nucleotide analogue and detect the next base.

It is also desirable to use a photocleavable group to cap the 3'-OH group. However, a photocleavable group is generally bulky and thus the DNA polymerase will have difficulty to incorporate the nucleotide analogues containing a photocleavable moiety capping the 3'-OH group. If small chemical moieties that can be easily cleaved chemically with high yield can be used to cap the 3'-OH group, such nucleotide analogues should also be recognized as substrates for DNA polymerase. It has been reported that 3'-O-methoxy-deoxynucleotides are good substrates for several polymerases (Axelrod et al. 1978). 3'-O-allyl-dATP was also shown to be incorporated by Ventr(exo-) DNA polymerase in the growing strand of DNA (Metzker et al. 1994). However, the procedure to chemically cleave the methoxy group is stringent and requires anhydrous conditions. Thus, it is not practical to use a methoxy group to cap the 3'-OH group for sequencing DNA by synthesis. An ester group was also explored to cap the 3'-OH group of the nucleotide, but it was shown to be cleaved by the nucleophiles in the active site in DNA polymerase (Canard et al. 1995). Chemical groups with electrophiles such as ketone groups are not suitable for protecting the 3'-OH of the nucleotide in enzymatic reactions due to the existence of strong nucleophiles in the polymerase. It is known that MOM ($-CH_2OCH_3$) and allyl ($-CH_2CH=CH_2$) groups can be used to cap an $-OH$ group, and can be cleaved chemically with high yield (Ireland et al. 1986; Kamal et al. 1999). The approach disclosed in the present application is to incorporate nucleotide analogues, which are labeled with cleavable, unique labels such as fluorescent dyes or mass tags and where the 3'-OH is capped with a cleavable chemical moiety such as either a MOM group ($-CH_2OCH_3$) or an allyl group ($-CH_2CH=CH_2$), into the growing strand DNA as terminators. The optimized nucleotide set ($3'-RO$-A-$_{LABEL1}$, $3'-RO$-C-$_{LABEL2}$, $3'$-RO-G-$_{LABEL3}$, $3'-RO$-T-$_{LABEL4}$, where R denotes the chemical group used to cap the 3'-OH) can then be used for DNA sequencing by the synthesis approach.

There are many advantages of using mass spectrometry (MS) to detect small and stable molecules. For example, the mass resolution can be as good as one dalton. Thus, compared to gel electrophoresis sequencing systems and the laser induced fluorescence detection approach which have overlapping fluorescence emission spectra, leading to heterozygote detection difficulty, the MS approach disclosed in this application produces very high resolution of sequencing data by detecting the cleaved small mass tags instead of the long DNA fragment. This method also produces extremely fast separation in the time scale of microseconds. The high resolution allows accurate digital mutation and heterozygote detection. Another advantage of sequencing with mass spectrometry by detecting the small mass tags is that the compressions associated with gel based systems are completely eliminated.

In order to maintain a continuous hybridized primer extension product with the template DNA, a primer that contains a stable loop to form an entity capable of self-priming in a polymerase reaction can be ligated to the 3' end of each single stranded DNA template that is immobilized on a solid surface such as a chip. This approach will solve the problem of washing off the growing extension products in each cycle.

Saxon and Bertozzi (2000) developed an elegant and highly specific coupling chemistry linking a specific group that contains a phosphine moiety to an azido group on the surface of a biological cell. In the present application, this coupling chemistry is adopted to create a solid surface which is coated with a covalently linked phosphine moiety, and to generate polymerase chain reaction (PCR) products that contain an azido group at the 5' end for specific coupling of the DNA template with the solid surface. One example of a solid surface is glass channels which have an inner wall with an uneven or porous surface to increase the surface area. Another example is a chip.

The present application discloses a novel and advantageous system for DNA sequencing by the synthesis approach which employs a stable DNA template, which is able to self prime for the polymerase reaction, covalently linked to a solid surface such as a chip, and 4 unique nucleotides analogues ($_{3'-RO}$-A-$_{LABEL1}$, $_{3'-RO}$-C-$_{LABEL2}$, $_{3'-RO}$-G-$_{LABEL3}$, $_{3'-RO}$-T-$_{LABEL4}$). The success of this novel system will allow the development of an ultra high-throughput and high fidelity DNA sequencing system for polymorphism, pharmacogenetics applications and for whole genome sequencing. This fast and accurate DNA resequencing system is needed in such fields as detection of single nucleotide polymorphisms (SNPs) (Chee et al. 1996), serial analysis of gene expression (SAGE) (Velculescu et al. 1995), identification in forensics, and genetic disease association studies.

SUMMARY OF THE INVENTION

This invention is directed to a method for sequencing a nucleic acid by detecting the identity of a nucleotide analogue after the nucleotide analogue is incorporated into a growing strand of DNA in a polymerase reaction, which comprises the following steps:

(i) attaching a 5' end of the nucleic acid to a solid surface;

(ii) attaching a primer to the nucleic acid attached to the solid surface;

(iii) adding a polymerase and one or more different nucleotide analogues to the nucleic acid to thereby incorporate a nucleotide analogue into the growing strand of DNA, wherein the incorporated nucleotide analogue terminates the polymerase reaction and wherein each different nucleotide analogue comprises (a) a base selected from the group consisting of adenine, guanine, cytosine, thymine, and uracil, and their analogues; (b) a unique label attached through a cleavable linker to the base or to an analogue of the base; (c) a deoxyribose; and (d) a cleavable chemical group to cap an $-OH$ group at a 3'-position of the deoxyribose;

(iv) washing the solid surface to remove unincorporated nucleotide analogues;

(v) detecting the unique label attached to the nucleotide analogue that has been incorporated into the growing strand of DNA, so as to thereby identify the incorporated nucleotide analogue;

(vi) adding one or more chemical compounds to permanently cap any unreacted $-OH$ group on the primer attached to the nucleic acid or on a primer extension strand formed by adding one or more nucleotides or nucleotide analogues to the primer;

(vii) cleaving the cleavable linker between the nucleotide analogue that was incorporated into the growing strand of DNA and the unique label;

(viii) cleaving the cleavable chemical group capping the $-OH$ group at the 3'-position of the deoxyribose to uncap the $-OH$ group, and washing the solid surface to remove cleaved compounds; and (ix) repeating steps (iii) through (viii) so as to detect the identity of a newly incorporated nucleotide analogue into the growing strand of DNA;

wherein if the unique label is a dye, the order of steps (v) through (vii) is: (v), (vi), and (vii); and wherein if the unique label is a mass tag, the order of steps (v) through (vii) is: (vi), (vii), and (v).

The invention provides a method of attaching a nucleic acid to a solid surface which comprises:

(i) coating the solid surface with a phosphine moiety, (ii) attaching an azido group to a 5' end of the nucleic acid, and (iii) immobilizing the 5' end of the nucleic acid to the solid surface through interaction between the phosphine moiety on the solid surface and the azido group on the 5' end of the nucleic acid.

The invention provides a nucleotide analogue which comprises:

(a) a base selected from the group consisting of adenine or an analogue of adenine, cytosine or an analogue of cytosine, guanine or an analogue of guanine, thymine or an analogue of thymine, and uracil or an analogue of uracil;

(b) a unique label attached through a cleavable linker to the base or to an analogue of the base;

(c) a deoxyribose; and (d) a cleavable chemical group to cap an —OH group at a 3'-position of the deoxyribose.

The invention provides a parallel mass spectrometry system, which comprises a plurality of atmospheric pressure chemical ionization mass spectrometers for parallel analysis of a plurality of samples comprising mass tags.

DETAILED DESCRIPTION OF THE INVENTION

Figure 1:
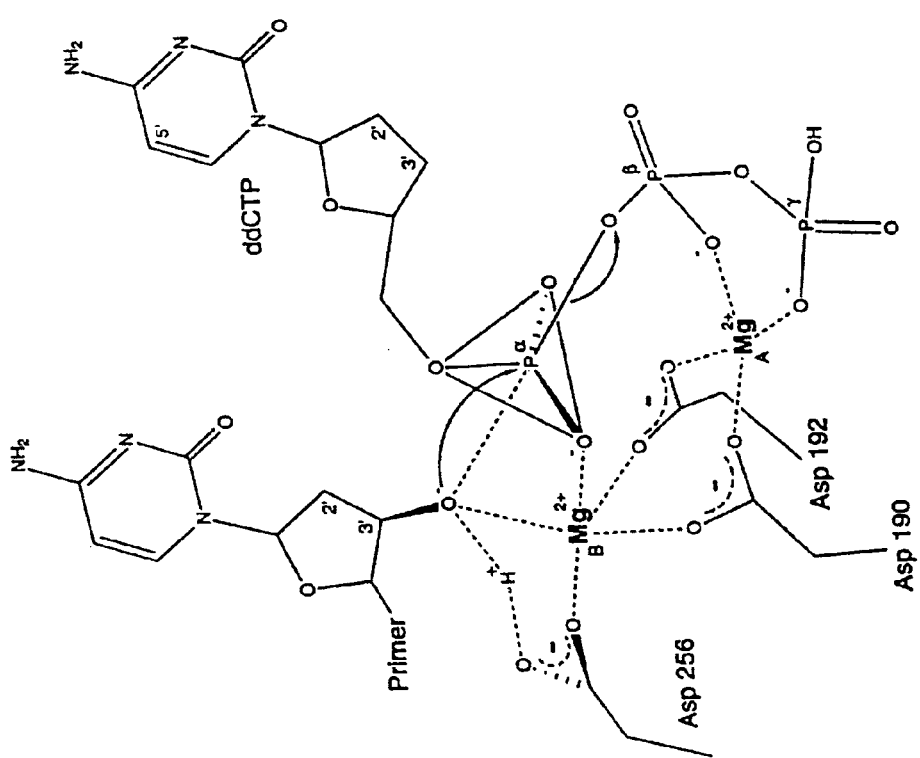
FIG. 1: The 3D structure of the ternary complexes of rat DNA polymerase, a DNA template-primer, and dideoxycytidine triphosphate (ddCTP). The left side of the illustration shows the mechanism for the addition of ddCTP and the right side of the illustration shows the active site of the polymerase. Note that the 3' position of the dideoxyribose ring is very crowded, while ample space is available at the 5 position of the cytidine base.
Figure 1:
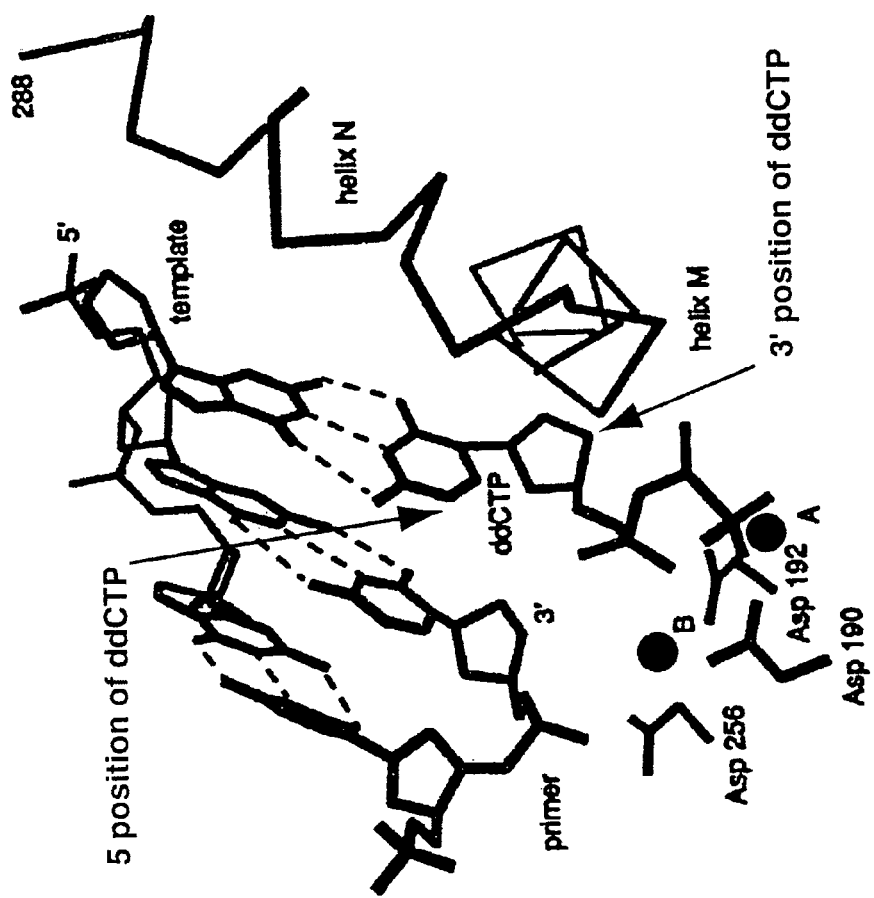

The following definitions are presented as an aid in understanding this invention.

As used herein, to cap an —OH group means to replace the "H" in the —OH group with a chemical group. As disclosed herein, the —OH group of the nucleotide analogue is capped with a cleavable chemical group. To uncap an —OH group means to cleave the chemical group from a capped —OH group and to replace the chemical group with "H", i.e., to replace the "R" in —OR with "H" wherein "R" is the chemical group used to cap the —OH group.

The nucleotide bases are abbreviated as follows: adenine (A), cytosine (C), guanine (G), thymine (T), and uracil (U).

An analogue of a nucleotide base refers to a structural and functional derivative of the base of a nucleotide which can be recognized by polymerase as a substrate. That is, for example, an analogue of adenine (A) should form hydrogen bonds with thymine (T), a C analogue should form hydrogen bonds with G, a G analogue should form hydrogen bonds with C, and a T analogue should form hydrogen bonds with A, in a double helix format. Examples of analogues of nucleotide bases include, but are not limited to, 7-deaza-adenine and 7-deaza-guanine, wherein the nitrogen atom at the 7-position of adenine or guanine is substituted with a carbon atom.

A nucleotide analogue refers to a chemical compound that is structurally and functionally similar to the nucleotide, i.e. the nucleotide analogue can be recognized by polymerase as a substrate. That is, for example, a nucleotide analogue comprising adenine or an analogue of adenine should form hydrogen bonds with thymine, a nucleotide analogue comprising C or an analogue of C should form hydrogen bonds with G, a nucleotide analogue comprising G or an analogue of G should form hydrogen bonds with C, and a nucleotide analogue comprising T or an analogue of T should form hydrogen bonds with A, in a double helix format. Examples of nucleotide analogues disclosed herein include analogues which comprise an analogue of the nucleotide base such as 7-deaza-adenine or 7-deaza-guanine, wherein the nitrogen atom at the 7-position of adenine or guanine is substituted with a carbon atom. Further examples include analogues in which a label is attached through a cleavable linker to the 5-position of cytosine or thymine or to the 7-position of deaza-adenine or deaza-guanine. Other examples include analogues in which a small chemical moiety such as —CH$_2$OCH$_3$ or —CH$_2$CH=CH$_2$ is used to cap the —OH group at the 3'-position of deoxyribose. Analogues of dideoxynucleotides can similarly be prepared.

As used herein, a porous surface is a surface which contains pores or is otherwise uneven, such that the surface area of the porous surface is increased relative to the surface area when the surface is smooth.

The present invention is directed to a method for sequencing a nucleic acid by detecting the identity of a nucleotide analogue after the nucleotide analogue is incorporated into a growing strand of DNA in a polymerase reaction, which comprises the following steps:

(i) attaching a 5' end of the nucleic acid to a solid surface;

(ii) attaching a primer to the nucleic acid attached to the solid surface;

(iii) adding a polymerase and one or more different nucleotide analogues to the nucleic acid to thereby incorporate a nucleotide analogue into the growing strand of DNA, wherein the incorporated nucleotide analogue terminates the polymerase reaction and wherein each different nucleotide analogue comprises (a) a base selected from the group consisting of adenine, guanine, cytosine, thymine, and uracil, and their analogues; (b) a unique label attached through a cleavable linker to the base or to an analogue of the base; (c) a deoxyribose; and (d) a cleavable chemical group to cap an —OH group at a 3'-position of the deoxyribose;

(iv) washing the solid surface to remove unincorporated nucleotide analogues;

(v) detecting the unique label attached to the nucleotide analogue that has been incorporated into the growing strand of DNA, so as to thereby identify the incorporated nucleotide analogue;

(vi) adding one or more chemical compounds to permanently cap any unreacted —OH group on the primer attached to the nucleic acid or on a primer extension strand formed by adding one or more nucleotides or nucleotide analogues to the primer;

(vii) cleaving the cleavable linker between the nucleotide analogue that was incorporated into the growing strand of DNA and the unique label;

(viii) cleaving the cleavable chemical group capping the —OH group at the 3'-position of the deoxyribose to uncap the —OH group, and washing the solid surface to remove cleaved compounds; and (ix) repeating steps (iii) through (viii) so as to detect the identity of a newly incorporated nucleotide analogue into the growing strand of DNA;

wherein if the unique label is a dye, the order of steps (v) through (vii) is: (v), (vi), and (vii); and wherein if the unique label is a mass tag, the order of steps (v) through (vii) is: (vi), (vii), and (v).

In one embodiment of any of the nucleotide analogues described herein, the nucleotide base is adenine. In one embodiment, the nucleotide base is guanine. In one embodiment, the nucleotide base is cytosine. In one embodiment, the nucleotide base is thymine. In one embodiment, the nucleotide base is uracil. In one embodiment, the nucleotide base is an analogue of adenine. In one embodiment, the nucleotide base is an analogue of guanine. In one embodiment, the nucleotide is base is an analogue of cytosine. In one embodiment, the nucleotide base is an analogue of thymine. In one embodiment, the nucleotide base is an analogue of uracil.

In different embodiments of any of the inventions described herein, the solid surface is glass, silicon, or gold. In different embodiments, the solid surface is a magnetic bead, a chip, a channel in a chip, or a porous channel in a chip. In one embodiment, the solid surface is glass. In one embodiment, the solid surface is silicon. In one embodiment, the solid surface is gold. In one embodiments, the solid surface is a magnetic bead. In one embodiment, the solid surface is a chip. In one embodiment, the solid surface is a channel in a chip. In one embodiment, the solid surface is a porous channel in a chip. Other materials can also be used as long as the material does not interfere with the steps of the method.

In one embodiment, the step of attaching the nucleic acid to the solid surface comprises:
  (i) coating the solid surface with a phosphine moiety,
  (ii) attaching an azido group to the 5' end of the nucleic acid, and
  (iii) immobilizing the 5' end of the nucleic acid to the solid surface through interaction between the phosphine moiety on the solid surface and the azido group on the 5' end of the nucleic acid.

In one embodiment, the step of coating the solid surface with the phosphine moiety comprises:
  (i) coating the surface with a primary amine, and
  (ii) covalently coupling a N-hydroxysuccinimidyl ester of triarylphosphine with the primary amine.

In one embodiment, the nucleic acid that is attached to the solid surface is a single-stranded deoxyribonucleic acid (DNA). In another embodiment, the nucleic acid that is attached to the solid surface in step (i) is a double-stranded DNA, wherein only one strand is directly attached to the solid surface, and wherein the strand that is not directly attached to the solid surface is removed by denaturing before proceeding to step (ii). In one embodiment, the nucleic acid that is attached to the solid surface is a ribonucleic acid (RNA), and the polymerase in step (iii) is reverse transcriptase.

In one embodiment, the primer is attached to a 3' end of the nucleic acid in step (ii), and the attached primer comprises a stable loop and an —OH group at a 3'-position of a deoxyribose capable of self-priming in the polymerase reaction. In one embodiment, the step of attaching the primer to the nucleic acid comprises hybridizing the primer to the nucleic acid or ligating the primer to the nucleic acid. In one embodiment, the primer is attached to the nucleic acid through a ligation reaction which links the 3' end of the nucleic acid with the 5' end of the primer.

In one embodiment, one or more of four different nucleotide analogs is added in step (iii), wherein each different nucleotide analogue comprises a different base selected from the group consisting of thymine or uracil or an analogue of thymine or uracil, adenine or an analogue of adenine, cytosine or an analogue of cytosine, and guanine or an analogue of guanine, and wherein each of the four different nucleotide analogues comprises a unique label.

In one embodiment, the cleavable chemical group that caps the —OH group at the 3'-position of the deoxyribose in the nucleotide analogue is —CH$_2$OCH$_3$ or —CH$_2$CH═CH$_2$. Any chemical group could be used as long as the group 1) is stable during the polymerase reaction, 2) does not interfere with the recognition of the nucleotide analogue by polymerase as a substrate, and 3) is cleavable.

In one embodiment, the unique label that is attached to the nucleotide analogue is a fluorescent moiety or a fluorescent semiconductor crystal. In further embodiments, the fluorescent moiety is selected from the group consisting of 5-carboxyfluorescein, 6-carboxyrhodamine-6G, N,N,N',N'-tetramethyl-6-carboxyrhodamine, and 6-carboxy-X-rhodamine. In one embodiment, the fluorescent moiety is 5-carboxyfluorescein. In one embodiment, the fluorescent moiety is 6-carboxyrhodamine-6G, N,N,N',N'-tetramethyl-6-carboxyrhodamine. In one embodiment, the fluorescent moiety is 6-carboxy-X-rhodamine.

In one embodiment, the unique label that is attached to the nucleotide analogue is a fluorescence energy transfer tag which comprises an energy transfer donor and an energy transfer acceptor. In further embodiments, the energy transfer donor is 5-carboxyfluorescein or cyanine, and wherein the energy transfer acceptor is selected from the group consisting of dichlorocarboxyfluorescein, dichloro-6-carboxyrhodamine-6G, dichloro-N,N,N',N'-tetramethyl-6-carboxyrhodamine, and dichloro-6-carboxy-X-rhodamine. In one embodiment, the energy transfer acceptor is dichlorocarboxyfluorescein. In one embodiment, the energy transfer acceptor is dichloro-6-carboxyrhodamine-6G. In one embodiment, the energy transfer acceptor is dichloro-N,N,N',N'-tetramethyl-6-carboxyrhodamine. In one embodiment, the energy transfer acceptor is dichloro-6-carboxy-X-rhodamine.

In one embodiment, the unique label that is attached to the nucleotide analogue is a mass tag that can be detected and differentiated by a mass spectrometer. In further embodiments, the mass tag is selected from the group consisting of a 2-nitro-α-methyl-benzyl group, a 2-nitro-α-methyl-3-fluorobenzyl group, a 2-nitro-α-methyl-3,4-difluorobenzyl group, and a 2-nitro-α-methyl-3,4-dimethoxybenzyl group. In one embodiment, the mass tag is a 2-nitro-α-methyl-benzyl group. In one embodiment, the mass tag is a 2-nitro-α-methyl-3-fluorobenzyl group. In one embodiment, the mass tag is a 2-nitro-α-methyl-3,4-difluorobenzyl group. In one embodiment, the mass tag is a 2-nitro-α-methyl-3,4-dimethoxybenzyl group. In one embodiment, the mass tag is detected using a parallel mass spectrometry system which comprises a plurality of atmospheric pressure chemical ionization mass spectrometers for parallel analysis of a plurality of samples comprising mass tags.

In one embodiment, the unique label is attached through a cleavable linker to a 5-position of cytosine or thymine or to a 7-position of deaza-adenine or deaza-guanine. The unique label could also be attached through a cleavable linker to another position in the nucleotide analogue as long as the attachment of the label is stable during the polymerase reaction and the nucleotide analog can be recognized by polymerase as a substrate. For example, the cleavable label could be attached to the deoxyribose.

In one embodiment, the linker between the unique label and the nucleotide analogue is cleaved by a means selected from the group consisting of one or more of a physical means, a chemical means, a physical chemical means, heat, and light. In one embodiment, the linker is cleaved by a physical means. In one embodiment, the linker is cleaved by a chemical means. In one embodiment, the linker is cleaved by a physical chemical means. In one embodiment, the linker is cleaved by heat. In one embodiment, the linker is cleaved by light. In one embodiment, the linker is cleaved by ultraviolet light. In a further embodiment, the cleavable linker is a photocleavable linker which comprises a 2-nitrobenzyl moiety.

In one embodiment, the cleavable chemical group used to cap the —OH group at the. 3'-position of the deoxyribose is cleaved by a means selected from the group consisting of one or more of a physical means, a chemical means, a physical chemical means, heat, and light. In one embodiment, the linker is cleaved by a physical chemical means. In one embodiment, the linker is cleaved by heat. In one embodiment, the linker is cleaved by light. In one embodiment, the linker is cleaved by ultraviolet light.

In one embodiment, the chemical compounds added in step (vi) to permanently cap any unreacted —OH group on the primer attached to the nucleic acid or on the primer extension strand are a polymerase and one or more different dideoxynucleotides or analogues of dideoxynucleotides. In further embodiments, the different dideoxynucleotides are selected from the group consisting of 2',3'-dideoxyadenosine 5'-triphosphate, 2',3'-dideoxyguanosine 5'-triphosphate, 2',3'-dideoxycytidine 5'-triphosphate, 2',3'-dideoxythymidine 5'-triphosphate, 2',3'-dideoxyuridine 5'-triphosphase, and their analogues. In one embodiment, the dideoxynucleotide is 2',3'-dideoxyadenosine 5'-triphosphate. In one embodiment, the dideoxynucleotide is 2',3'-dideoxyguanosine 5'-triphosphate. In one embodiment, the dideoxynucleotide is 2',3'-dideoxycytidine 5'-triphosphate. In one embodiment, the dideoxynucleotide is 2',3'-dideoxythymidine 5'-triphosphate. In one embodiment, the dideoxynucleotide is 2',3'-dideoxyuridine 5'-triphosphase. In one embodiment, the dideoxynucleotide is an analogue of 2',3'-dideoxyadenosine 5'-triphosphate. In one embodiment, the dideoxynucleotide is an analogue of 2',3'-dideoxyguanosine 5'-triphosphate. In one embodiment, the dideoxynucleotide is an analogue of 2',3'-dideoxycytidine 5'-triphosphate. In one embodiment, the dideoxynucleotide is an analogue of 2',3'-dideoxythymidine 5'-triphosphate. In one embodiment, the dideoxynucleotide is an analogue of 2',3'-dideoxyuridine 5'-triphosphase.

In one embodiment, a polymerase and one or more of four different dideoxynucleotides are added in step (vi), wherein each different dideoxynucleotide is selected from the group consisting of 2',3'-dideoxyadenosine 5'-triphosphate or an analogue of 2',3'-dideoxyadenosine 5'-triphosphate; 2',3'-dideoxyguanosine 5'-triphosphate or an analogue of 2',3'-dideoxyguanosine 5'-triphoshate; 2',3'-dideoxycytidine 5'-triphosphate or an analogue of 2',3'-dideoxycytidine 5'-triphosphate; and 2',3'-dideoxythymidine 5'-triphosphate or 2',3'-dideoxyuridine 5'-triphosphase or an analogue of 2',3'-dideoxythymidine 5'-triphosphate or an analogue of 2',3'-dideoxyuridine 5'-triphosphase. In one embodiment, the dideoxynucleotide is 2',3'-dideoxyadenosine 5'-triphosphate. In one embodiment, the dideoxynucleotide is an analogue of 2',3'-dideoxyadenosine 5'-triphosphate. In one embodiment, the dideoxynucleotide is 2',3'-dideoxyguanosine 5'-triphosphate. In one embodiment, the dideoxynucleotide is an analogue of 2',3'-dideoxyguanosine 5'-triphosphate. In one embodiment, the dideoxynucleotide is 2',3'-dideoxycytidine 5'-triphosphate. In one embodiment, the dideoxynucleotide is an analogue of 2',3'-dideoxycytidine 5'-triphosphate. In one embodiment, the dideoxynucleotide is 2',3'-dideoxythymidine 5'-triphosphate. In one embodiment, the dideoxynucleotide is 2',3'-dideoxyuridine 5'-triphosphase. In one embodiment, the dideoxynucleotide is an analogue of 2',3'-dideoxythymidine 5'-triphosphate. In one embodiment, the dideoxynucleotide is an analogue of 2',3'-dideoxyuridine 5'-triphosphase.

Another type of chemical compound that reacts specifically with the —OH group could also be used to permanently cap any unreacted —OH group on the primer attached to the nucleic acid or on an extension strand formed by adding one or more nucleotides or nucleotide analogues to the primer.

The invention provides a method for simultaneously sequencing a plurality of different nucleic acids, which comprises simultaneously applying any of the methods disclosed herein for sequencing a nucleic acid to the plurality of different nucleic acids. In different embodiments, the method can be used to sequence from one to over 100,000 different nucleic acids simultaneously.

The invention provides for the use of any of the methods disclosed herein for detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

The invention provides a method of attaching a nucleic acid to a solid surface which comprises:
  (i) coating the solid surface with a phosphine moiety,
  (ii) attaching an azido group to a 5' end of the nucleic acid, and
  (iii) immobilizing the 5' end of the nucleic acid to the solid surface through interaction between the phosphine moiety on the solid surface and the azido group on the 5' end of the nucleic acid.

In one embodiment, the step of coating the solid surface with the phosphine moiety comprises:
  (i) coating the surface with a primary amine, and
  (ii) covalently coupling a N-hydroxysuccinimidyl ester of triarylphosphine with the primary amine.

In different embodiments, the solid surface is glass, silicon, or gold. In different embodiments, the solid surface is a magnetic bead, a chip, a channel in an chip, or a porous channel in a chip.

In different embodiments, the nucleic acid that is attached to the solid surface is a single-stranded or double-stranded DNA or a RNA. In one embodiment, the nucleic acid is a double-stranded DNA and only one strand is attached to the solid surface. In a further embodiment, the strand of the double-stranded DNA that is not attached to the solid surface is removed by denaturing.

The invention provides for the use of any of the methods disclosed herein for attaching a nucleic acid to a surface for gene expression analysis, microarray based gene expression analysis, or mutation detection, translational analysis, transcriptional analysis, or for other genetic applications.

The invention provides a nucleotide analogue which comprises:
  (a) a base selected from the group consisting of adenine or an analogue of adenine, cytosine or an analogue of cytosine, guanine or an analogue of guanine, thymine or an analogue of thymine, and uracil or an analogue of uracil;
  (b) a unique label attached through a cleavable linker to the base or to an analogue of the base;
  (c) a deoxyribose; and
  (d) a cleavable chemical group to cap an —OH group at a 3'-position of the deoxyribose.

In one embodiment of the nucleotide analogue, the cleavable chemical group that caps the —OH group at the 3'-position of the deoxyribose is —CH$_2$OCH$_3$ or —CH$_2$CH=CH$_2$.

In one embodiment, the unique label is a fluorescent moiety or a fluorescent semiconductor crystal. In further embodiments, the fluorescent moiety is selected from the group consisting of 5-carboxyfluorescein, 6-carboxyrhodamine-6G, N,N,N',N'-tetramethyl-6-carboxyrhodamine, and 6-carboxy-X-rhodamine.

In one embodiment, the unique label is a fluorescence energy transfer tag which comprises an energy transfer donor and an energy transfer acceptor. In further embodiments, the energy transfer donor is 5-carboxyfluorescein or cyanine, and wherein the energy transfer acceptor is selected from the group consisting of dichlorocarboxyfluorescein, dichloro-6-carboxyrhodamine-6G, dichloro-N,N,N',N'-tetramethyl-6-carboxyrhodamine, and dichloro-6-carboxy-X-rhodamine.

In one embodiment, the unique label is a mass tag that can be detected and differentiated by a mass spectrometer. In further embodiments, the mass tag is selected from the group consisting of a 2-nitro-α-methyl-benzyl group, a 2-nitro-α-methyl-3-fluorobenzyl group, a 2-nitro-α-methyl-3,4-difluorobenzyl group, and a 2-nitro-α-methyl-3,4-dimethoxybenzyl group.

In one embodiment, the unique label is attached through a cleavable linker to a 5-position of cytosine or thymine or to a 7-position of deaza-adenine or deaza-guanine. The unique label could also be attached through a cleavable linker to another position in the nucleotide analogue as long as the attachment of the label is stable during the polymerase reaction and the nucleotide analog can be recognized by polymerase as a substrate. For example, the cleavable label could be attached to the deoxyribose.

In one embodiment, the linker between the unique label and the nucleotide analogue is cleavable by a means selected from the group consisting of one or more of a physical means, a chemical means, a physical chemical means, heat, and light. In a further embodiment, the cleavable linker is a photocleavable linker which comprises a 2-nitrobenzyl moiety.

In one embodiment, the cleavable chemical group used to cap the —OH group at the 3'-position of the deoxyribose is cleavable by a means selected from the group consisting of one or more of a physical means, a chemical means, a physical chemical means, heat, and light.

In different embodiments, the nucleotide analogue is selected from the group consisting of:

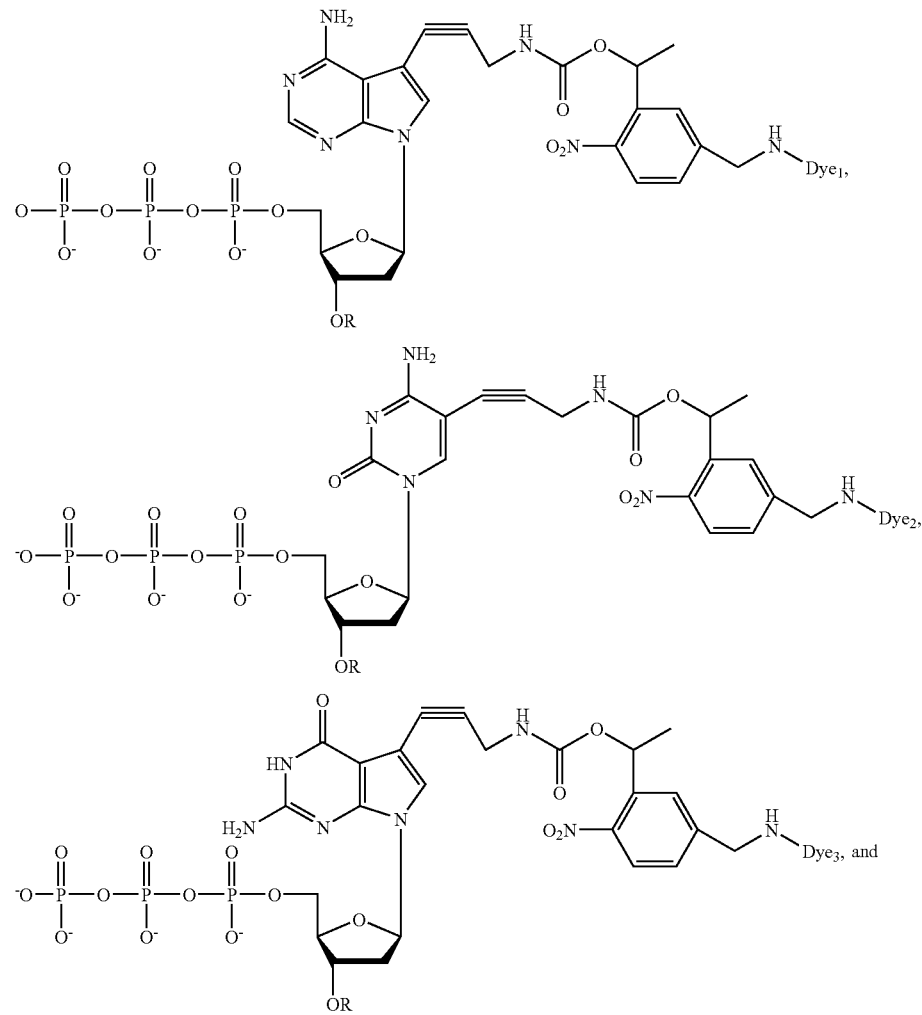

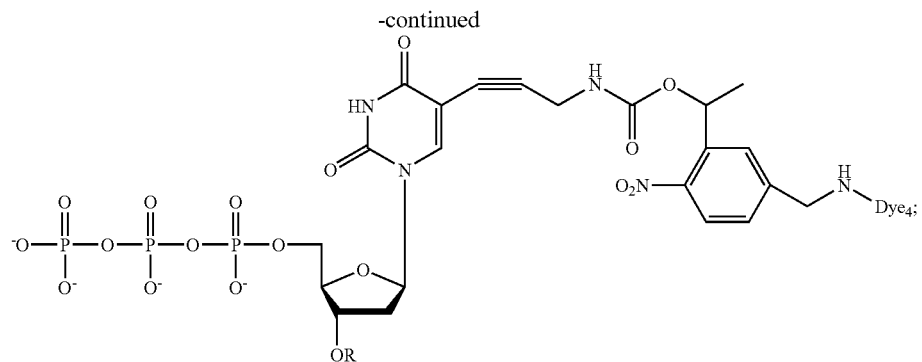
wherein Dye$_1$, Dye$_2$, Dye$_3$, and Dye$_4$ are four different unique labels; and
wherein R is a cleavable chemical group used to cap the —OH group at the 3'-position of the deoxyribose.
In different embodiments, the nucleotide analogue is selected from the group consisting of:
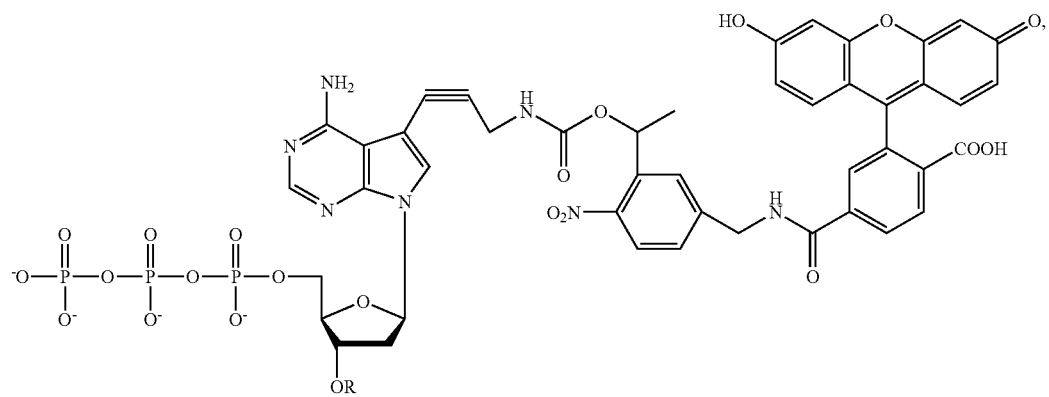
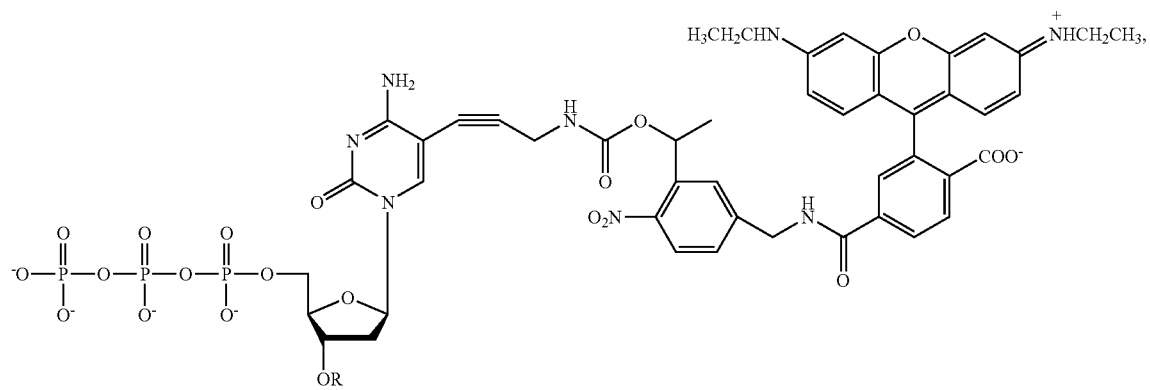

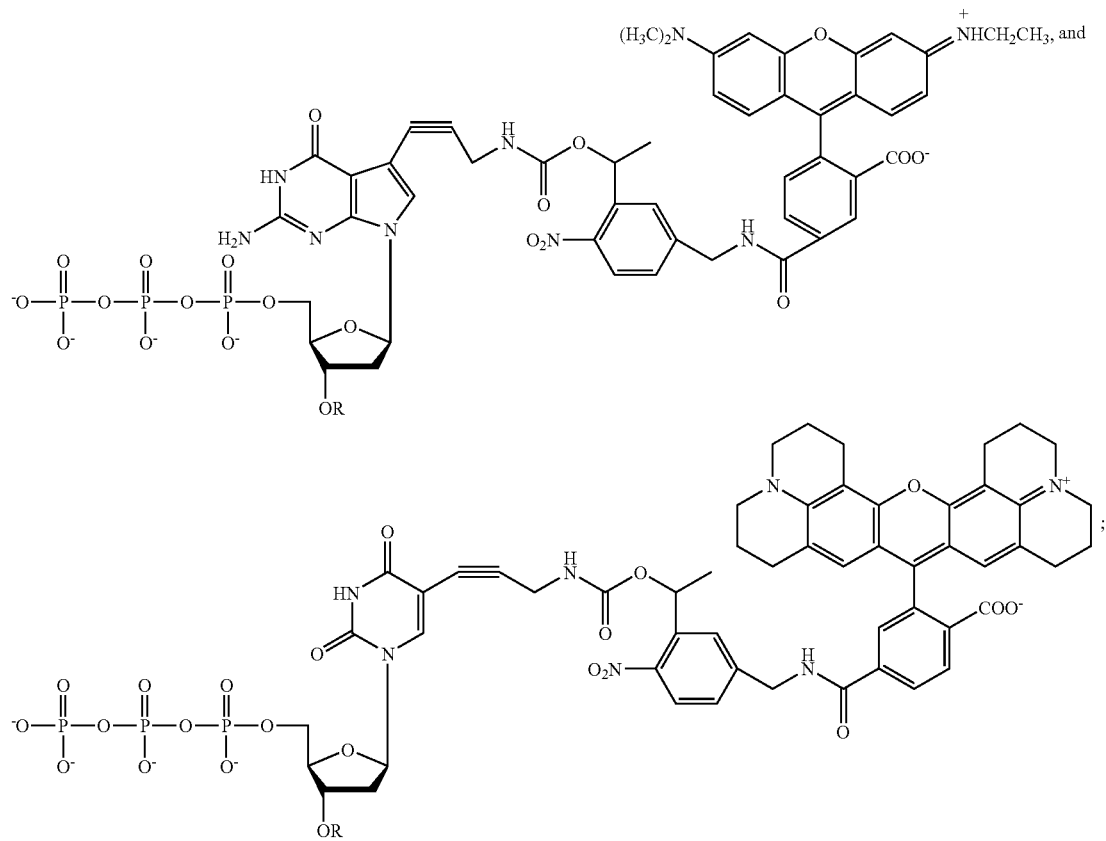
wherein R is —CH$_2$OCH$_3$ or —CH$_2$CH=CH$_2$.
In different embodiments, the nucleotide analogue is selected from the group consisting of:
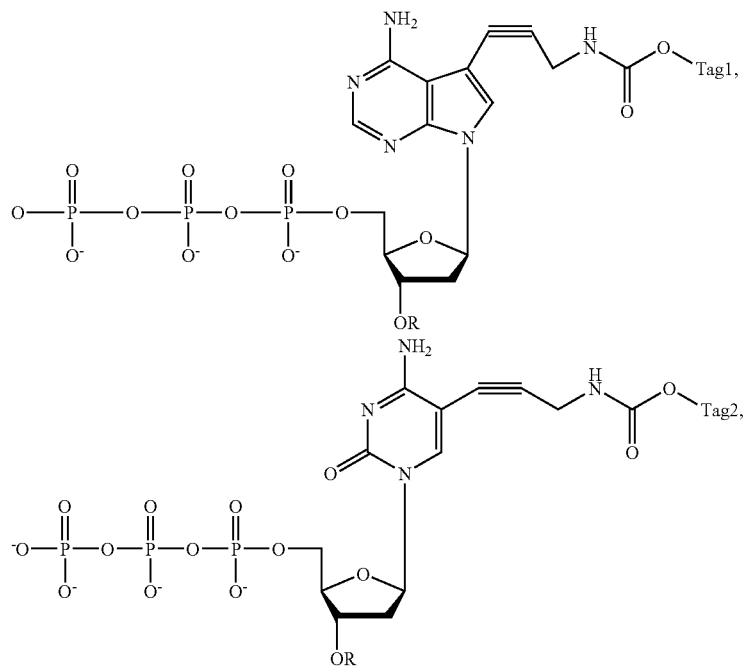

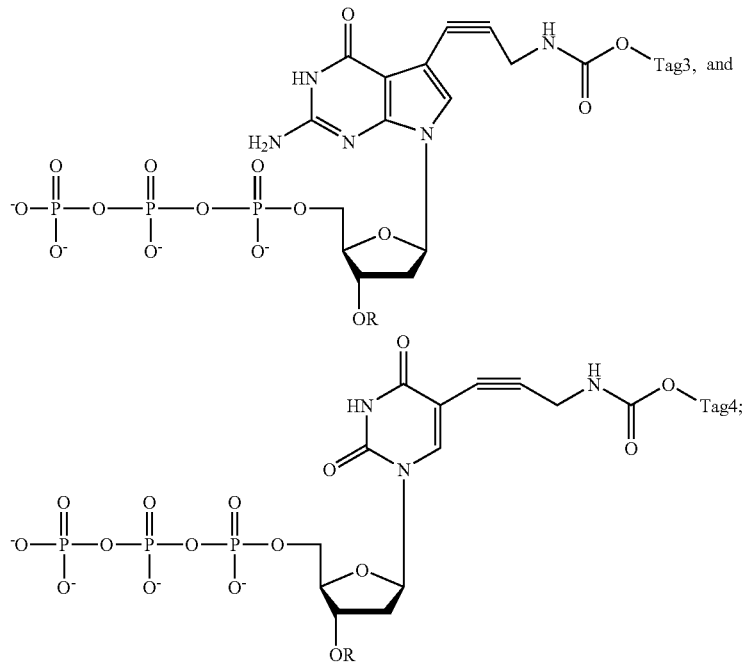
wherein Tag$_1$, Tag$_2$, Tag$_3$, and Tag$_4$ are four different mass tag labels; and
wherein R is a cleavable chemical group used to cap the —OH group at the 3'-position of the deoxyribose.
In different embodiments, the nucleotide analogue is selected from the group consisting of:
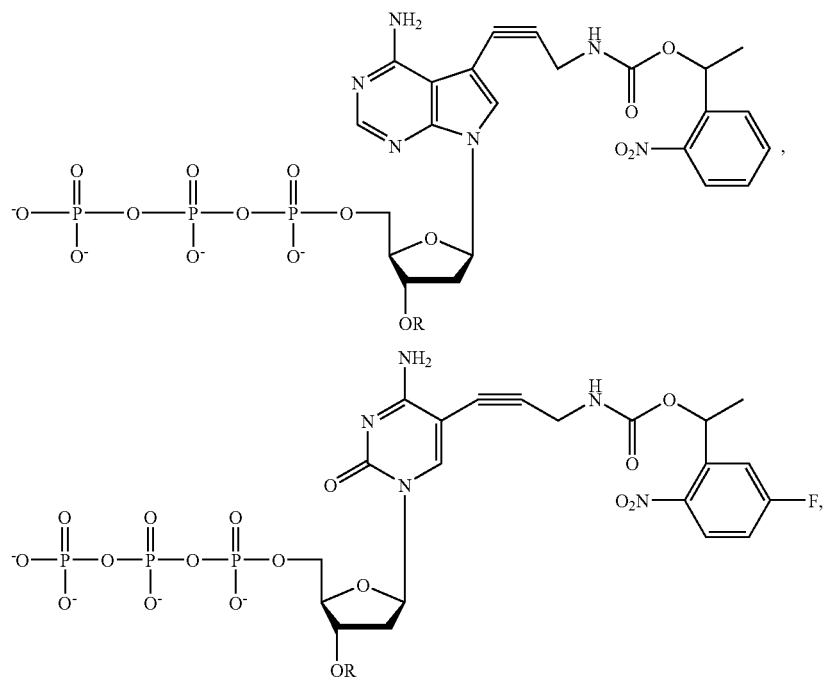

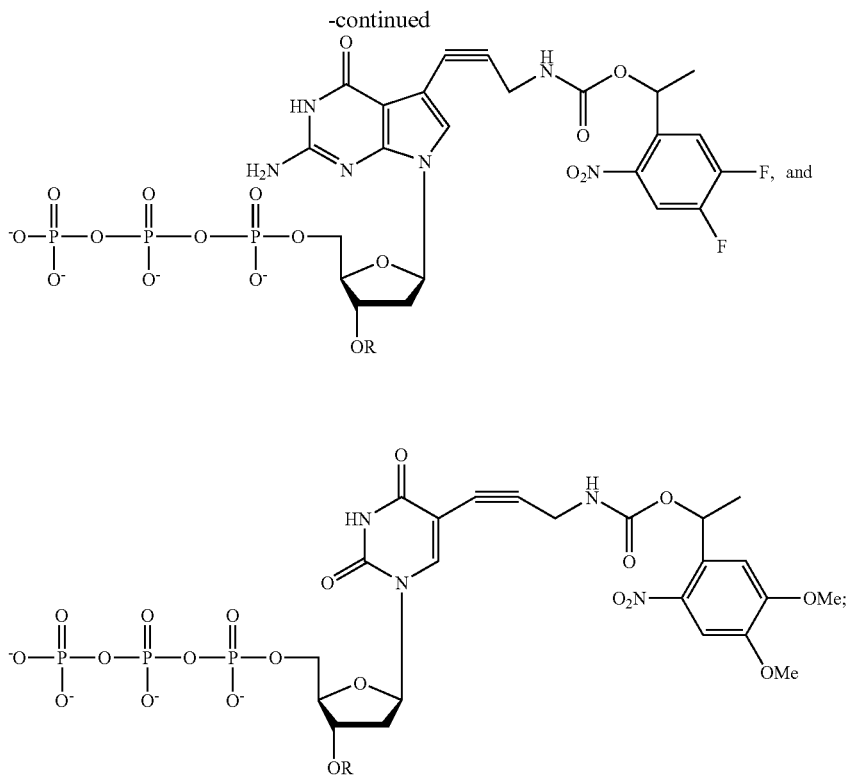

wherein R is —CH$_2$OCH$_3$ or —CH$_2$CH=CH$_2$.

The invention provides for the use any of the nucleotide analogues disclosed herein for detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

The invention provides a parallel mass spectrometry system, which comprises a plurality of atmospheric pressure chemical ionization mass spectrometers for parallel analysis of a plurality of samples comprising mass tags. In one embodiment, the mass spectrometers are quadrupole mass spectrometers. In one embodiment, the mass spectrometers are time-of-flight mass spectrometers. In one embodiment, the mass spectrometers are contained in one device. In one embodiment, the system further comprises two turbopumps, wherein one pump is used to generate a vacuum and a second pump is used to remove undesired elements. In one embodiment, the system comprises at least three mass spectrometers. In one embodiment, the mass tags have molecular weights between 150 daltons and 250 daltons. The invention provides for the use of the system for DNA sequencing analysis, detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

This invention will be better understood from the Experimental Details which follow. However, one skilled in the art will readily appreciate that the specific methods and results discussed are merely illustrative of the invention as described more fully in the claims which follow thereafter.

Experimental Details

1. The Sequencing by Synthesis Approach

Sequencing DNA by synthesis involves the detection of the identity of each nucleotide as it is incorporated into the growing strand of DNA in the polymerase reaction. The fundamental requirements for such a system to work are: (1) the availability of 4 nucleotide analogues (aA, aC, aG, aT) each labeled with a unique label and containing a chemical moiety capping the 3'-OH group; (2) the 4 nucleotide analogues (aA, aC, aG, aT) need to be efficiently and faithfully incorporated by DNA polymerase as terminators in the polymerase reaction; (3) the tag and the group capping the 3'-OH need to be removed with high yield to allow the incorporation and detection of the next nucleotide; and (4) the growing strand of DNA should survive the washing, detection and cleavage processes to remain annealed to the DNA template.

Figure 2A:
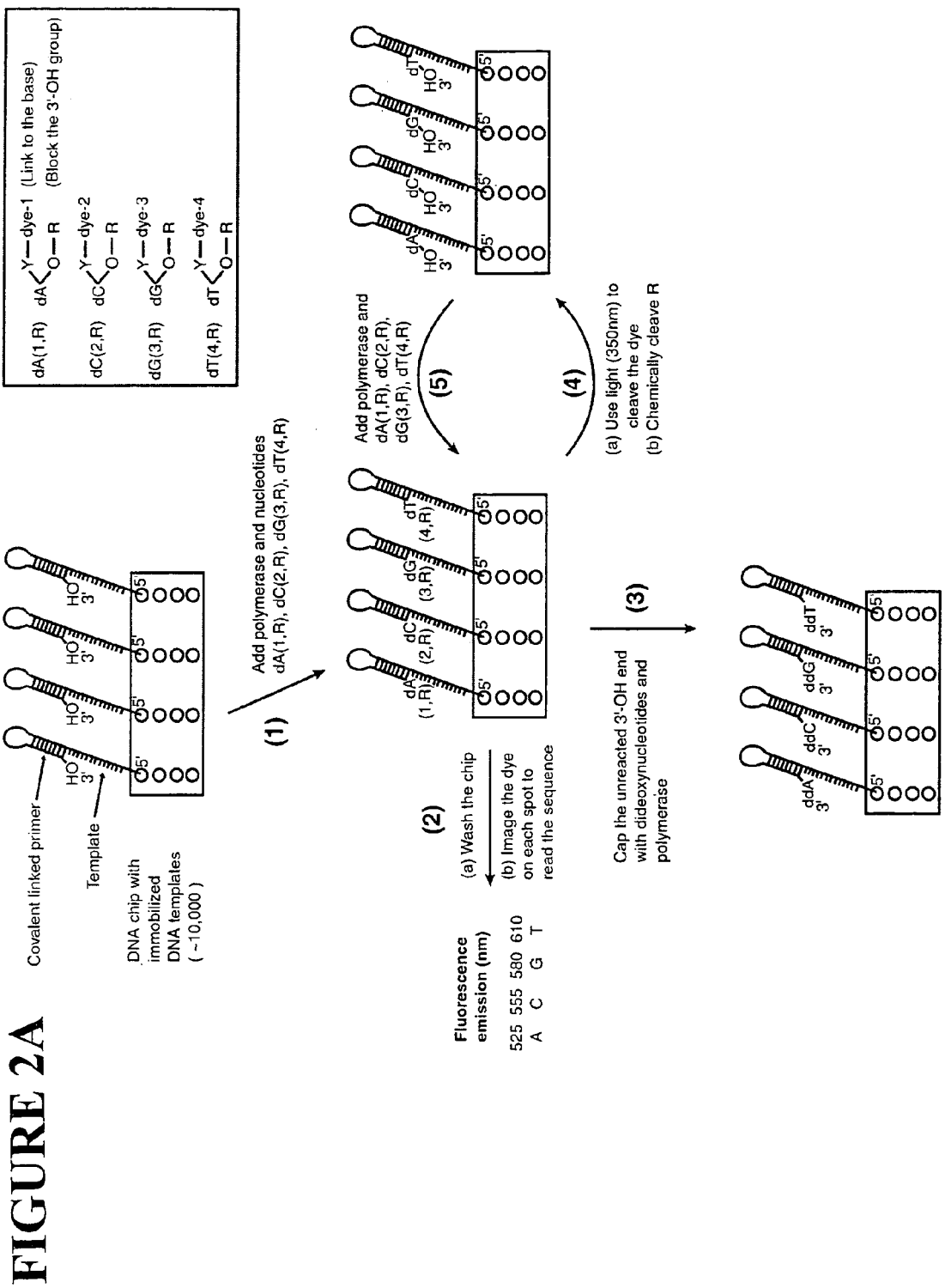
FIGS. 2A-2B: Scheme of sequencing by the synthesis approach. A: Example where the unique labels are dyes and the solid surface is a chip. B: Example where the unique labels are mass tags and the solid surface is channels etched into a glass chip. A, C, G, T; nucleotide triphosphates comprising bases adenine, cytosine, guanine, and thymine; d, deoxy; dd, dideoxy; R, cleavable chemical group used to cap the —OH group; Y, cleavable linker.
Figure 2B:
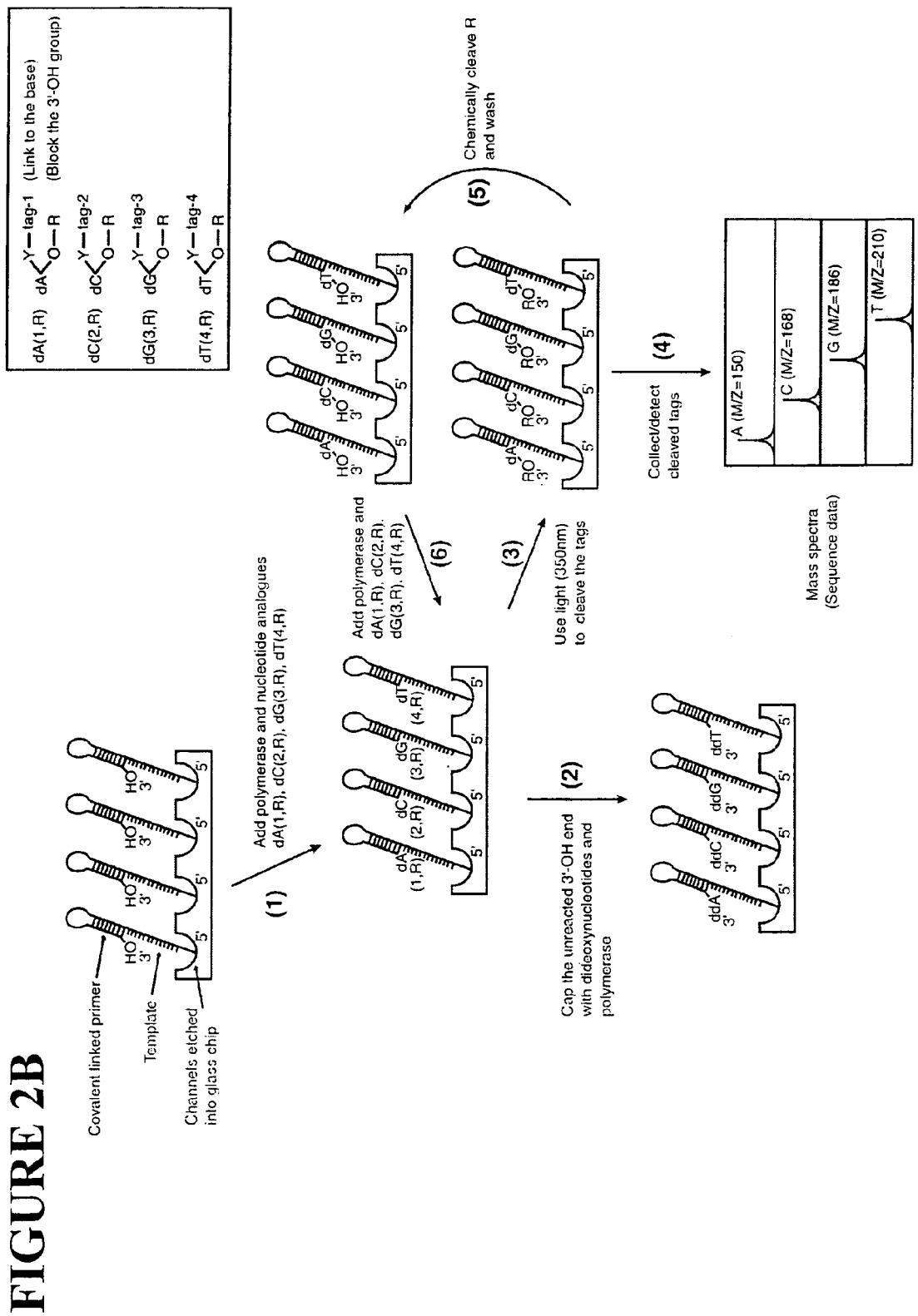

The sequencing by synthesis approach disclosed herein is illustrated in FIGS. 2A-2B. In FIG. 2A, an example is shown where the unique labels are fluorescent dyes and the surface is a chip; in FIG. 2B, the unique labels are mass tags and the surface is channels etched into a chip. The synthesis approach uses a solid surface such as a glass chip with an immobilized DNA template that is able to self prime for initiating the polymerase reaction, and four nucleotide analogues ($3'$-$RO$-A-$LABEL1$, $3'$-$RO$-C-$LABEL2$, $3'$-$RO$-G-$LABEL3$, $3'$-$RO$-T-$LABEL4$) each labeled with a unique label, e.g. a fluorescent dye or a mass tag, at a specific location on the purine or pyrimidine base, and a small cleavable chemical group (R) to cap the 3'-OH group. Upon adding the four nucleotide analogues and DNA polymerase, only one nucleotide analogue that is complementary to the next nucleotide on the template is incorporated by the polymerase on each spot of the surface (step 1 in FIGS. 2A and 2B).

As shown in FIG. 2A, where the unique labels are dyes, after removing the excess reagents and washing away any unincorporated nucleotide analogues on the chip, a detector is used to detect the unique label. For example, a four color fluorescence imager is used to image the surface of the chip, and the unique fluorescence emission from a specific dye on the nucleotide analogues on each spot of the chip will reveal the identity of the incorporated nucleotide (step 2 in FIG. 2A). After imaging, the small amount of unreacted 3'-OH group on the self-primed template moiety is capped by excess dideoxynucleoside triphosphates (ddNTPs) (ddATP, ddGTP, ddTTP, and ddCTP) and DNA polymerase to avoid interference with the next round of synthesis (step 3 in FIG. 2A), a concept similar to the capping step in automated solid phase DNA synthesis (Caruthers, 1985). The ddNTPs, which lack a 3'-hydroxyl group, are chosen to cap the unreacted 3'-OH of the nucleotide due to their small size compared with the dye-labeled nucleotides, and the excellent efficiency with which they are incorporated by DNA polymerase. The dye moiety is then cleaved by light (~350 nm), and the R group protecting the 3'-OH is removed chemically to generate free 3'-OH group with high yield (step 4 in FIG. 2A). A washing step is applied to wash away the cleaved dyes and the R group. The self-primed DNA moiety on the chip at this stage is ready for the next cycle of the reaction to identify the next nucleotide sequence of the template DNA (step 5 in FIG. 2A).

It is a routine procedure now to immobilize high density (>10,000 spots per chip) single stranded DNA on a 4 cm×1 cm glass chip (Schena et al. 1995). Thus, in the DNA sequencing system disclosed herein, more than 10,000 bases can be identified after each cycle and after 100 cycles, a million base pairs will be generated from one sequencing chip.

Possible DNA polymerases include Thermo Sequenase, Taq FS DNA polymerase, T7 DNA polymerase, and Vent (exo-) DNA polymerase. The fluorescence emission from each specific dye can be detected using a fluorimeter that is equipped with an accessory to detect fluorescence from a glass slide. For large scale evaluation, a multi-color scanning system capable of detecting multiple different fluorescent dyes (500 nm-700 nm) (GSI Lumonics ScanArray 5000 Standard Biochip Scanning System) on a glass slide can be used.

An example of the sequencing by synthesis approach using mass tags is shown in FIG. 2B. The approach uses a solid surface, such as a porous silica glass channels in a chip, with immobilized DNA template that is able to self prime for initiating the polymerase reaction, and four nucleotide analogues ($3'_{-RO}$-A-$_{Tag1}$, $3'_{-RO}$-C-$_{Tag2}$, $3'_{-RO}$-G-$_{Tag3}$, $3'_{-RO}$-T-$_{Tag4}$) each labeled with a unique photocleavable mass tag on the specific location of the base, and a small cleavable chemical group (R) to cap the 3'-OH group. Upon adding the four nucleotide analogues and DNA polymerase, only one nucleotide analogue that is complementary to the next nucleotide on the template is incorporated by polymerase in each channel of the glass chip (step 1 in FIG. 2B). After removing the excess reagents and washing away any unincorporated nucleotide analogues on the chip, the small amount of unreacted 3'-OH group on the self-primed template moiety is capped by excess ddNTPs (ddATP, ddGTP, ddTTP and ddCTP) and DNA polymerase to avoid interference with the next round of synthesis (step 2 in FIG. 2B). The ddNTPs are chosen to cap the unreacted 3'-OH of the nucleotide due to their small size compared with the labeled nucleotides, and their excellent efficiency to be incorporated by DNA polymerase. The mass tags are cleaved by irradiation with light (~350 nm) (step 3 in FIG. 2B) and then detected with a mass spectrometer. The unique mass of each tag yields the identity of the nucleotide in each channel (step 4 in FIG. 2B). The R protecting group is then removed chemically and washed away to generate free 3'-OH group with high yield (step 5 in FIG. 2B). The self-primed DNA moiety on the chip at this stage is ready for the next cycle of the reaction to identify the next nucleotide sequence of the template DNA (step 6 in FIG. 2B).

Since the development of new ionization techniques such as matrix assisted laser desorption ionization (MALDI) and electrospray ionization (ESI), mass spectrometry has become an indispensable tool in many areas of biomedical research. Though these ionization methods are suitable for the analysis of bioorganic molecules, such as peptides and proteins, improvements in both detection and sample preparation are required for implementation of mass spectrometry for DNA sequencing applications. Since the approach disclosed herein uses small and stable mass tags, there is no need to detect large DNA sequencing fragments directly and it is not necessary to use MALDI or ESI methods for detection. Atmospheric pressure chemical ionization (APCI) is an ionization method that uses a gas-phase ion-molecular reaction at atmospheric pressure (Dizidic et al. 1975). In this method, samples are introduced by either chromatography or flow injection into a pneumatic nebulizer where they are converted into small droplets by a high-speed beam of nitrogen gas. When the heated gas and solution arrive at the reaction area, the excess amount of solvent is ionized by corona discharge. This ionized mobile phase acts as the ionizing agent toward the samples and yields pseudo molecular $(M+H)^+$ and $(M-H)^-$ ions. Due to the corona discharge ionization method, high ionization efficiency is attainable, maintaining stable ionization conditions with detection sensitivity lower than femtomole region for small and stable organic compounds. However, due to the limited detection of large molecules, ESI and MALDI have replaced APCI for analysis of peptides and nucleic acids. Since in the approach disclosed the mass tags to be detected are relatively small and very stable organic molecules, the ability to detect large biological molecules gained by using ESI and MALDI is not necessary. APCI has several advantages over ESI and MALDI because it does not require any tedious sample preparation such as desalting or mixing with matrix to prepare crystals on a target plate. In ESI, the sample nature and sample preparation conditions (i.e. the existence of buffer or inorganic salts) suppress the ionization efficiency. MALDI requires the addition of matrix prior to sample introduction into the mass spectrometer and its speed is often limited by the need to search for an ideal irradiation spot to obtain interpretable mass spectra. These limitations are overcome by APCI because the mass tag solution can be injected directly with no additional sample purification or preparation into the mass spectrometer. Since the mass tagged samples are volatile and have small mass numbers, these compounds are easily detectable by APCI ionization with high sensitivity. This system can be scaled up into a high throughput operation.

Each component of the sequencing by synthesis system is described in more detail below.

2. Construction of a Surface Containing Immobilized Self-primed DNA Moiety

Figure 3:
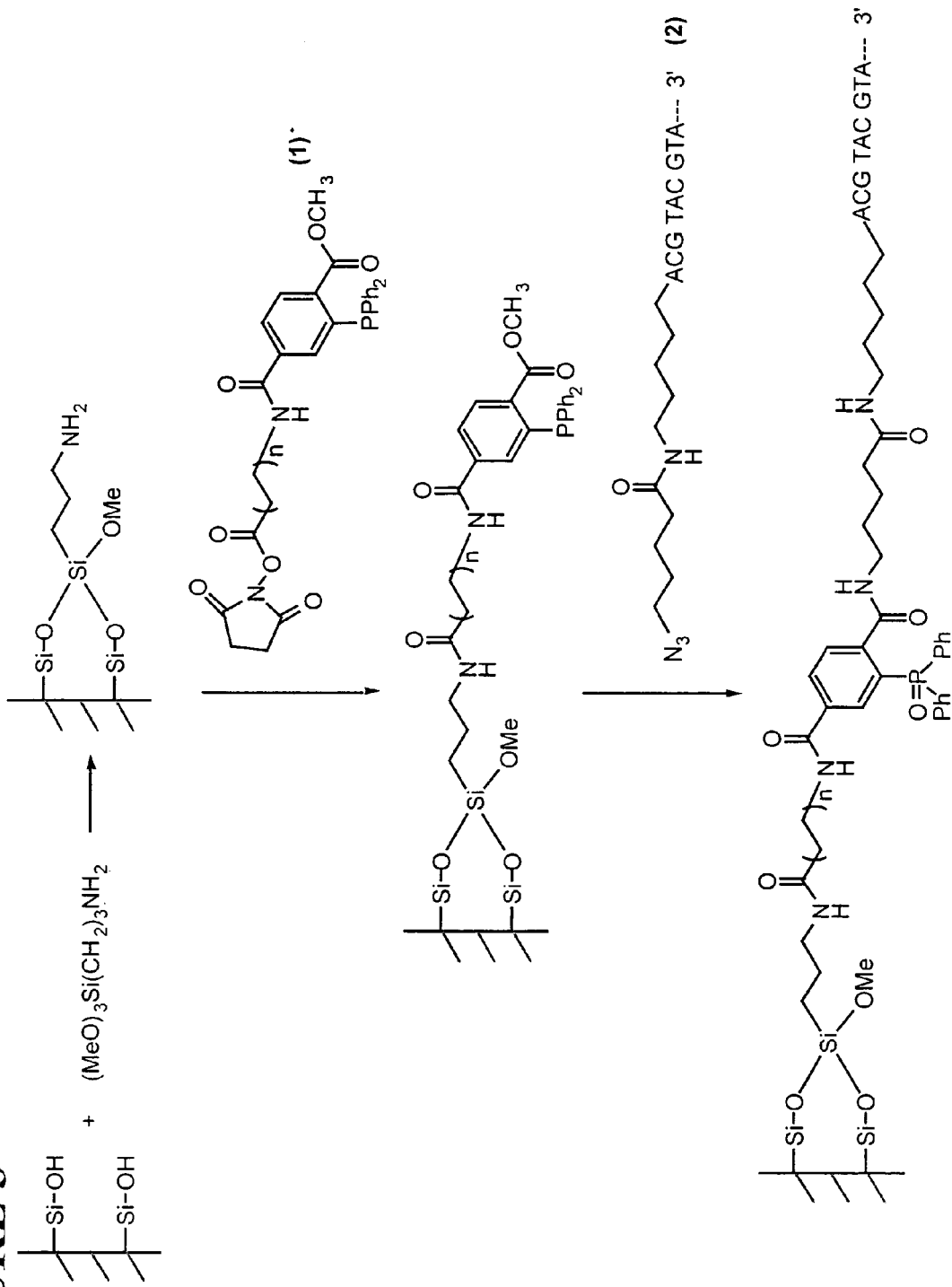
FIG. 3: The synthetic scheme for the immobilization of an azido ($N_3$) labeled DNA fragment to a solid surface coated with a triarylphosphine moiety. Me, methyl group; P, phosphorus; Ph, phenyl.

The single stranded DNA template immobilized on a surface is prepared according to the scheme shown in FIG. 3. The surface can be, for example, a glass chip, such as a 4 cm×1 cm glass chip, or channels in a glass chip. The surface is first treated with 0.5 M NaOH, washed with water, and then coated with high density 3-aminopropyltrimethoxysilane in aqueous ethanol (Woolley et al. 1994) forming a primary amine surface. N-Hydroxy Succinimidyl (NHS) ester of triarylphosphine (1) is covalently coupled with the primary amine group converting the amine surface to a novel triarylphosphine surface, which specifically reacts with DNA containing an azido group (2) forming a chip with immobilized DNA. Since the azido group is only located at the 5' end of the DNA and the coupling reaction is through the unique reaction of the triaryiphosphine moiety with the azido group in aqueous solution (Saxon and Bertozzi 2000), such a DNA surface will provide an optimal condition for hybridization.

Figure 4:
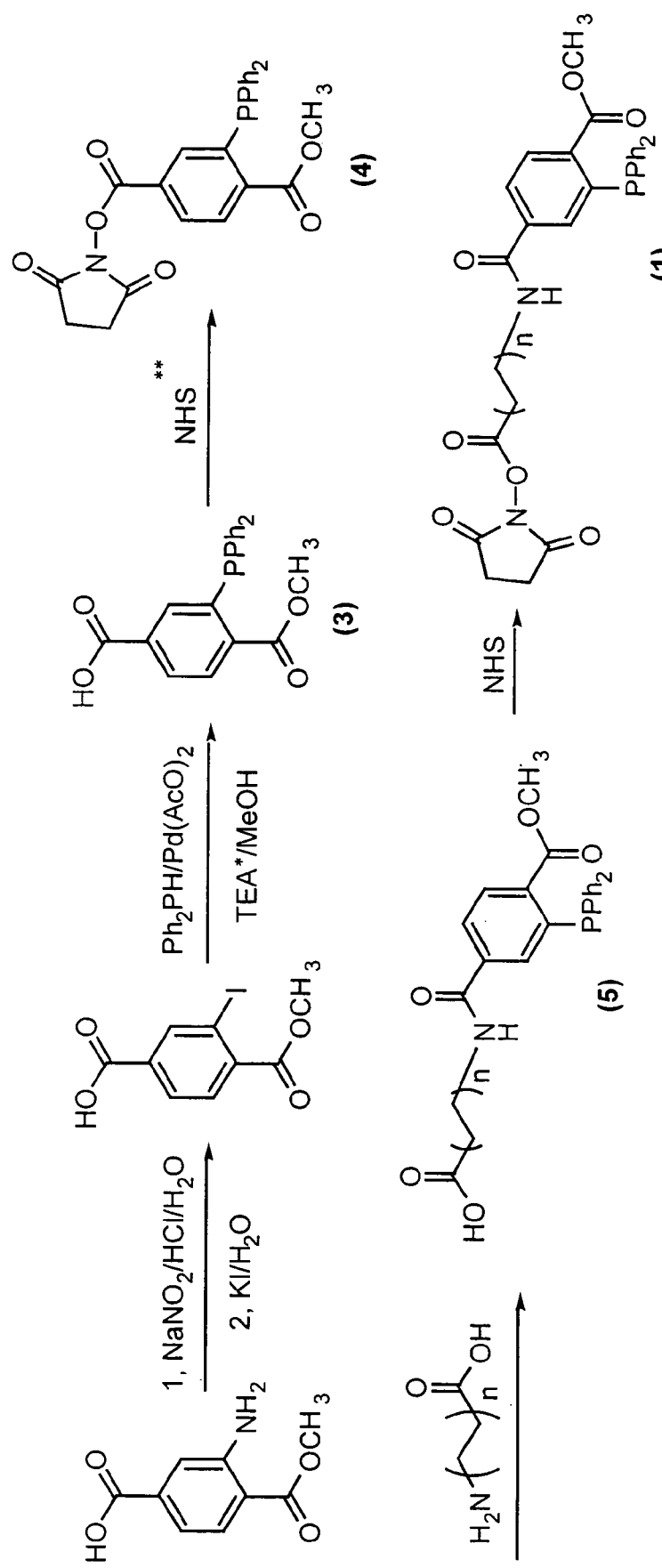
FIG. 4: The synthesis of triarylphosphine N-hydroxysuccinimide (NHS) ester.

The NHS ester of triarylphosphine (1) is prepared according to the scheme shown in FIG. 4. 3-diphenylphosphino-4-methoxycarbonyl-benzoic acid (3) is prepared according to the procedure described by Bertozzi et al. (Saxon and Bertozzi 2000). Treatment of (3) with N-Hydroxysuccinimide forms the corresponding NHS ester (4). Coupling of (4) with an amino carboxylic acid moiety produces compound (5) that has a long linker (n=1 to 10) for optimized coupling with DNA on the surface. Treatment of (5) with N-Hydroxysuccinimide generates the NHS ester (1) which is ready for coupling with the primary amine coated surface (FIG. 3).

Figure 5:
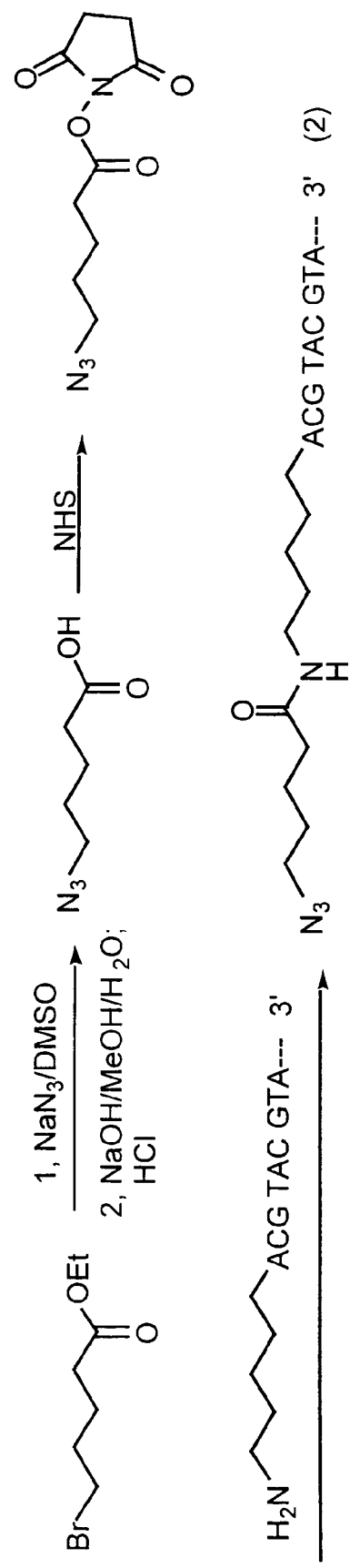
FIG. 5: The synthetic scheme for attaching an azido ($N_3$) group through a linker to the 5' end of a DNA fragment, which is then used to couple with the triarylphosphine moiety on a solid surface. DMSO, dimethylsulfonyl oxide.

The azido labeled DNA (2) is synthesized according to the scheme shown in FIG. 5. Treatment of ethyl ester of 5-bromovaleric acid with sodium azide and then hydrolysis produces 5-azidovaleric acid (Khoukhi et al., 1987), which is subsequently converted to a NHS ester for coupling with an amino linker modified oligonucleotide primer. Using the azido-labeled primer to perform polymerase chain reaction (PCR) reaction generates azido-labeled DNA template (2) for coupling with the triarylphosphine-modified surface (FIG. 3).

Figure 6A:
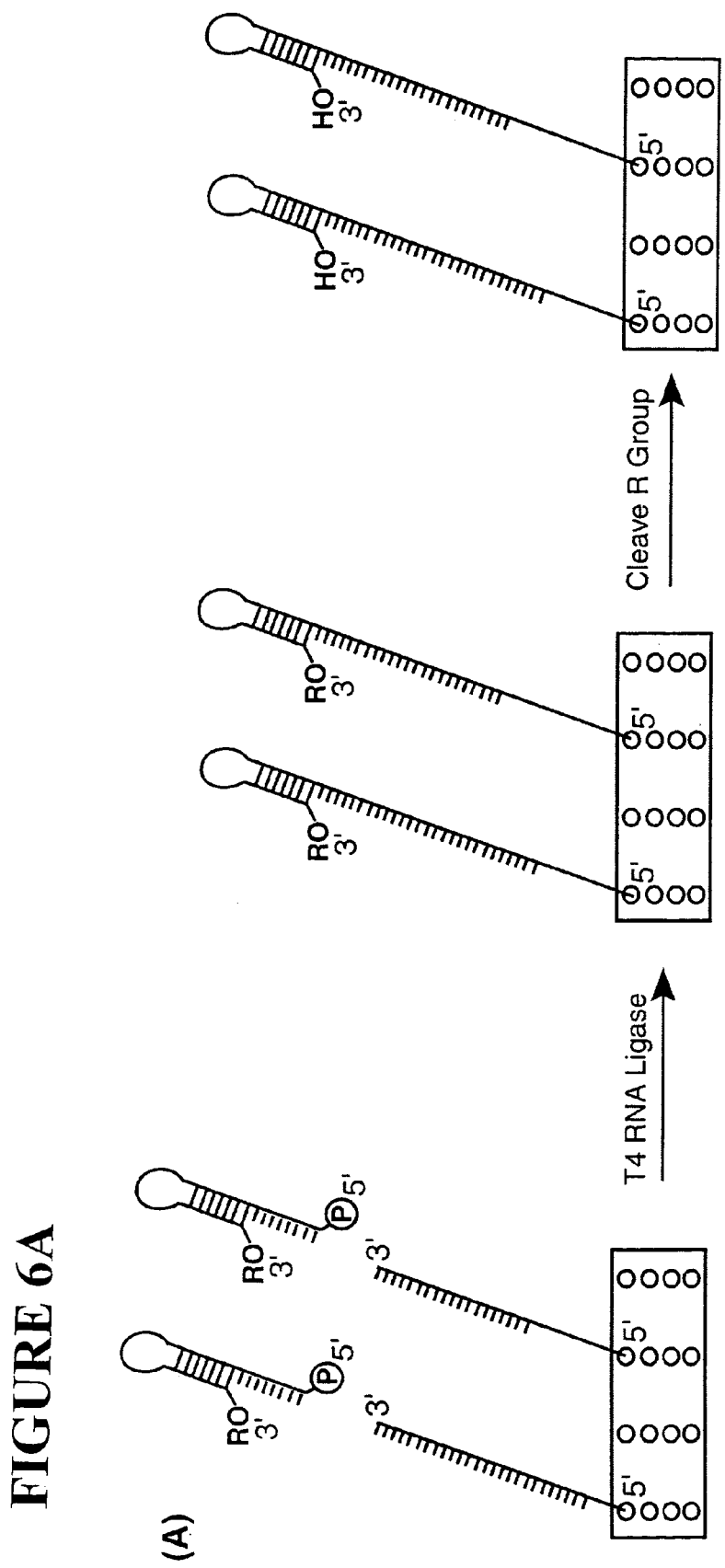
FIGS. 6A-6B: Ligate the looped primer (B) to the immobilized single stranded DNA template forming a self primed DNA template moiety on a solid surface. P (in circle), phosphate.
Figure 6B:
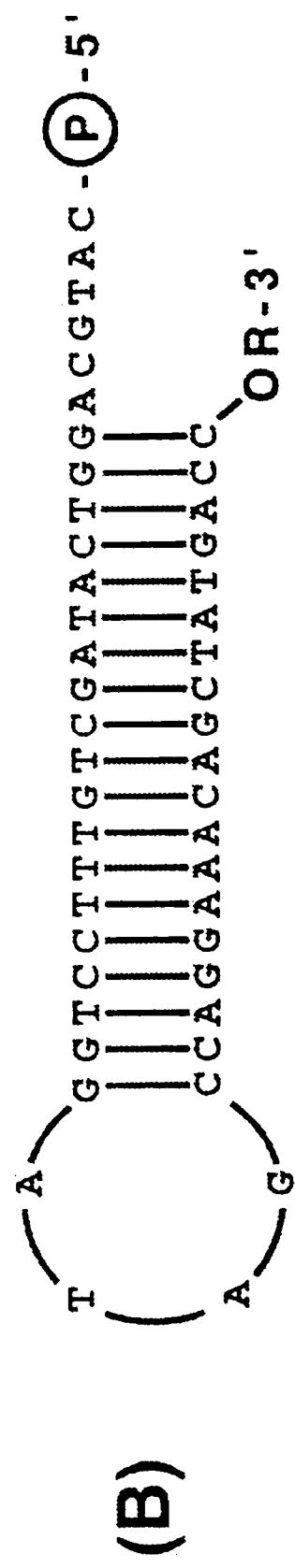

The self-primed DNA template moiety on the sequencing chip is constructed as shown in FIGS. 6(A & B) using enzymatic ligation. A 5'-phosphorylated, 3'-OH capped loop oligonucleotide primer (B) is synthesized by a solid phase DNA synthesizer. Primer (B) is synthesized using a modified C phosphoramidite whose 3'-OH is capped with either a MOM (—$CH_2OCH_3$) group or an allyl (—$CH_2CH$=$CH_2$) group (designated by "R" in FIG. 6) at the 3'-end of the oligonucleotide to prevent the self ligation of the primer in the ligation reaction. Thus, the looped primer can only ligate to the 3'-end of the DNA templates that are immobilized on the sequencing chip using T4 RNA ligase (Zhang et al. 1996) to form the self-primed DNA template moiety (A). The looped primer (B) is designed to contain a very stable loop (Antao et al. 1991) and a stem containing the sequence of M13 reverse DNA sequencing primer for efficient priming in the polymerase reaction once the primer is ligated to the immobilized DNA on the sequencing chip and the 3'-OH cap group is chemically cleaved off (Ireland et al. 1986; Kamal et al. 1999).

Figure 7:
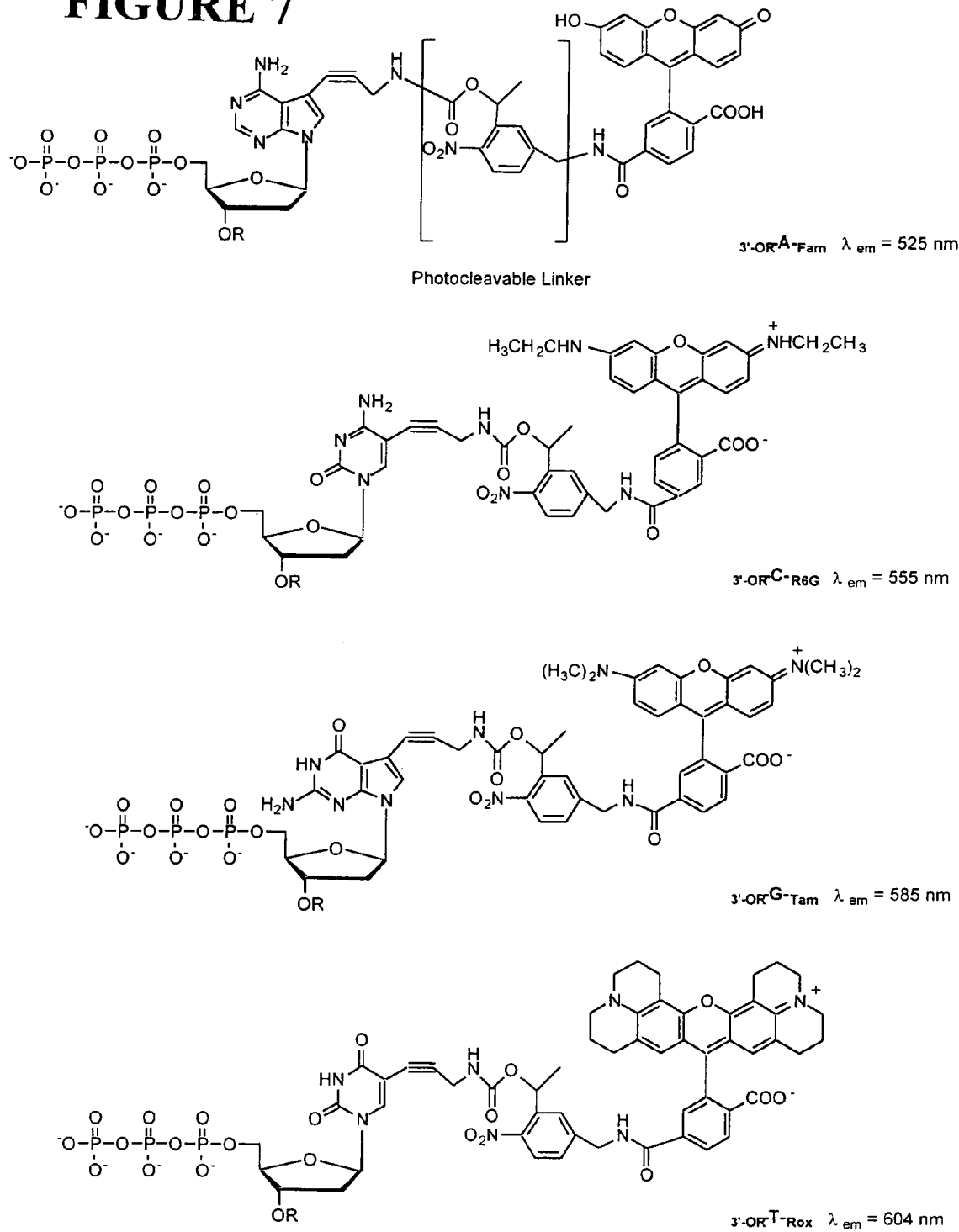
FIG. 7: Examples of structures of four nucleotide analogues for use in the sequencing by synthesis approach. Each nucleotide analogue has a unique fluorescent dye attached to the base through a photocleavable linker and the 3'-OH is either exposed or capped with a MOM group or an allyl group. FAM, 5-carboxyfluorescein; R6G, 6-carboxyrhodamine-6G; TAM, N,N,N',N'-tetramethyl-6-carboxyrhodamine; ROX, 6-carboxy-X-rhodamine. R=H, $CH_2OCH_3$ (MOM) or $CH_2CH=CH_2$ (Allyl).

3. Sequencing by Synthesis Evaluation Using Nucleotide Analogues $_{3'-HO}$-A-$_{Dye1}$, $_{3'-HO}$-C-$_{Dye2}$, $_{3'-HO}$-G-$_{Dye3}$, $_{3'-HO}$-T-$_{Dye4}$ A scheme has been developed for evaluating the photocleavage efficiency using different dyes and testing the sequencing by synthesis approach. Four nucleotide analogues $_{3'-HO}$-A-$_{Dye1}$, $_{3'-HO}$-C-$_{Dye2}$, $_{3'-HO}$-G-$_{Dye3}$, $_{3'-HO}$-T-$_{Dye4}$ each labeled with a unique fluorescent dye through a photocleavable linker are synthesized and used in the sequencing by synthesis approach. Examples of dyes include, but are not limited to: Dye1=FAM, 5-carboxyfluorescein; Dye2=R6G, 6-carboxyrhodamine-6G; Dye3=TAM, N,N,N',N'-tetramethyl-6-carboxyrhodamine; and Dye4=ROX, 6-carboxy-X-rhodamine. The structures of the 4 nucleotide analogues are shown in FIG. 7. (R=H.

The photocleavable 2-nitrobenzyl moiety has been used to link biotin to DNA and protein for efficient removal by UV light (~350 nm) (Olejnik et al. 1995, 1999). In the approach disclosed herein the 2-nitrobenzyl group is used to bridge the fluorescent dye and nucleotide together to form the dye labeled nucleotides as shown in FIG. 7.

Figure 8:
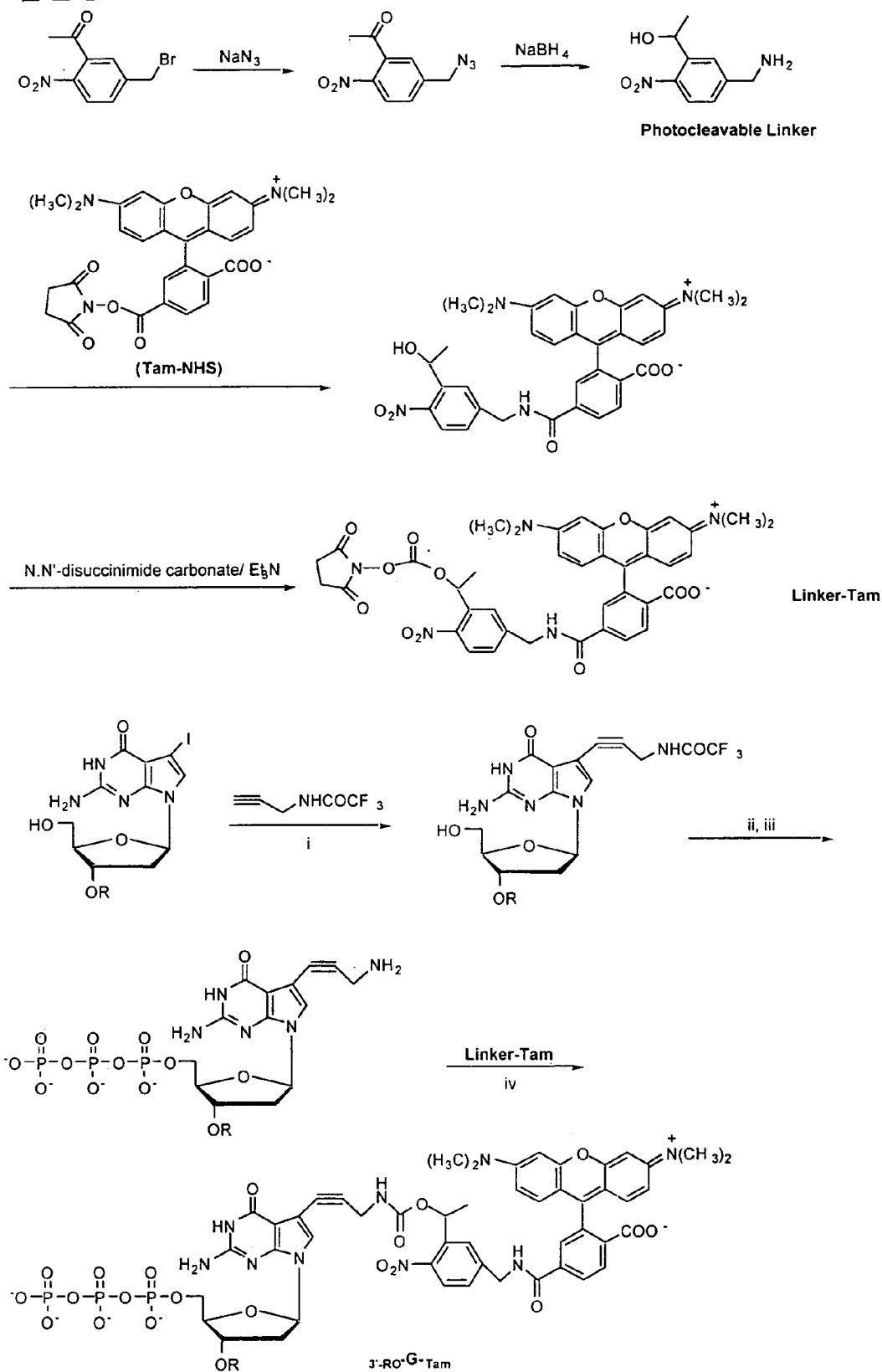
FIG. 8: A representative scheme for the synthesis of the nucleotide analogue $_{3'-RO}$-G-$_{Tam}$. A similar scheme can be used to create the other three modified nucleotides: $_{3'-RO}$-A-$_{Dye1}$, $_{3'-RO}$-C-$_{Dye2}$, $_{3'-RO}$-T-$_{Dye4}$. (i) tetrakis(triphenylphosphine)palladium(0); (ii) $POCl_3$, $Bn_4N^+$pyrophosphate; (iii) $NH_4OH$; (iv) $Na_2CO_3/NaHCO_3$ (pH=9.0)/DMSO.

As a representative example, the synthesis of $_{3'-HO}$-G-$_{Dye}$3 (Dye3=Tam) is shown in FIG. 8. 7-deaza-alkynylamino-dGTP is prepared using well-established procedures (Prober et al. 1987; Lee et al. 1992 and Hobbs et al. 1991). Linker-Tam is synthesized by coupling the Photocleavable Linker (Rollaf 1982) with NHS-Tam. 7-deaza-alkynylamino-dGTP is then coupled with the Linker-Tam to produce $_{3'-HO}$-G-$_{TAM}$. The nucleotide analogues with a free 3'-OH (i.e., R=H) are good substrates for the polymerase. An immobilized DNA template is synthesized (FIG. 9) that contains a portion of nucleotide sequence ACGTACGACGT (SEQ ID NO: 1) that has no repeated sequences after the priming site. $_{3'-HO}$-A-$_{Dye1}$ and DNA polymerase are added to the self-primed DNA moiety and it is incorporated to the 3' site of the DNA. Then the steps in FIG. 2A are followed (the chemical cleavage step is not required here because the 3'-OH is free) to detect the fluorescent signal from Dye-1 at 520 nm. Next, $_{3'-HO}$-C-$_{Dye2}$ is added to image the fluorescent signal from Dye-2 at 550 nm. Next, $_{3'-HO}$-G-$_{Dye3}$ is added to image the fluorescent signal from Dye-3 at 580 nm, and finally $_{3'-HO}$-T-$_{Dye4}$ is added to image the fluorescent signal from Dye-4 at 610 nm.

Results on Photochemical Cleavage Efficiency

Figure 10:
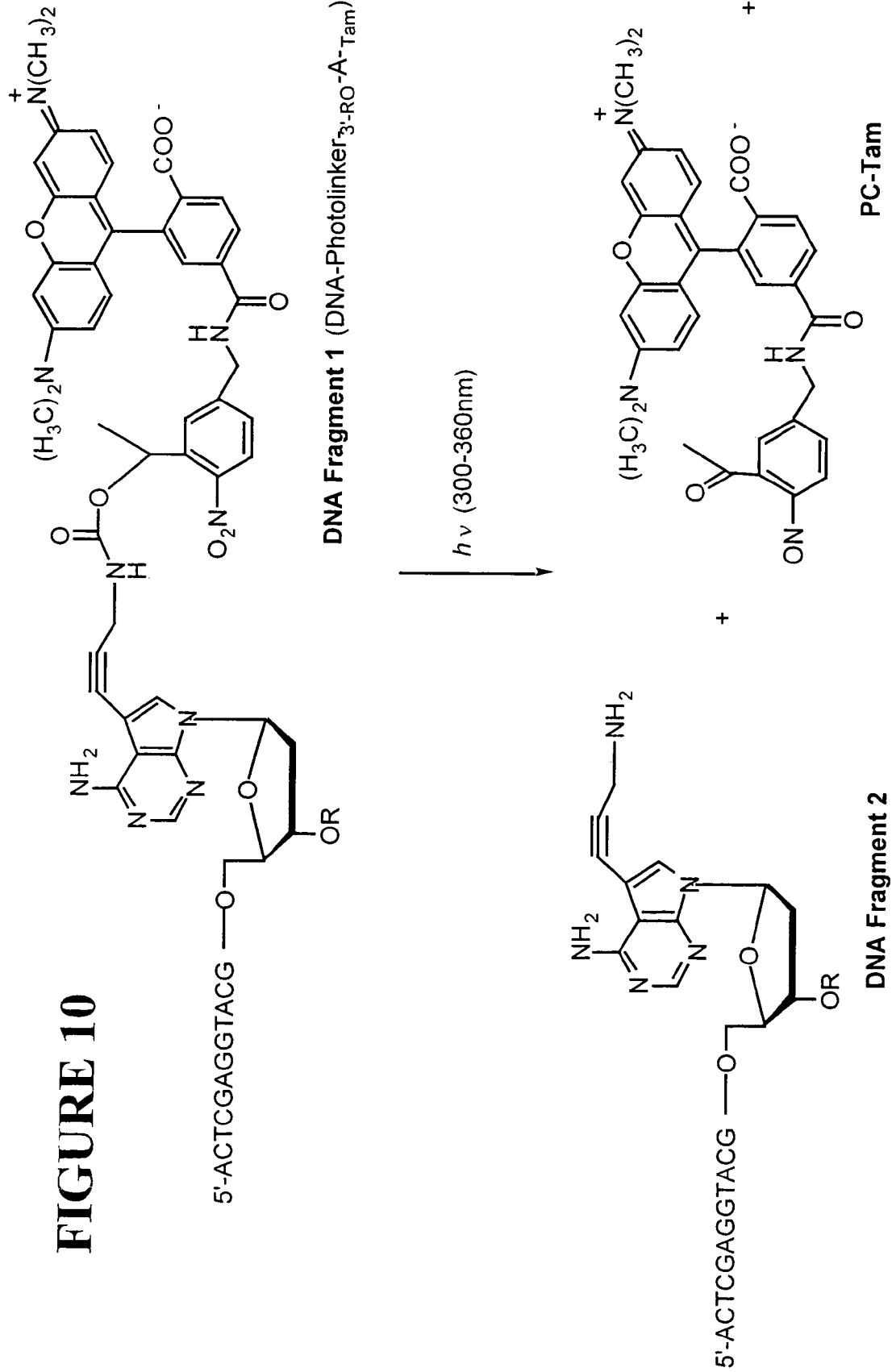
FIG. 10: The expected photocleavage products of DNA containing a photo-cleavable dye (Tam). Light absorption (300-360 nm) by the aromatic 2-nitrobenzyl moiety causes reduction of the 2-nitro group to a nitroso group and an oxygen insertion into the carbon-hydrogen bond located in the 2-position followed by cleavage and decarboxylation (Pillai 1980).

The expected photolysis products of DNA containing a photocleavable fluorescent dye at the 3' end of the DNA are shown in FIG. 10. The 2-nitrobenzyl moiety has been successfully employed in a wide range of studies as a photocleavable-protecting group (Pillai 1980). The efficiency of the photocleavage step depends on several factors including the efficiency of light absorption by the 2-nitrobenzyl moiety, the efficiency of the primary photochemical step, and the efficiency of the secondary thermal processes which lead to the final cleavage process (Turro 1991). Burgess et al. (1997) have reported the successful photocleavage of a fluorescent dye attached through a 2-nitrobenzyl linker on a nucleotide moiety, which shows that the fluorescent dye is not quenching the photocleavage process. A photoliable protecting group based on the 2-nitrobenzyl chromophore has also been developed for biological labeling applications that involve photocleavage (Olejnik et al. 1999). The protocol disclosed herein is used to optimize the photocleavage process shown in FIG. 10. The absorption spectra of 2-nitro benzyl compounds are examined and compared quantitatively to the absorption spectra of the fluorescent dyes. Since there will be a one-to-one relationship between the number of 2-nitrobenzyl moieties and the dye molecules, the ratio of extinction coefficients of these two species will reflect the competition for light absorption at specific wavelengths. From this information, the wavelengths at which the 2-nitrobenzyl moieties absorbed most competitively can be determined, similar to the approach reported by Olejnik et al. (1995).

A photolysis setup can be used which allows a high throughput of monochromatic light from a 1000 watt high pressure xenon lamp (LX1000UV, ILC) in conjunction with a monochromator (Kratos, Schoeffel Instruments). This instrument allows the evaluation of the photocleavage of model systems as a function of the intensity and excitation wavelength of the absorbed light. Standard analytical analysis is used to determine the extent of photocleavage. From this information, the efficiency of the photocleavage as a function of wavelength can be determined. The wavelength at which photocleavage occurs most efficiently can be selected as for use in the sequencing system.

Figure 11:
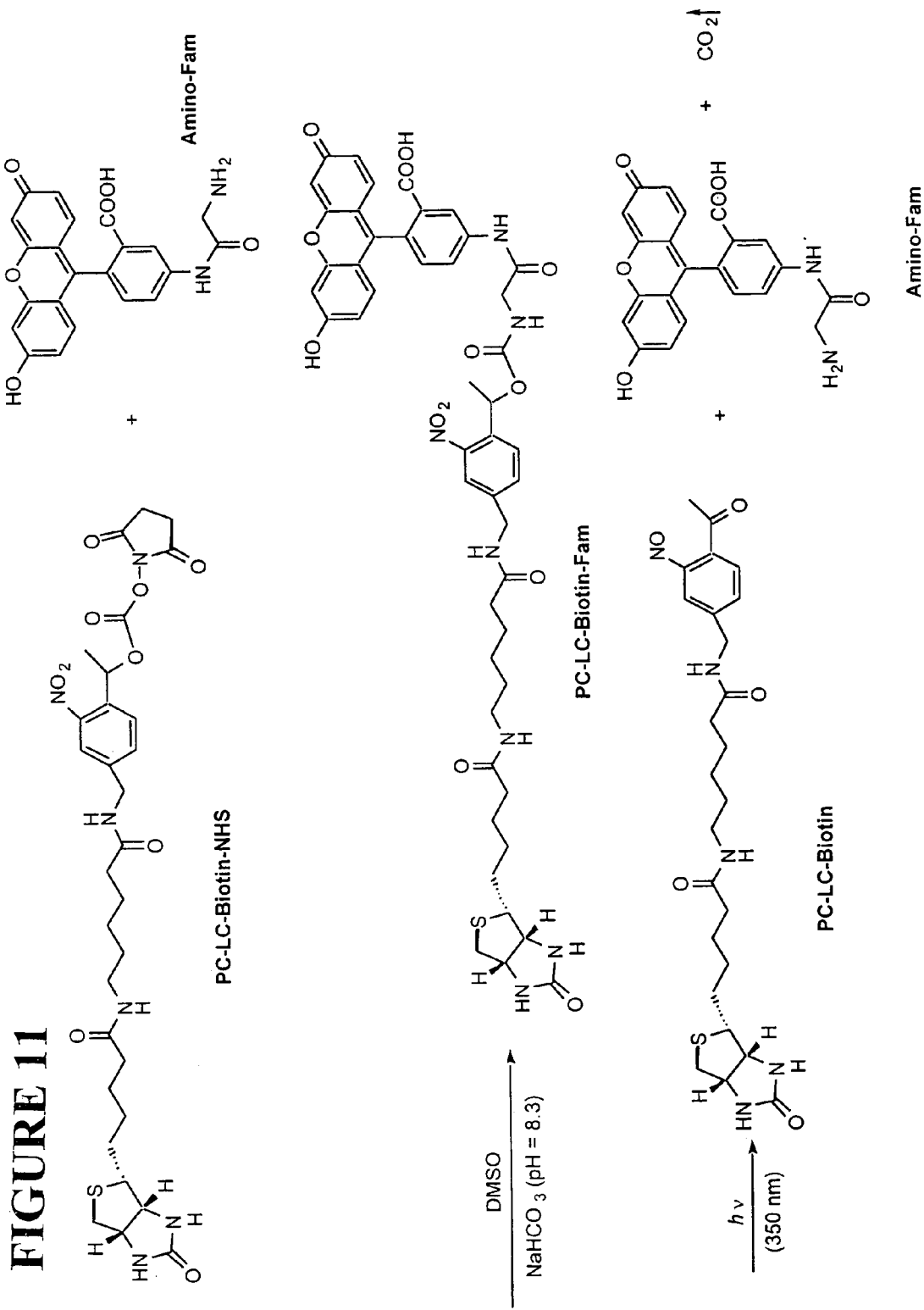
FIG. 11: Synthesis of PC-LC-Biotin-FAM to evaluate the photolysis efficiency of the fluorophore coupled with the photocleavable linker 2-nitrobenzyl group.
Figure 12:
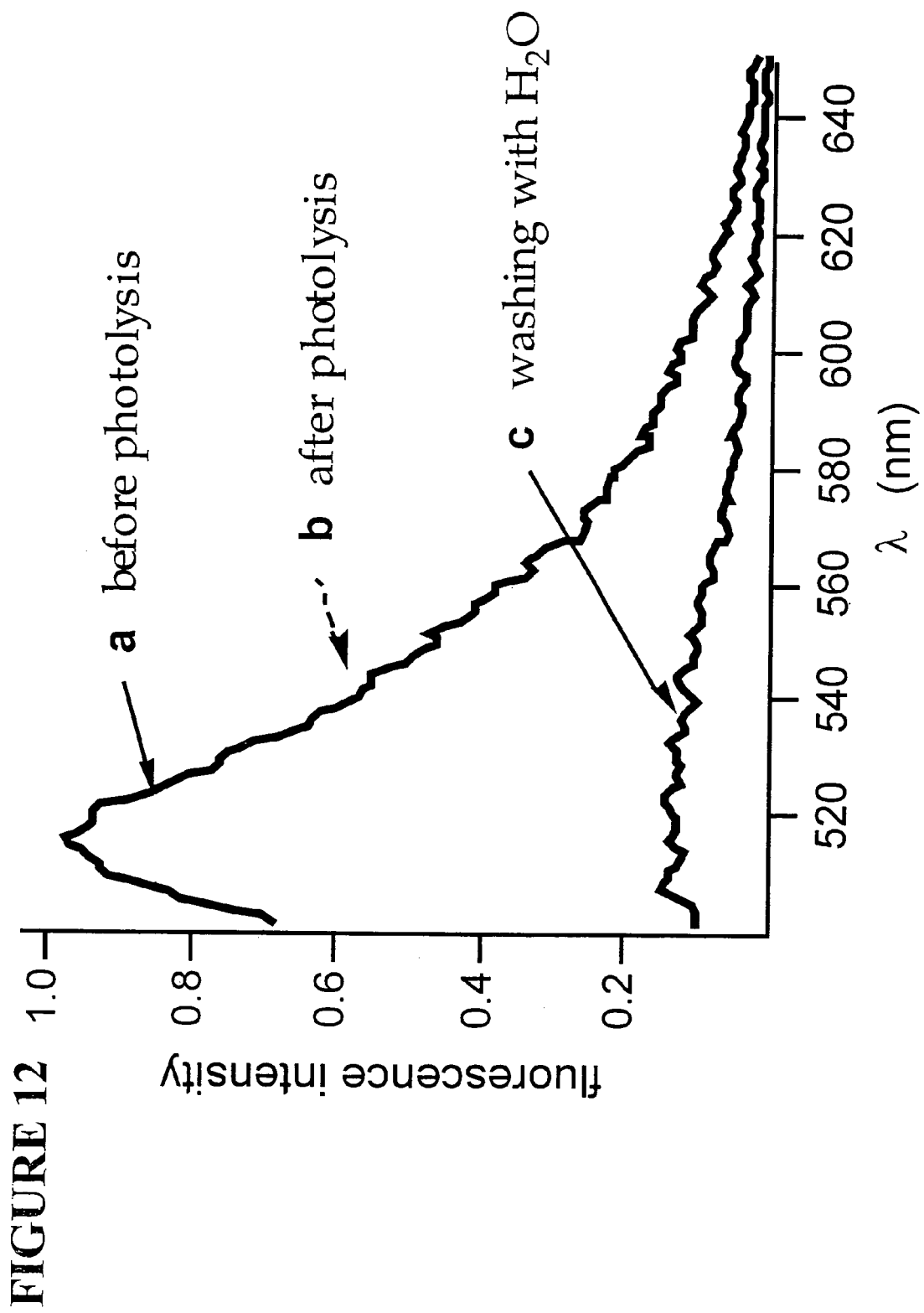
FIG. 12: Fluorescence spectra ($\lambda_{ex}$=480 nm) of PC-LC-Biotin-FAM immobilized on a microscope glass slide coated with streptavidin (a); after 10 min photolysis ($\lambda_{irr}$=350 nm; ~0.5 mW/cm$^2$) (b); and after washing with water to remove the photocleaved dye (c).

Photocleavage results have been obtained using a model system as shown in FIG. 11. Coupling of PC-LC-Biotin-NHS ester (Pierce, Rockford Ill.) with 5-(aminoacetamido)-fluorescein (5-aminoFAM) (Molecular Probes, Eugene Oreg.) in dimethylsulfonyl oxide (DMSO)/NaHCO$_3$ (pH=8.2) overnight at room temperature produces PC-LC-Biotin-FAM which is composed of a biotin at one end, a photocleavable 2-nitrobenzyl group in the middle, and a dye tag (FAM) at the other end. This photocleavable moiety closely mimics the designed photocleavable nucleotide analogues shown in FIG. 10. Thus the successful photolysis of the PC-LC-Biotin-FAM moiety provides proof of the principle of high efficiency photolysis as used in the DNA sequencing system. For photolysis study, PC-LC-Biotin-FAM is first immobilized on a microscope glass slide coated with streptavidin (XENOPORE, Hawthorne N.J.). After washing off the non-immobilized PC-LC-Biotin-FAM, the fluorescence emission spectrum of the immobilized PC-LC-Biotin-FAM was taken as shown in FIG. 12 (Spectrum a). The strong fluorescence emission indicates that PC-LC-Biotin-FAM is successfully immobilized to the streptavidin coated slide surface. The photocleavability of the 2-nitrobenzyl linker by irradiation at 350 nm was then tested. After 10 minutes of photolysis ($\lambda_{irr}$=350 nm; ~0.5 mW/cm$^2$) and before any washing, the fluorescence emission spectrum of the same spot on the slide was taken that showed no decrease in intensity (FIG. 12, Spectrum b), indicating that the dye (FAM) was not bleached during the photolysis process at 350 nm. After washing the glass slide with HPLC water following photolysis, the fluorescence emission spectrum of the same spot on the slide showed significant intensity decrease (FIG. 12, Spectrum c) which indicates that most of the fluorescence dye (FAM) was cleaved from the immobilized biotin moiety and was removed by the washing procedure. This experiment shows that high efficiency cleavage of the fluorescent dye can be obtained using the 2-nitrobenzyl photocleavable linker.

Figure 13A:
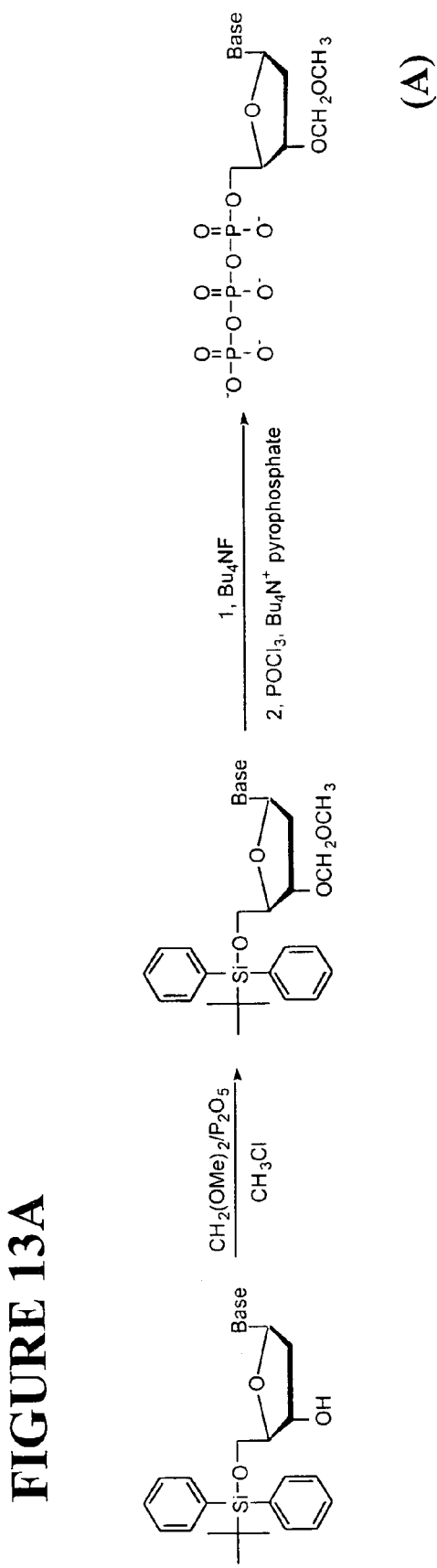
FIGS. 13A-13B: Synthetic scheme for capping the 3'-OH of nucleotide.
Figure 13B:
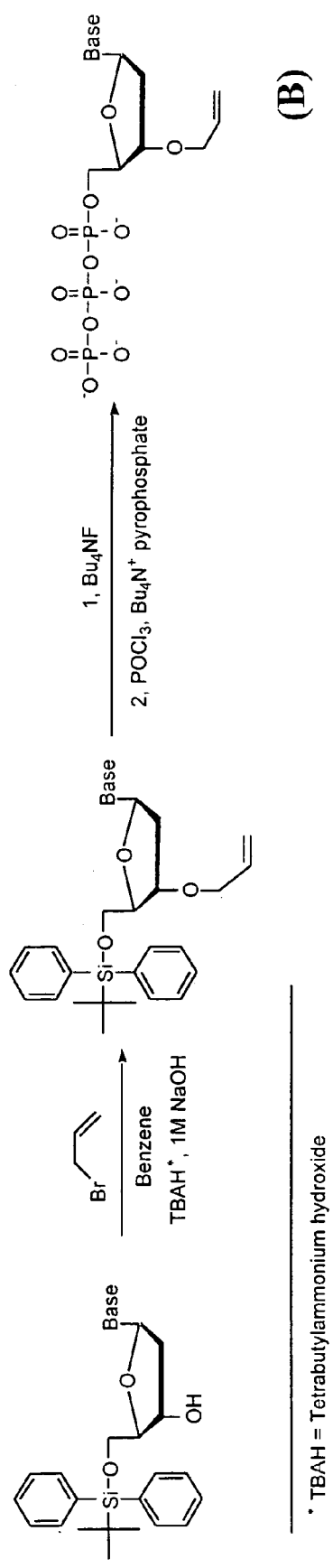
Figure 14:
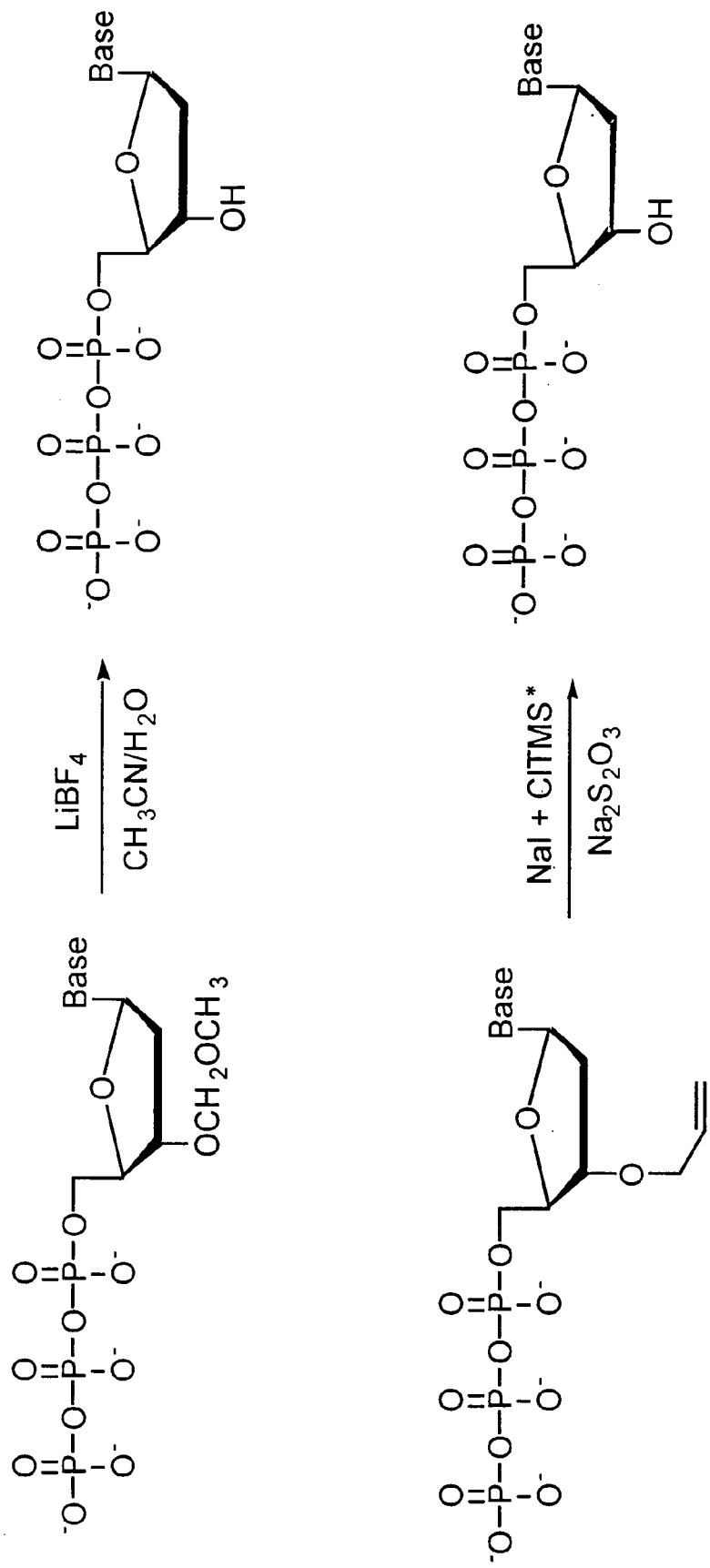
FIG. 14: Chemical cleavage of the MOM group (top row) and the allyl group (bottom row) to free the 3'-OH in the nucleotide. CITMS=chlorotrimethylsilane.

4. Sequencing by Synthesis Evaluation Using Nucleotide Analogues $_{3'-RO}$-A-$_{Dye1}$, $_{3'-RO}$-C-$_{Dye2}$, $_{3'-RO}$-G-$_{Dye3}$, $_{3'-RO}$-T-$_{Dye4}$ Once the steps and conditions in Section 3 are optimized, the synthesis of nucleotide analogues $_{3'-RO}$-A-$_{Dye1}$, $_{3'-RO}$-C-$_{Dye2}$, $_{3'-RO}$-G-$_{Dye3}$, $_{3'-RO}$-T-$_{Dye4}$ can be pursued for further study of the system. Here the 3'-OH is capped in all four nucleotide analogues, which then can be mixed together with DNA polymerase and used to evaluate the sequencing system using the scheme in FIG. 9. The MOM (—CH$_2$OCH$_3$) or allyl (—CH$_2$CH=CH$_2$) group is used to cap the 3'-OH group using well-established synthetic procedures (FIG. 13) (Fuji et al. 1975, Metzker et al. 1994). These groups can be removed chemically with high yield as shown in FIG. 14 (Ireland, et al. 1986; Kamal et al. 1999). The chemical cleavage of the MOM and allyl groups is fairly mild and specific, so as not to degrade the DNA template moiety. For example, the cleavage of the allyl group takes 3 minutes with more than 93% yield (Kamal et al. 1999), while the MOM group is reported to be cleaved with close to 100% yield (Ireland, et al. 1986).

5. Using Energy Transfer Coupled Dyes To Optimize The Sequencing By Synthesis System The spectral property of the fluorescent tags can be optimized by using energy transfer (ET) coupled dyes.

Figure 15A:
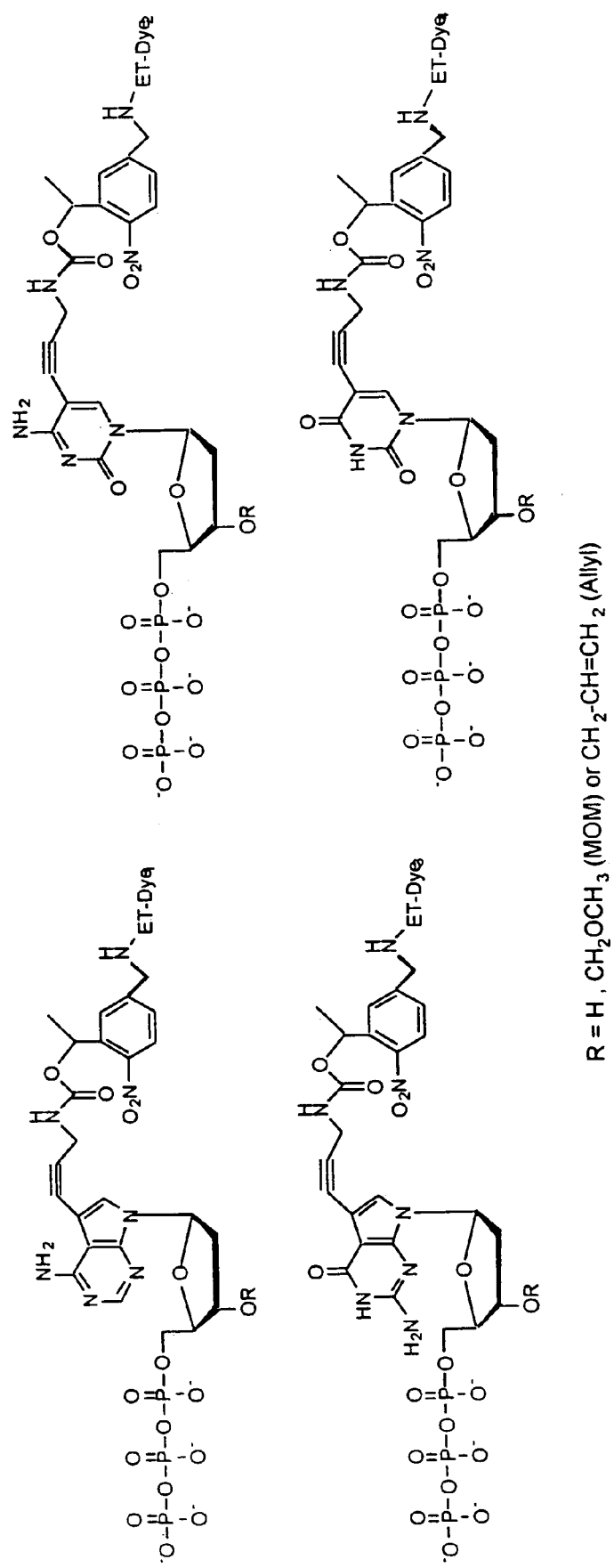
FIGS. 15A-15B: Examples of energy transfer coupled dye systems, where Fam or Cy2 is employed as a light absorber (energy transfer donor) and $Cl_2$Fam, $Cl_2$R6G, $Cl_2$Tam, or $Cl_2$Rox as an energy transfer acceptor. Cy2, cyanine; FAM, 5-carboxyfluorescein; R6G, 6-carboxyrhodamine-6G; TAM, N,N,N',N'-tetramethyl-6-carboxyrhodamine; ROX, 6-carboxy-X-rhodamine.
Figure 15B:
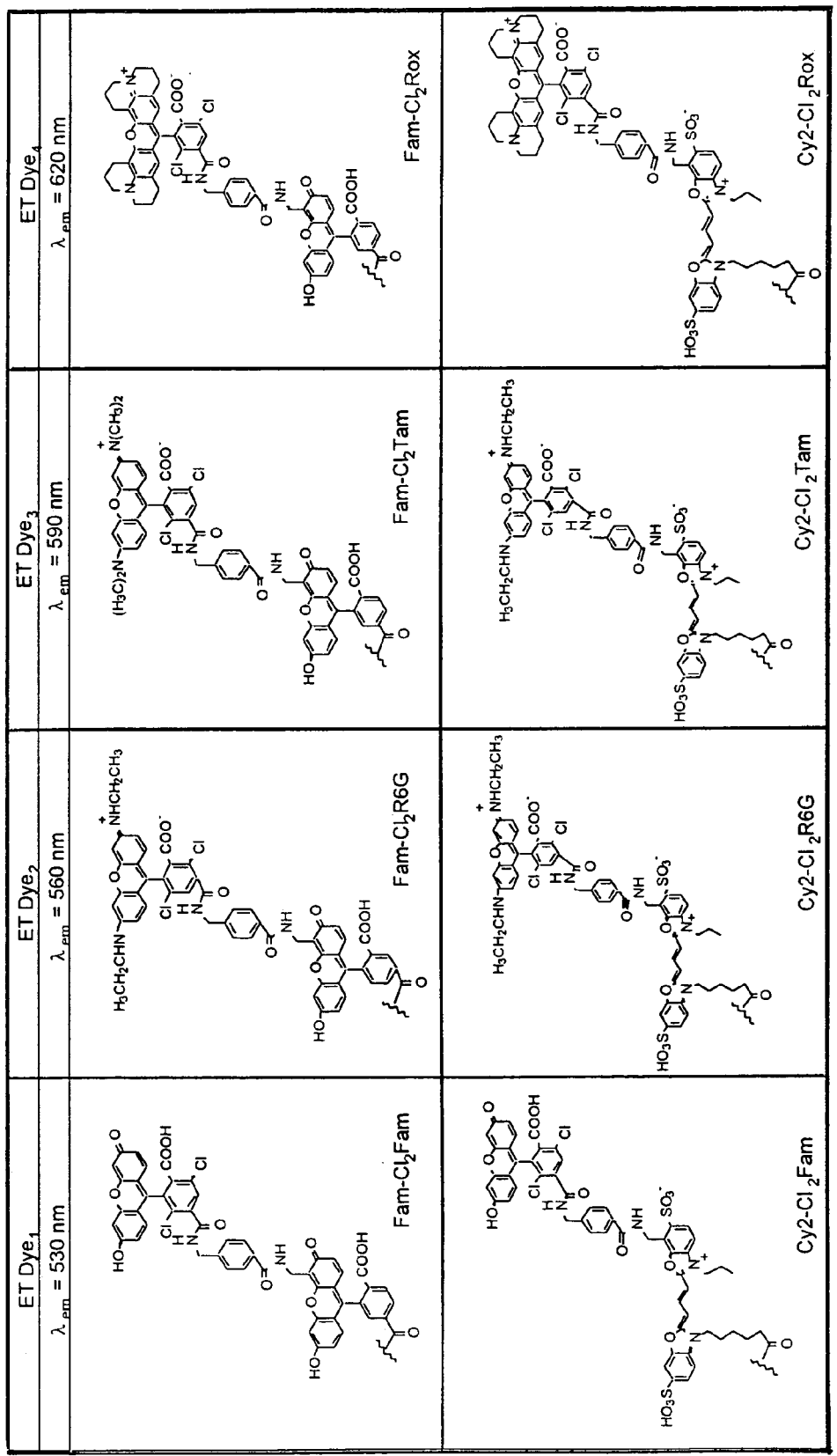
Figure 16:
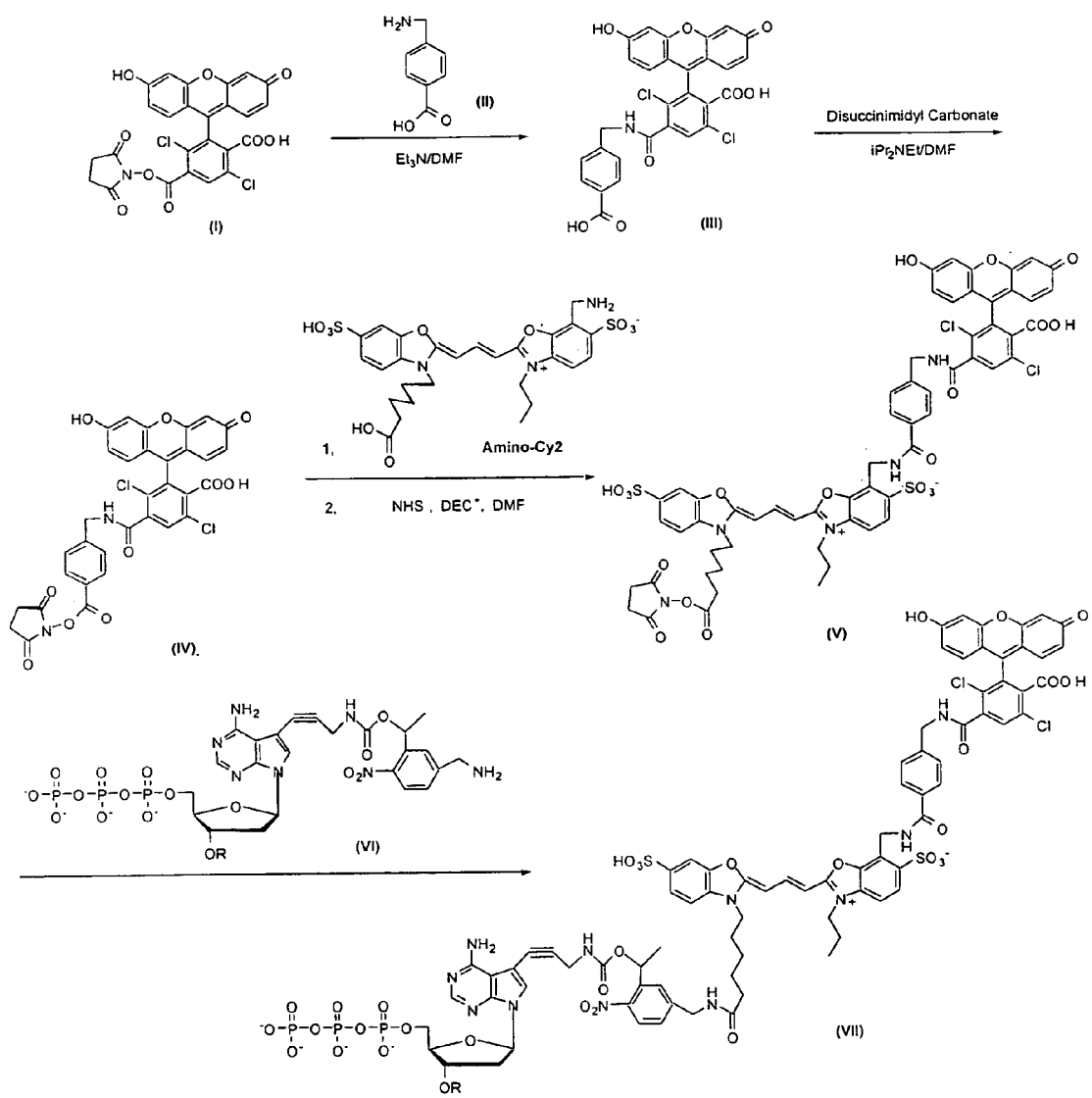
FIG. 16: The synthesis of a photocleavable energy transfer dye-labeled nucleotide. DMF, dimethylformide. DEC=1-(3-dimethylaminopropyl)-3-ethylcarbodimide hydrochloride. R=H, $CH_2OCH_3$ (MOM) or $CH_2CH=CH_2$ (Allyl).

The ET primer and ET dideoxynucleotides have been shown to be a superior set of reagents for 4-color DNA sequencing that allows the use of one laser to excite multiple sets of fluorescent tags (Ju et al. 1995). It has been shown that DNA polymerase (Thermo Sequenase and Taq FS) can efficiently incorporate the ET dye labeled dideoxynucleotides (Rosenblum et al. 1997). These ET dye-labeled sequencing reagents are now widely used in large scale DNA sequencing projects, such as the human genome project. A library of ET dye labeled nucleotide analogues can be synthesized as shown in FIG. 15 for optimization of the DNA sequencing system. The ET dye set (FAM-Cl$_2$FAM, FAM-Cl$_2$R6G, FAM-Cl$_2$TAM, FAM-Cl$_2$ROX) using FAM as a donor and dichloro(FAM, R6G, TAM, ROX) as acceptors has been reported in the literature (Lee et al. 1997) and constitutes a set of commercially available DNA sequencing reagents. These ET dye sets have been proven to produce enhanced fluorescence intensity, and the nucleotides labeled with these ET dyes at the 5-position of T and C and the 7-position of G and A are excellent substrates of DNA polymerase. Alternatively, an ET dye set can be constructed using cyanine (Cy2) as a donor and Cl$_2$FAM, Cl$_2$R6G, Cl$_2$TAM, or Cl$_2$ROX as energy acceptors. Since Cy2 possesses higher molar absorbance compared with the rhodamine and fluorescein derivatives, an ET system using Cy2 as a donor produces much stronger fluorescence signals than the system using FAM as a donor (Hung et al. 1996). FIG. 16 shows a synthetic scheme for an ET dye labeled nucleotide analogue with Cy2 as a donor and Cl$_2$FAM as an acceptor using similar coupling chemistry as for the synthesis of an energy transfer system using FAM as a donor (Lee et al. 1997). Coupling of Cl$_2$FAM (I) with spacer 4-aminomethylbenzoic acid (II) produces III, which is then converted to NHS ester IV. Coupling of IV with amino-Cy2, and then converting the resulting compound to a NHS ester produces V, which subsequently couples with amino-photolinker nucleotide VI yields the ET dye labeled nucleotide VII.

Figure 17:
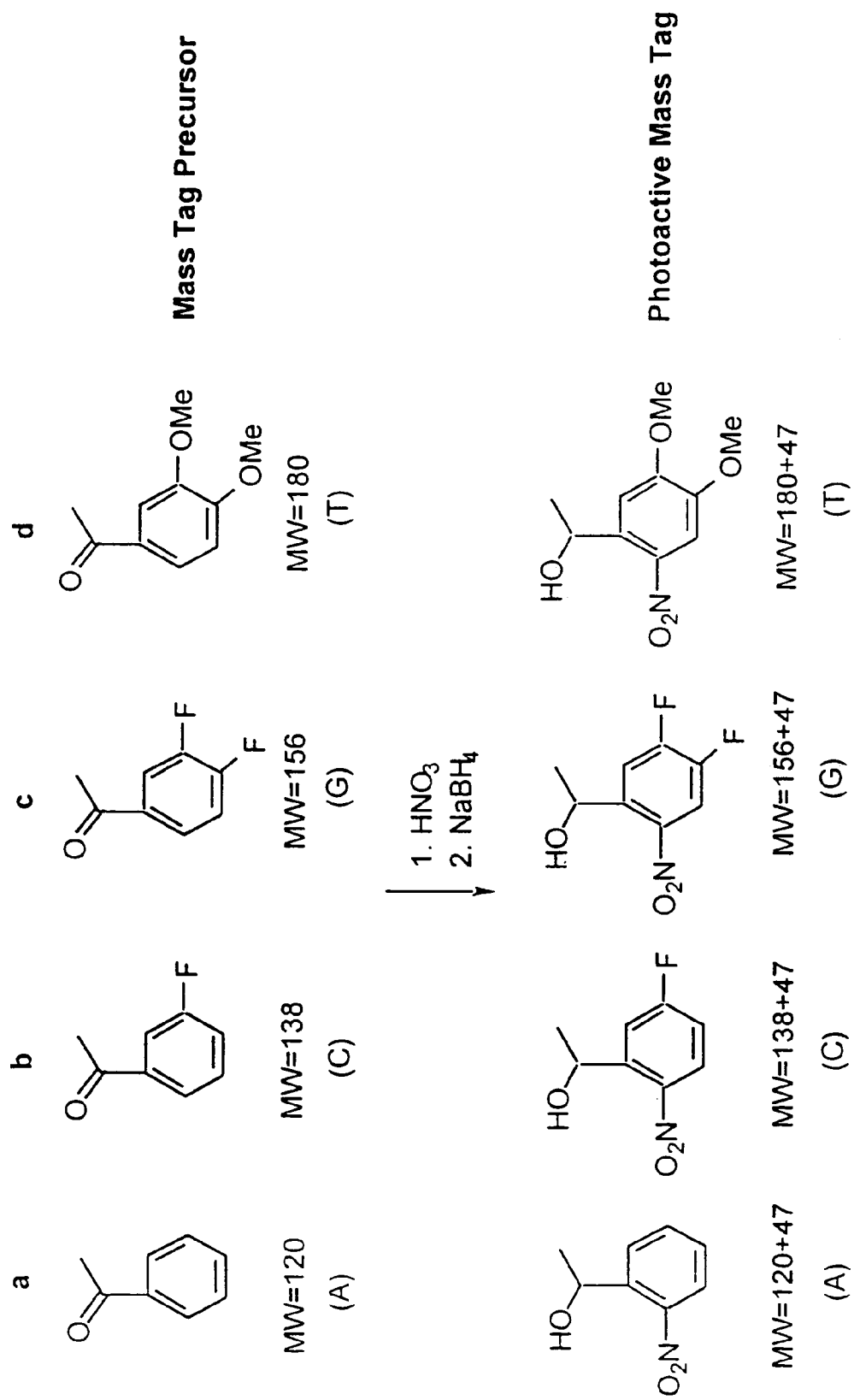
FIG. 17: Structures of four mass tag precursors and four photoactive mass tags. Precursors: a) acetophenone; b) 3-fluoroacetophenone; c) 3,4-difluoroacetophenone; and d) 3,4-dimethoxyacetophenone. Four photoactive mass tags are used to code for the identity of each of the four nucleotides (A, C, G, T).
Figure 18:
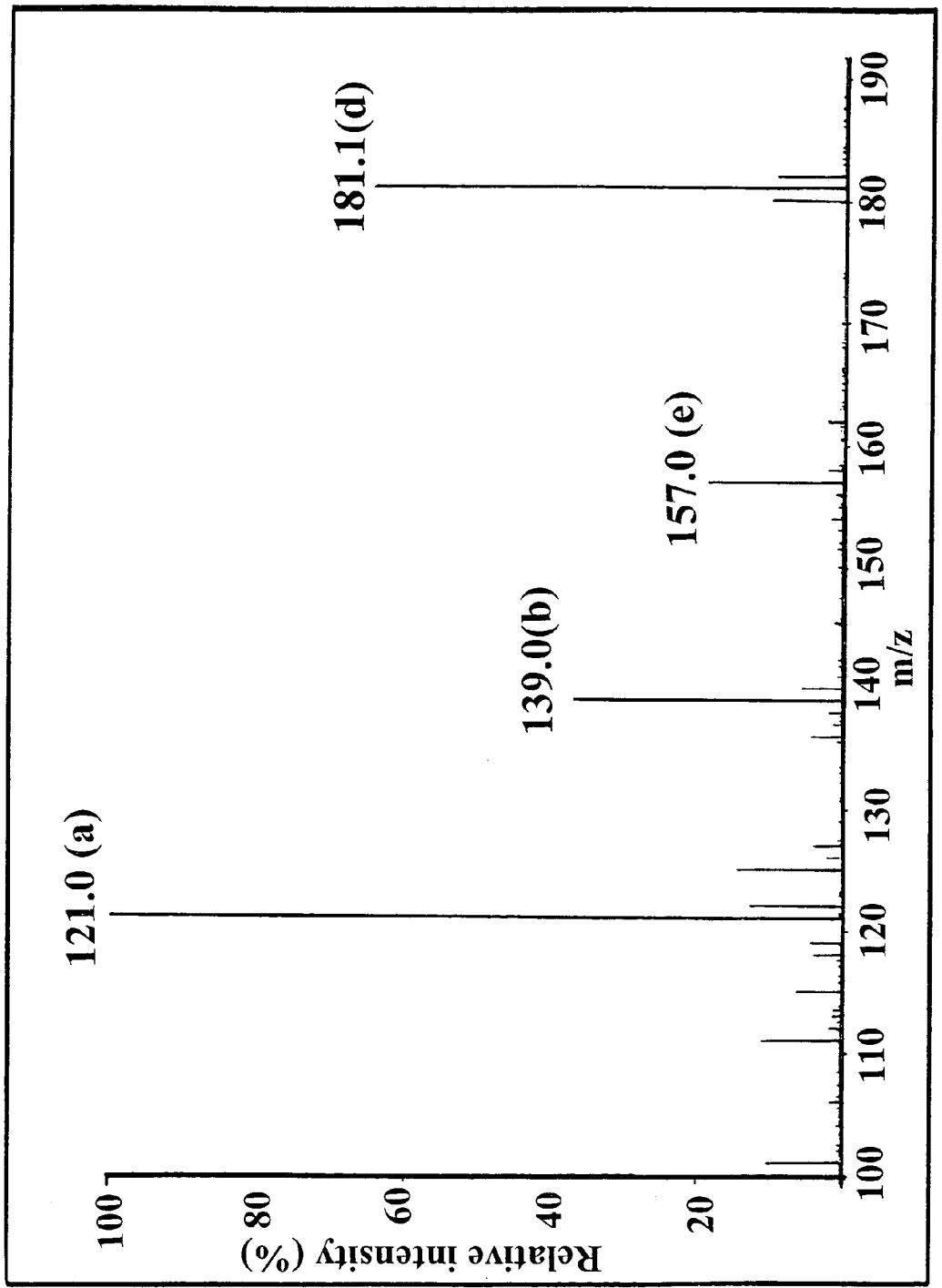
FIG. 18: Atmospheric Pressure Chemical Ionization (APCI) mass spectrum of mass tag precursors shown in FIG. 17.

6. Sequencing by Synthesis Evaluation Using Nucleotide Analogues $_{3'-HO}$-A-$_{Tag1}$, $_{3'-HO}$-C-$_{Tag2}$, $_{3'-HO}$-G-$_{Tag3}$, $_{3'-HO}$-T-$_{Tag4}$ The precursors of four examples of mass tags are shown in FIG. 17. The precursors are: (a) acetophenone; (b) 3-fluoroacetophenone; (c) 3,4-difluoroacetophenone; and (d) 3,4-dimethoxyacetophenone. Upon nitration and reduction, four photoactive tags are produced from the four precursors and used to code for the identity of each of the four nucleotides (A, C, G, T). Clean APCI mass spectra are obtained for the four mass tag precursors (a, b, c, d) as shown in FIG. 18. The peak with m/z of 121 is a, 139 is b, 157 is c, and 181 is d. This result shows that these four mass tags are extremely stable and produce very high resolution data in an APCI mass spectrometer with no cross talk between the mass tags. In the examples shown below, each of the unique m/z from each mass tag translates to the identity of the nucleotide [Tag-1 (m/z, 150)=A; Tag-2 (m/z, 168)=C; Tag-3 (m/z, 186)=G; Tag-4 (m/z, 210)=T].

Figure 19:
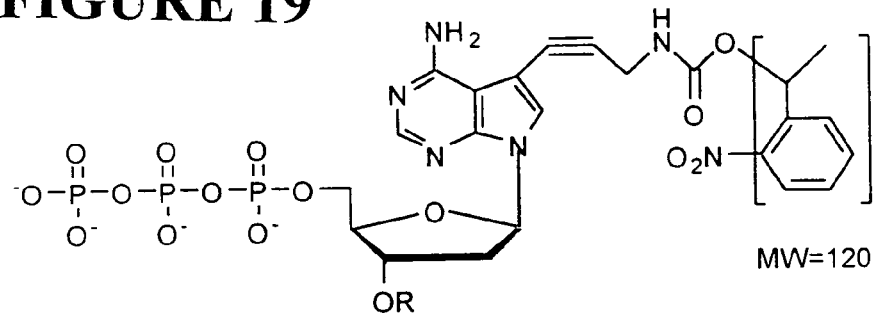
FIG. 19: Examples of structures of four nucleotide analogues for use in the sequencing by synthesis approach. Each nucleotide analogue has a unique mass tag attached to the base through a photocleavable linker, and the 3'-OH is either exposed or capped with a MOM group or an allyl group. The square brackets indicated that the mass tag is cleavable. R=H, $CH_2OCH_3$ (MOM) or $CH_2CH=CH_2$ (Allyl).
Figure 19:
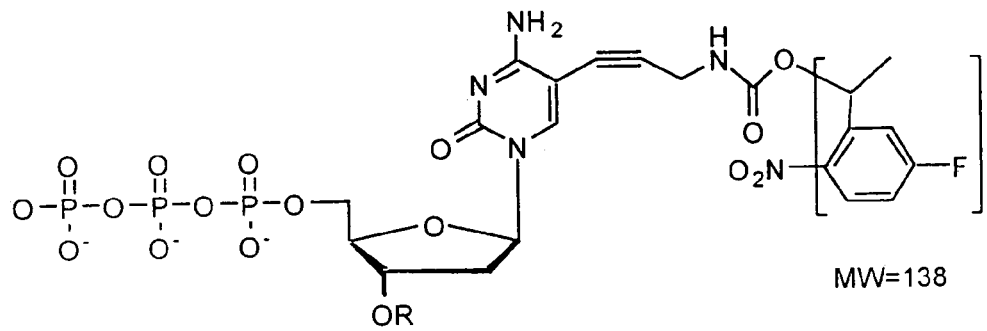
Figure 19:
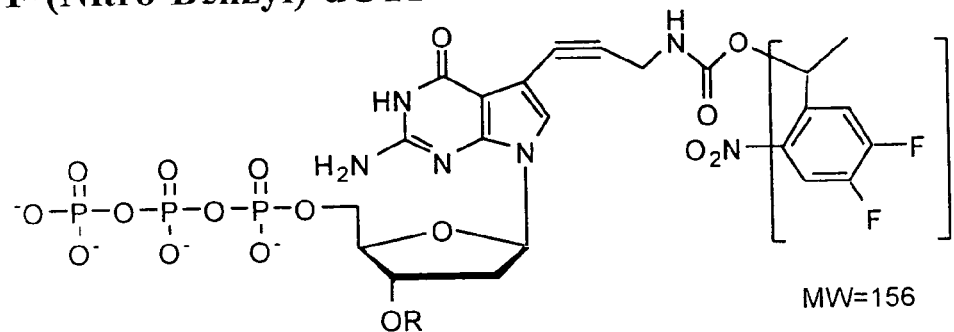
Figure 19:
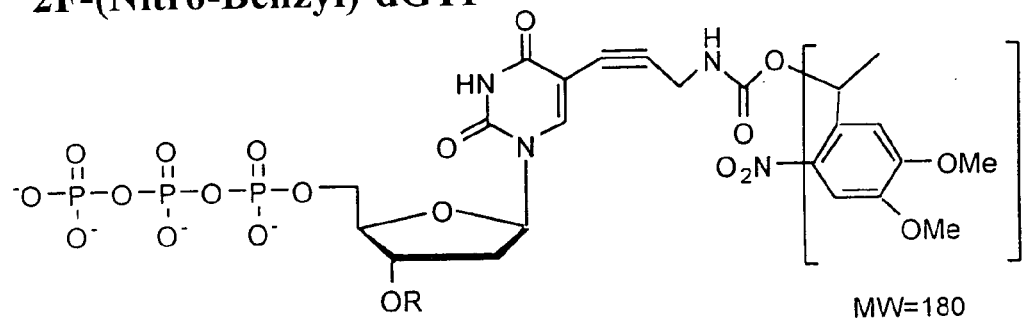

Different combinations of mass tags and nucleotides can be used, as indicated by the general scheme: $_{3'-HO}$-A-$_{Tag1}$, $_{3'-HO}$-C-$_{Tag2}$, $_{3'-HO}$-G-$_{Tag3}$, $_{3'-HO}$-T-$_{Tag4}$ where Tag1, Tag2, Tag3, and Tag4 are four different unique cleavable mass tags. Four specific examples of nucleotide analogues are shown in FIG. 19. In FIG. 19, "R" is H when the 3'-OH group is not capped. As discussed above, the photo cleavable 2-nitro benzyl moiety has been used to link biotin to DNA and protein for efficient removal by UV light (~350 nm) irradiation (Olejnik et al. 1995, 1999). Four different 2-nitro benzyl groups with different molecular weights as mass tags are used to form the mass tag labeled nucleotides as shown in FIG. 19: 2-nitro-α-methyl-benzyl (Tag-1) codes for A;

2-nitro-α-methyl-3-fluorobenzyl (Tag-2) codes for C; 2-nitro-α-methyl-3,4-difluorobenzyl (Tag-3) codes for G; 2-nitro-α-methyl-3,4-dimethoxybenzyl (Tag-4) codes for T.

Figure 20:
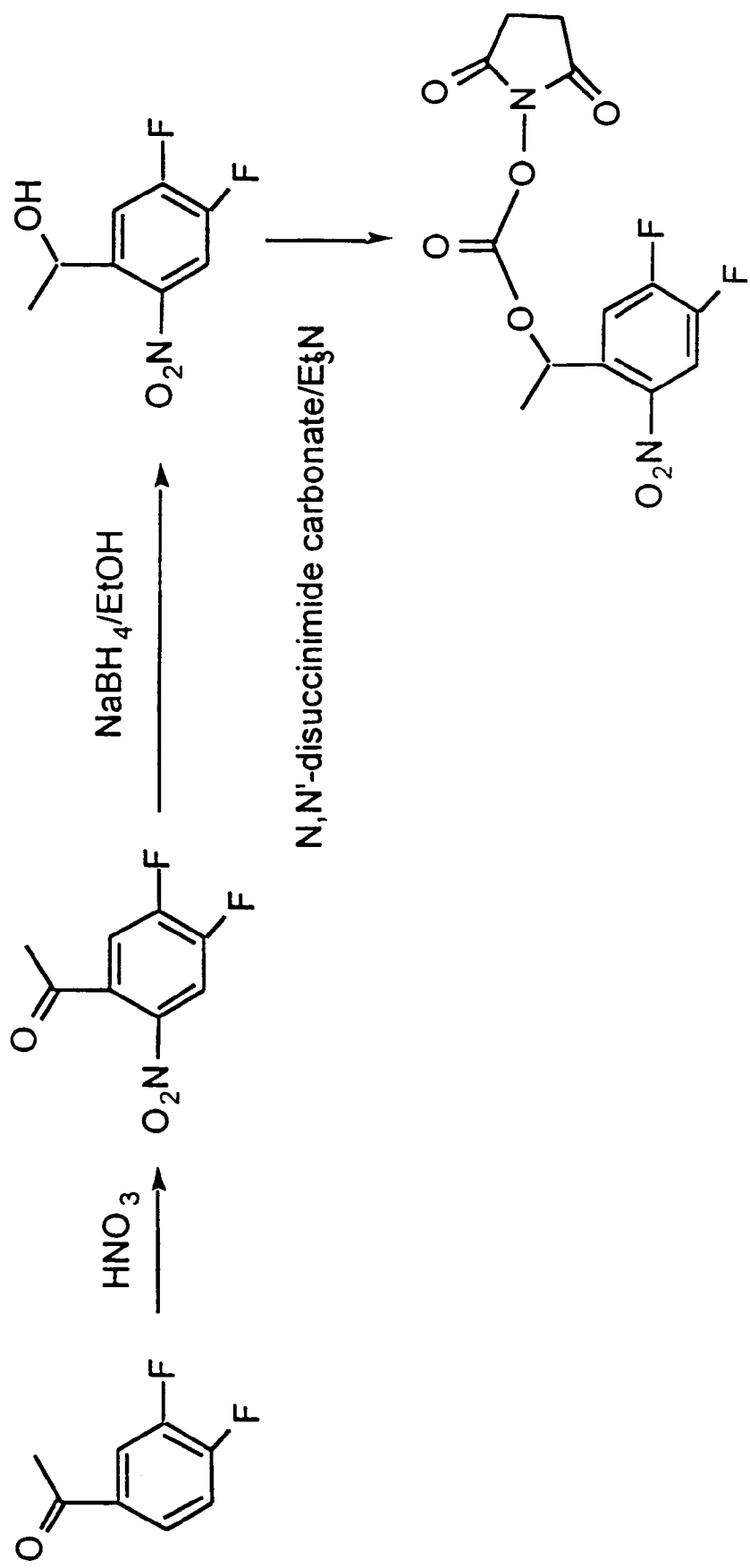
FIG. 20: Example of synthesis of NHS ester of one mass tag (Tag-3). A similar scheme is used to create other mass tags.
Figure 21:
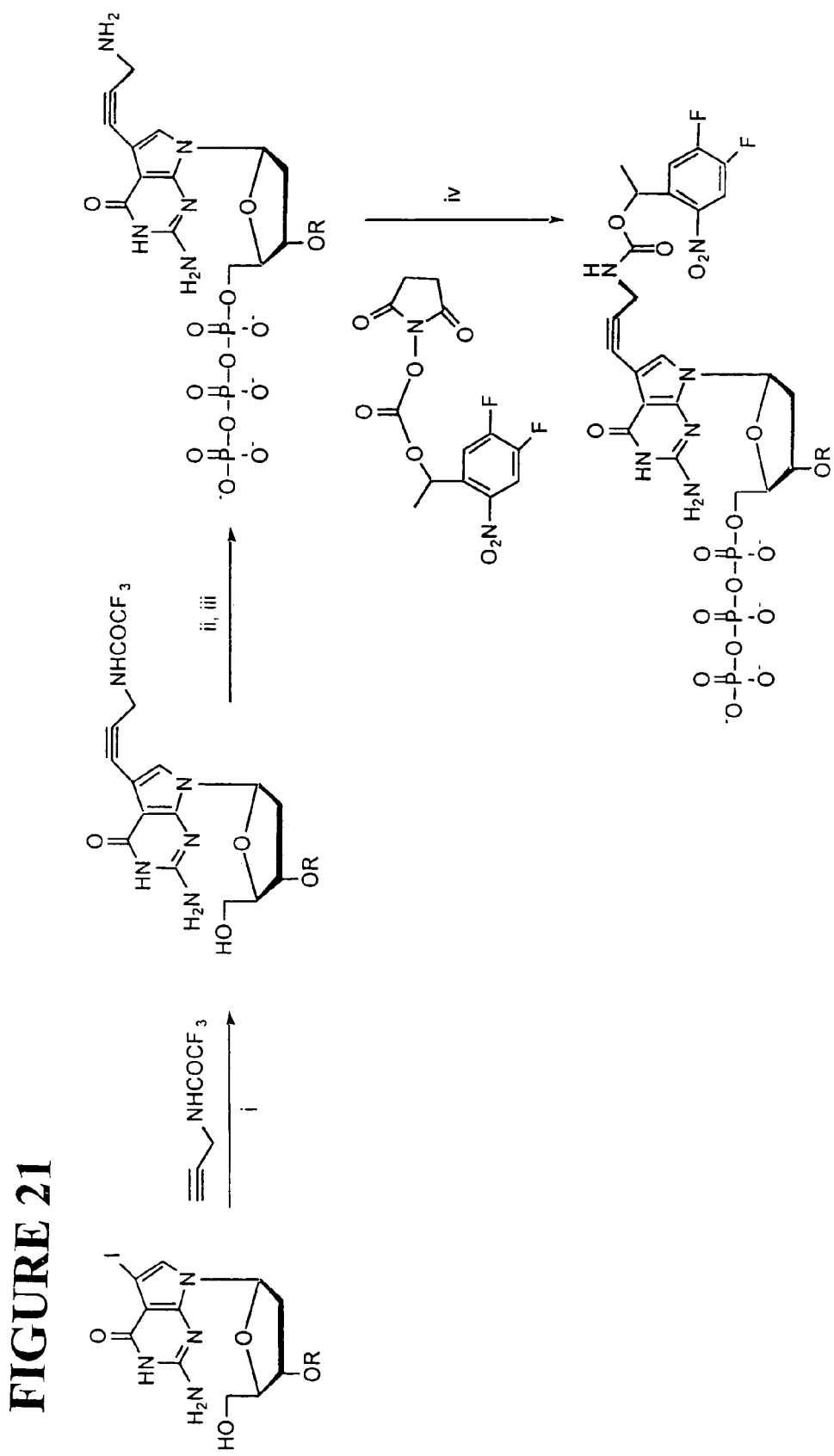
FIG. 21: A representative scheme for the synthesis of the nucleotide analogue $_{3'\text{-}RO}\text{-}G\text{-}_{Tag3}$. A similar scheme is used to create the other three modified bases $_{3'\text{-}RO}\text{-}A\text{-}_{Tag1}$, $_{3'\text{-}RO}\text{-}C\text{-}_{Tag2}$, $_{3'\text{-}RO}\text{-}T\text{-}_{Tag4}$. (i) tetrakis(triphenylphosphine)palladium(0); (ii) POCl$_3$, Bn$_4$N$^+$pyrophosphate; (iii) NH$_4$OH; (iv) Na$_2$CO$_3$/NaHCO$_3$ (pH=9.0)/DMSO.

As a representative example, the synthesis of the NHS ester of one mass tag (Tag-3) is shown in FIG. 20. A similar scheme is used to create the other mass tags. The synthesis of $_{3'\text{-}HO}$-G-$_{Tag3}$ is shown in FIG. 21 using well-established procedures (Prober et al. 1987; Lee et al. 1992 and Hobbs et al. 1991). 7-propargylamino-dGTP is first prepared by reacting 7-I-dGTP with N-trifluoroacetylpropargyl amine, which is then coupled with the NHS-Tag-3 to produce $_{3'\text{-}HO}$-G-$_{Tag3}$. The nucleotide analogues with a free 3'-OH are good substrates for the polymerase.

Figure 9:
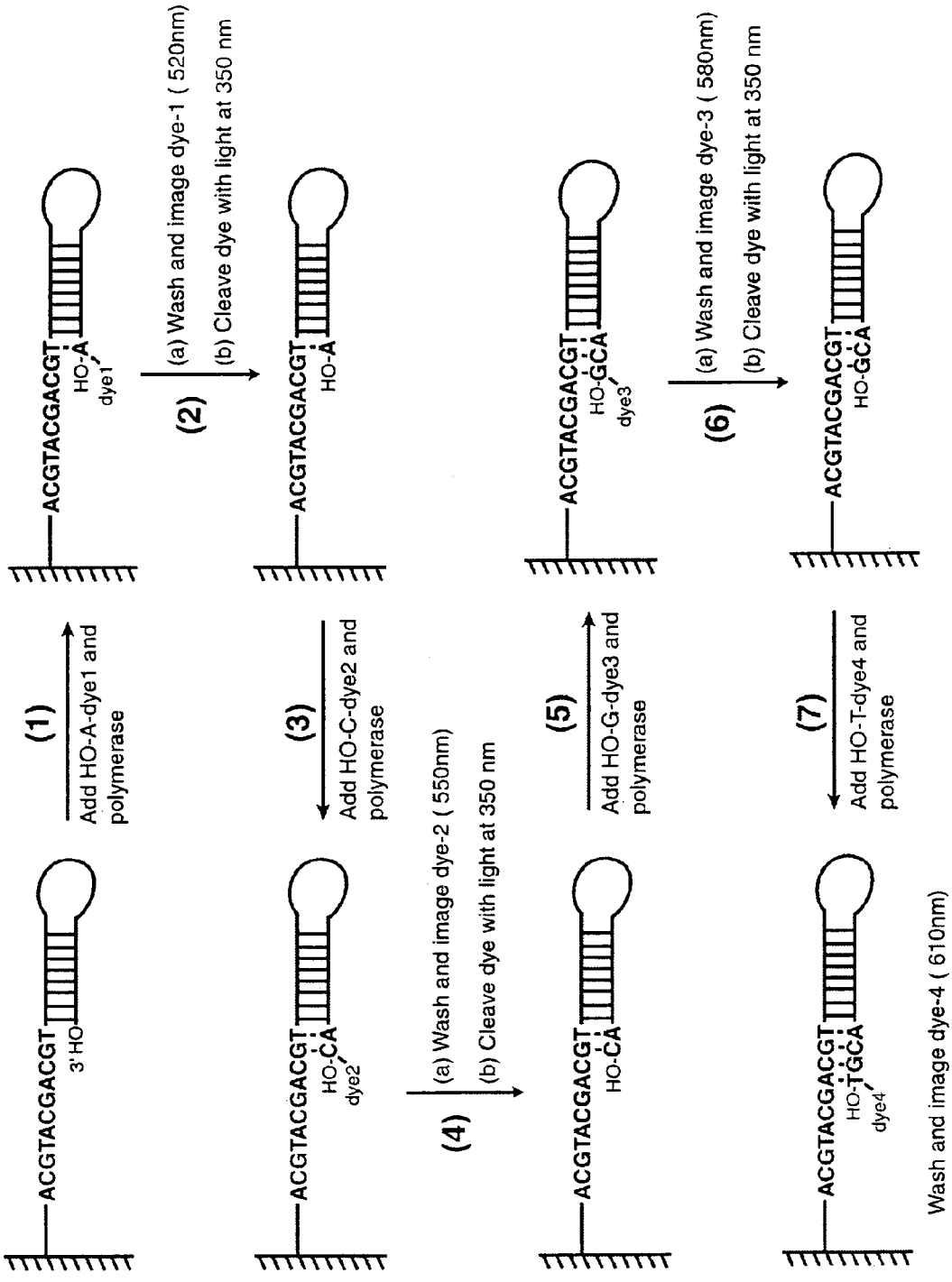
FIG. 9: A scheme for testing the sequencing by synthesis approach. Each nucleotide, modified by the attachment of a unique fluorescent dye, is added one by one, based on the complimentary template. The dye is detected and cleaved to test the approach. Dye1=Fam; Dye2=R6G; Dye3=Tam; Dye4=Rox.
Figure 22:
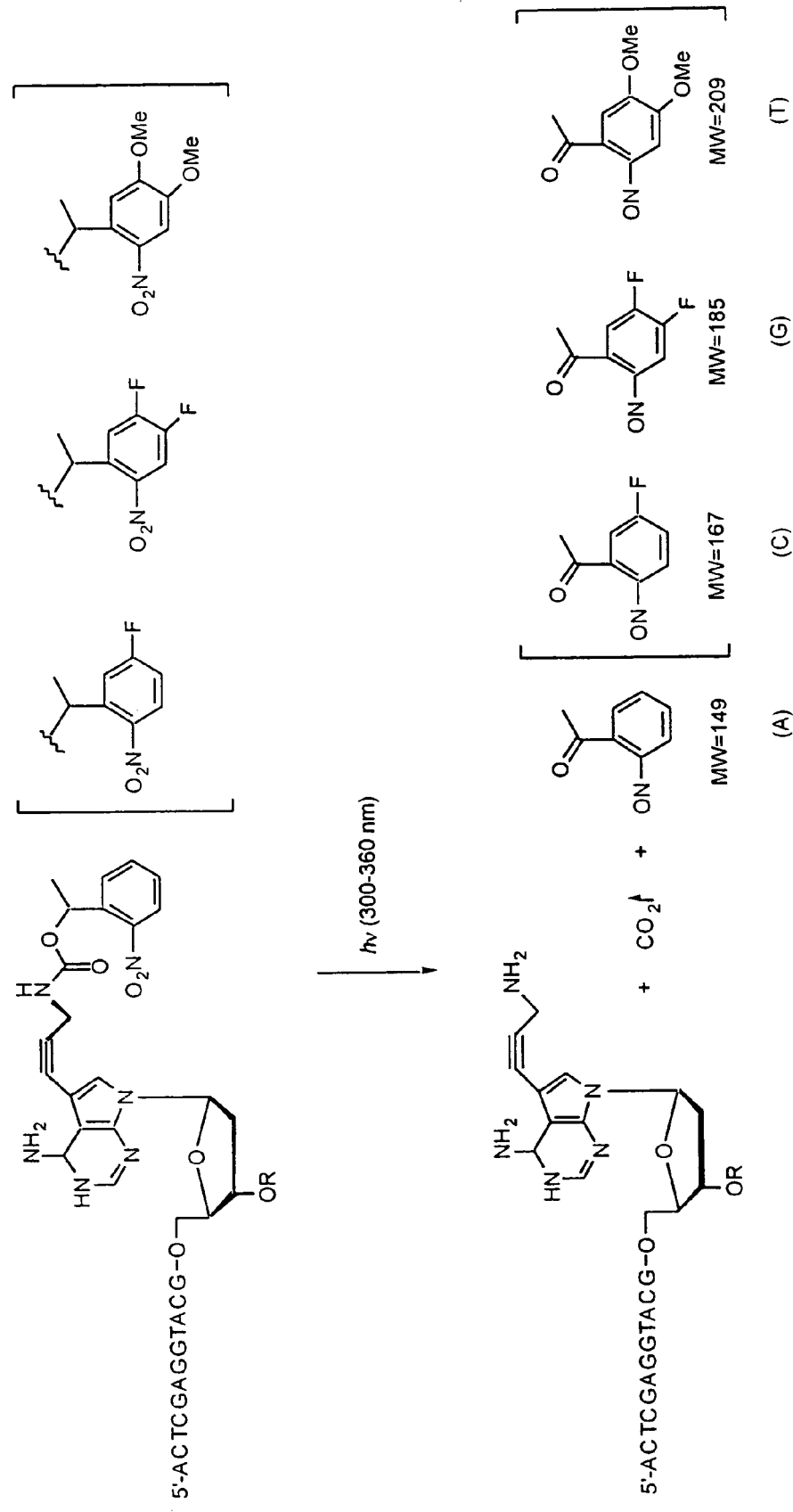
FIG. 22: Examples of expected photocleavage products of DNA containing a photocleavable mass tag.

The sequencing by synthesis approach can be tested using mass tags using a scheme similar to that show for dyes in FIG. 9. A DNA template containing a portion of nucleotide sequence that has no repeated sequences after the priming site, is synthesized and immobilized to a glass channel. $_{3'\text{-}HO}$-A-$_{Tag1}$ and DNA polymerase are added to the self-primed DNA moiety to allow the incorporation of the nucleotide into the 3' site of the DNA. Then the steps in FIG. 2B are followed (the chemical cleavage is not required here because the 3'-OH is free) to detect the mass tag from Tag-1 (m/z=150). Next, $_{3'\text{-}HO}$-C-$_{Tag2}$ is added and the resulting mass spectra is measured after cleaving Tag-2 (m/z=168). Next, $_{3'\text{-}HO}$-G-$_{Tag3}$ and $_{3'\text{-}HO}$-T-$_{Tag4}$ are added in turn and the mass spectra of trie cleavage products Tag-3 (m/z=186) and Tag-4 (m/z=210) are measured. Examples of expected photocleavage products are shown in FIG. 22. The photocleavage mechanism is as described above for the case where the unique labels are dyes. Light absorption (300-360 nm) by the aromatic 2-nitro benzyl moiety causes reduction of the 2-nitro group to a nitroso group and an oxygen insertion into the carbon-hydrogen bond located in the 2-position followed by cleavage and decarboxylation (Pillai 1980)

The synthesis of nucleotide analogues $_{3'\text{-}RO}$-A-$_{Tag1}$, $_{3'\text{-}RO}$-C-$_{Tag2}$, $_{3'\text{-}RO}$-G-$_{Tag3}$, $_{3'\text{-}RO}$-T-$_{Tag4}$ can be pursued for further study of the system a discussed above for the case where the unique labels are dyes. Here the 3'-OH is capped in all four nucleotide analogues, which then can be mixed together with DNA polymerase and used to evaluate the sequencing system using a scheme similar to that in FIG. 9. The MOM (—CH$_2$OCH$_3$) or allyl (—CH$_2$CH=CH$_2$) group is used to cap the 3'-OH group using well-established synthetic procedures (FIG. 13) (Fuji et ,al. 1975, Metzker et al. 1994). These groups can be removed chemically with high yield as shown in FIG. 14 (Ireland, et al. 1986; Kamal et al. 1999). The chemical cleavage of the MOM and allyl groups is fairly mild and specific, so as not to degrade the DNA template moiety.

7. Parallel Channel System for Sequencing by Synthesis

Figure 23:
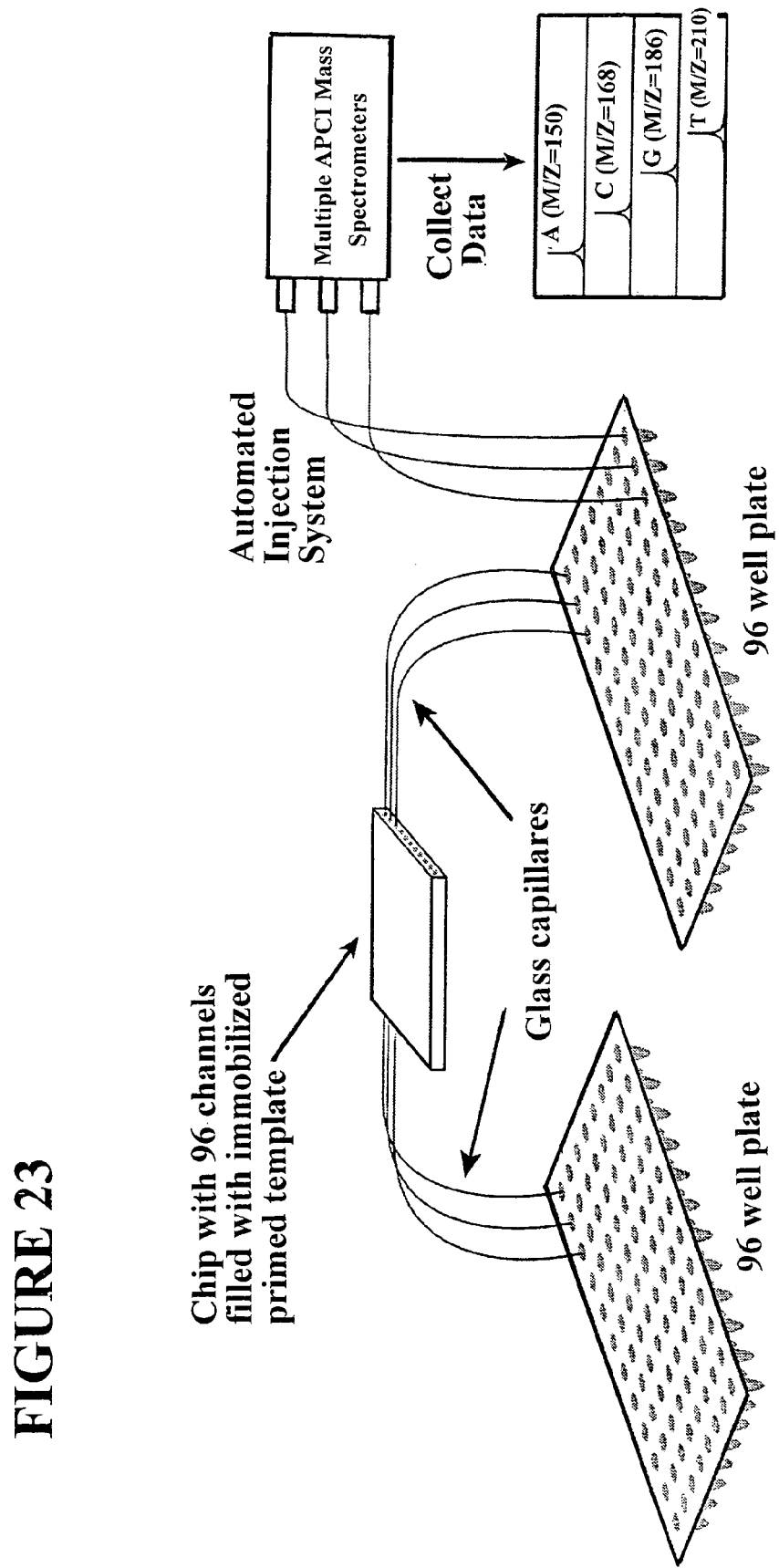
FIG. 23: System for DNA sequencing comprising multiple channels in parallel and multiple mass spectrometers in parallel. The example shows 96 channels in a silica glass chip.

FIG. 23 illustrates an example of a parallel channel system. The system can be used with mass tag labels as shown and also with dye labels. A plurality of channels in a silica glass chip are connected on each end of the channel to a well in a well plate. In the example shown there are 96 channels each connected to its own wells. The sequencing system also permits a number of channels other than 96 to be used. 96 channel devices for separating DNA sequencing and sizing fragments have been reported (Woolley and Mathies 1994, Woolley et al. 1997, Simpson et al. 1998). The chip is made by photolithographic masking and chemical etching techniques. The photolithographically defined channel patterns are etched in a silica glass substrate, and then capillary channels (id~100 μm) are formed by thermally bonding the etched substrate to a second silica glass slide. Channels are porous to increase surface area. The immobilized single stranded DNA template chip is prepared according to the scheme shown in FIG. 3. Each channel is first treated with 0.5 M NaOH, washed with water, and is then coated with high density 3-aminopropyltrimethoxysilane in aqueous ethanol (Woolley et al. 1994) forming a primary amine surface. Succinimidyl (NHS) ester of triarylphosphine (1) is covalently coupled with the primary amine group converting the amine surface to a novel triarylphosphine surface, which specifically reacts with DNA containing an azido group (2) forming a chip with immobilized DNA. Since the azido group is only located at the 5' end of the DNA and the coupling reaction is through the unique reaction of triarylphosphine moiety with azido group in aqueous solution (Saxon and Bertozzi 2000), such a DNA surface provides an optimized condition for hybridization. Fluids, such as sequencing reagents and washing solutions, can be easily pressure driven between the two 96 well plates to wash and add reagents to each channel in the chip for carrying out the polymerase reaction as well as collecting the photocleaved labels. The silica chip is transparent to ultraviolet light (λ~350 nm). In the Figure, photocleaved mass tags are detected by an APCI mass spectrometer upon irradiation with a UV light source.

8. Parallel Mass Tag Sequencing by Synthesis System

The approach disclosed herein comprises detecting four unique photoreleased mass tags, which can have molecular weights from 150 to 250 daltons, to decode the DNA sequence, thereby obviating the issue of detecting large DNA fragments using a mass spectrometer as well as the stringent sample requirement for using mass spectrometry to directly detect long DNA fragments. It takes 10 seconds or less to analyze each mass tag using the APCI mass spectrometer. With 8 miniaturized APCI mass spectrometers in a system, close to 100,000 bp of high quality digital DNA sequencing data could be generated each day by each instrument using this approach. Since there is no separation and purification requirements using this approach, such a system is cost effective.

To make mass spectrometry competitive with a 96 capillary array method for analyzing DNA, a parallel mass spectrometer approach is needed. Such a complete system has not been reported mainly due to the fact that most of the mass spectrometers are designed to achieve adequate resolution for large biomolecules. The system disclosed herein requires the detection of four mass tags, with molecular weight range between 150 and 250 daltons, coding for the identity of the four nucleotides (A, C, G, T). Since a mass spectrometer dedicated to detection of these mass tags only requires high resolution for the mass range of 150 to 250 daltons instead of covering a wide mass range, the mass spectrometer can be miniaturized and have a simple design. Either quadrupole (including ion trap detector) or time-of-flight mass spectrometers can be selected for the ion optics. While modern mass spectrometer technology has made it possible to produce miniaturized mass spectrometers, most current research has focused on the design of a single stand-alone miniaturized mass spectrometer. Individual components of the mass spectrometer has been miniaturized for enhancing the mass spectrometer analysis capability (Liu et al. 2000, Zhang et al. 1999). A miniaturized mass spectrometry system using multiple analyzers (up to 10) in parallel has been reported (Badman and Cooks 2000). However, the mass spectrometer of Badman and Cook was designed to measure only single samples rather than multiple samples in parallel. They also noted that the miniaturization of the ion trap limited the capability of the mass spectrometer to scan wide mass ranges. Since the approach disclosed herein focuses on detecting four small stable mass tags (the mass range is less than 300 daltons), multiple miniaturized APCI mass spectrometers are easily constructed and assembled into a single unit for parallel analysis of the mass tags for DNA sequencing analysis.

Figure 24:
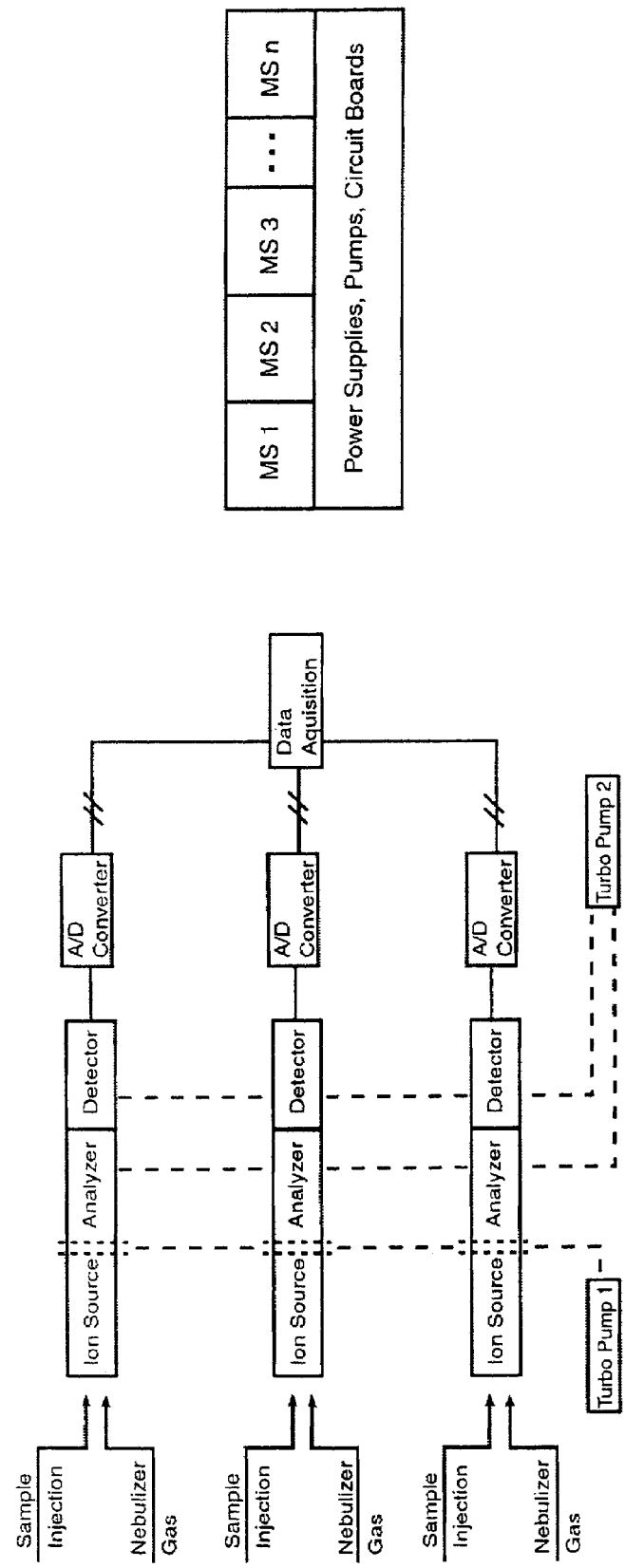
FIG. 24: Parallel mass spectrometry system for DNA sequencing. Example shows three mass spectrometers in parallel. Samples are injected into the ion source where they are mixed with a nebulizer gas and ionized. A turbo pump is used to continuously sweep away free radicals, neutral compounds and other undesirable elements coming from the ion source. A second turbo pump is used to generate a continuous vacuum in all three analyzers and detectors simultaneously. The acquired signal is then converted to a digital signal by the A/D converter. All three signals are then sent to the data acquisition processor to convert the signal to identify the mass tag in the injected sample and thus identify the nucleotide sequence.

A complete parallel mass spectrometry system includes multiple APCI sources interfaced with multiple analyzers, coupled with appropriate electronics and power supply configuration. A mass spectrometry system with parallel detection capability will overcome the throughput bottleneck issue for application in DNA analysis. A parallel system containing multiple mass spectrometers in a single device is illustrated in FIGS. 23 and 24. The examples in the figures show a system with three mass spectrometers in parallel. Higher throughput is obtained using a greater number of in parallel mass spectrometers.

As illustrated in FIG. 24, the three miniature mass spectrometers are contained in one device with two turbo-pumps. Samples are injected into the ion source where they are mixed with a nebulizer gas and ionized. One turbo pump is used as a differential pumping system to continuously sweep away free radicals, neutral compounds and other undesirable elements coming from the ion source at the orifice between the ion source and the analyzer. The second turbo pump is used to generate a continuous vacuum in all three analyzers and detectors simultaneously. Since the corona discharge mode and scanning mode of mass spectrometers are the same for each miniaturized mass spectrometer, one power supply for each analyzer and the ionization source can provide the necessary power for all three instruments. One power supply for each of the three independent detectors is used for spectrum collection. The data obtained are transferred to three independent A/D converters and processed by the data system simultaneously to identify the mass tag in the injected sample and thus identify the nucleotide. Despite containing three mass spectrometers, the entire device is able to fit on a laboratory bench top.

9. Validate the Complete Sequencing by Synthesis System By Sequencing P53 Genes

The tumor suppressor gene p53 can be used as a model system to validate the DNA sequencing system. The p53 gene is one of the most frequently mutated genes in human cancer (O'Connor et al. 1997). First, a base pair DNA template (shown below) is synthesized containing an azido group at the 5' end and a portion of the sequences from exon 7 and exon 8 of the p53 gene:

```
5'-N₃-TTCCTGCATGGGCGGCATGAACCCGAGGCCCATCCTCACCATCATCAC    (SEQ ID NO: 2)
ACTGGAAGACTCCAGTGGTAATCTACTGGGACGGAACAGCTTTGAGGTGCATT-3'.
```

This template is chosen to explore the use of the sequencing system for the detection of clustered hot spot single base mutations. The potentially mutated bases are underlined (A, G, C and T) in the synthetic template. The synthetic template is immobilized on a sequencing chip or glass channels, then the loop primer is ligated to the immobilized template as described in FIG. 6, and then the steps in FIG. 2 are followed for sequencing evaluation. DNA templates generated by PCR can be used to further validate the DNA sequencing system. The sequencing templates can be generated by PCR using flanking primers (one of the pair is labeled with an azido group at the 5'end) in the intron region located at each p53 exon boundary from a pool of genomic DNA (Boehringer, Indianapolis, Ind.) as described by Fu et al. (1998) and then immobilized on the DNA chip for sequencing evaluation.

RERERENCES

Antao V P, Lai S Y, Tinoco I Jr. (1991) A thermodynamic study of unusually stable RNA and DNA hairpins. *Nucleic Acids Res.* 19: 5901-5905.

Axelrod V D, Vartikyan R M, Aivazashvili V A, Beabealashvili R S. (1978) Specific termination of RNA polymerase synthesis as a method of RNA and DNA sequencing. *Nucleic Acids Res.* 5(10): 3549-3563.

Badman E R and Cooks R G. (2000) Cylindrical Ion Trap Array with Mass Selection by Variation in Trap Dimensions *Anal. Chem.* 72(20):5079-5086.

Badman E R and Cooks R G. (2000) A Parallel Miniature Cylindrical Ion Trap Array. *Anal. Chem.* 72(14):3291-3297.

Bowling J M, Bruner K L, Cmarik J L, Tibbetts C. (1991) Neighboring nucleotide interactions during DNA sequencing gel electrophoresis. *Nucleic Acids Res.* 19: 3089-3097.

Burgess K, Jacutin S E, Lim D, Shitangkoon A. (1997) An approach to photolabile, fluorescent protecting groups. *J. Org. Chem.* 62(15): 5165-5168.

Canard B, Cardona B, Sarfati R S. (1995) Catalytic editing properties of DNA polymerases. *Proc. Natl. Acad. Sci. USA* 92: 10859-10863.

Caruthers M H. (1985) Gene synthesis machines: DNA chemistry and its uses. *Science* 230: 281-285.

Chee M, Yang R, Hubbell E, Berno, A, Huang, X C., Stern D, Winkler, J, Lockhart D J, Morris M S, Fodor, S P. (1996) Accessing genetic information with high-density DNA arrays. *Science.* 274: 610-614.

Cheeseman P C. Method For Sequencing Polynucleotides, U.S. Pat. No. 5,302,509, issued Apr. 12, 1994.

Dizidic I, Carrol, D I, Stillwell, R N, and Horning, M G. (1975) Atmospheric pressure ionization (API) mass spectrometry: formation of phenoxide ions from chlorinated aromatic compounds *Anal. Chem.,* 47:1308-1312.

Fu D J, Tang K, Braun A, Reuter D, Darnhofer-Demar B, Little D P, O'Donnell M J, Cantor C R, Koster H. (1998) Sequencing exons 5 to 8 of the p53 gene by MALDI-TOF mass spectrometry. *Nat Biotechnol.* 16: 381-384.

Fuji K, Nakano S, Fujita E. (1975) An improved method for methoxymethylation of alcohols under mild acidic conditions. *Synthesis* 276-277.

Hobbs F W Jr, Cocuzza A J. Alkynylamino-Nucleotides. U.S. Pat. No. 5,047,519, issued Sep. 10, 1991.

Hung S C; Ju J; Mathies R A; Glazer A N. (1996) Cyanine dyes with high absorption cross section as donor chromophores in energy transfer primers. *Anal Biochem.* 243(1): 15-27.

Hyman E D, (1988) A new method of sequencing DNA. *Analytical Biochemistry* 174: 423-436.

Ireland R E, Varney M D (1986) Approach to the total synthesis of chlorothricolide-synthesis of (+/-)-19.20-dihydro-24-O-methylchlorothricolide, methyl-ester, ethyl carbonate. *J. Org. Chem.* 51: 635-648.

Ju J, Glazer A N, Mathies R A. (1996) Cassette labeling for facile construction of energy transfer fluorescent primers. *Nucleic Acids Res.* 24: 1144-1148.

Ju J, Ruan C, Fuller C W, Glazer A N Mathies R A. (1995) Energy transfer fluorescent dye-labeled primers for DNA sequencing and analysis. *Proc. Natl. Acad. Sci. USA* 92: 4347-4351.

Kamal A, Laxman E, Rao N V. (1999) A mild and rapid regeneration of alcohols from their allylic ethers by chlorotrimethylsilane/sodium iodide. *Tetrahedron letters* 40: 371-372.

Kheterpal I, Scherer J, Clark S M, Radhakrishnan A, Ju J, Ginther C L, Sensabaugh G F, Mathies R A. (1996) DNA Sequencing Using a Four-Color Confocal Fluorescence Capillary Array Scanner. *Electrophoresis.* 17: 1852-1859.

Khoukhi N, Vaultier M, Carrie R. (1987) Synthesis and reactivity of methyl-azido butyrates and ethyl-azido valerates and of the corresponding acid chlorides as useful reagents for the aminoalkylation. *Tetrahedron* 43: 1811-1822.

Lee L G, Connell C R, Woo S L, Cheng R D, Mcardle B F, Fuller C W, Halloran N D, Wilson R K. (1992) DNA sequencing with dye-labeled terminators and T7 DNA -polymerase-effect of dyes and dNTPs on incorporation of dye-terminators and probability analysis of termination fragments. *Nucleic Acids Res.* 20: 2471-2483.

Lee L G, Spurgeon S L, Heiner C R, Benson S C, Rosenblum B B, Menchen S M, Graham R J, Constantinescu A, upadhya K G, Cassel J M, (1997) New energy transfer dyes for DNA sequencing. *Nucleic Acids Res.* 25: 2816-2822.

Liu H. H., Felton C., Xue Q. F., Zhang B., Jedrzejewski P., Karger B. L. and Foret F. (2000) Development of multichannel Devices with an Array of Electrospray tips for high-throughput mass spectrometry. *Anal. Chem.* 72:3303-3310.

Metzker M L, Raghavachari R, Richards S, Jacutin S E, Civitello A, Burgess K, Gibbs R A. (1994) Termination of DNA synthesis by novel 3'-modified-deoxyribonucleoside 5'-triphosphates. *Nucleic Acids Res.* 22: 4259-4267.

O'Connor P M, Jackman J, Bae I, Myers T G, Fan S, Mutoh M, Scudiero D A, Monks A, Sausville E A, Weinstein J N, Friend S, Fornace A J Jr, Kohn K W. (1997) Characterization of the p53 tumor suppressor pathway in cell lines of the National Cancer Institute anticancer drug screen and correlations with the growth-inhibitory potency of 123 anticancer agents. *Cancer Res.* 57: 4285-4300.

Olejnik J, Ludemann H C, Krzymanska-Olejnik E, Berkenkamp S, Hillenkamp F, Rothschild K J. (1999) Photocleavable peptide-DNA conjugates: synthesis and applications to DNA analysis using MALDI-MS. *Nucleic Acids Res.* 27: 4626-4631.

Olejnik J, Sonar S, Krzymanska-Olejnik E, Rothschild K J. (1995) Photocleavable biotin derivatives: a versatile approach for the isolation of biomolecules. *Proc. Natl. Acad. Sci. USA.* 92: 7590-7594.

Pelletier H, Sawaya M R, Kumar A, Wilson S H, Kraut J. (1994) Structures of ternary complexes of rat DNA polymerase β, a DNA template-primer, and ddCTP. *Science* 264: 1891-1903.

Pennisi E. (2000) DOE Team Sequences Three Chromosomes. *Science* 288: 417-419.

Pillai V N R. (1980) Photoremovable Protecting Groups in Organic Synthesis. *Synthesis* 1-62.

Prober J M, Trainor G L, Dam R J, Hobbs F W, Robertson C W, Zagursky R J, Cocuzza A J, Jensen M A, Baumeister K. (1987) A system for rapid DNA sequencing with fluorescent chain-terminating dideoxynucleotides. *Science* 238: 336-341.

Rollaf F. (1982) Sodium-borohydride reactions under phase-transfer conditions—reduction of azides to amines. *J. Org. Chem.* 47: 4327-4329.

Ronaghi M, Uhlen M, Nyren P. (1998) A sequencing Method based on real-time pyrophosphate. *Science* 281: 364-365.

Rosenblum B B, Lee L G, Spurgeon S L, Khan S H, Menchen S M, Heiner C R, Chen S M. (1997) New dye-labeled terminators for improved DNA sequencing patterns. *Nucleic Acids Res.* 25: 4500-4504.

Roses A. (2000) Pharmacogenetics and the practice of medicie. *Nature.* 405: 857-865.

Salas-Solano O, Carrilho E, Kotler L, Miller A W, Goetzinger. W, Sosic Z, Karger B L, (1998) Routine DNA sequencing of 1000 bases in less than one hour by capillary electrophoresis with replaceable linear polyacrylamide solutions. *Anal. Chem.* 70: 3996-4003.

Saxon E and Bertozzi C R (2000) Cell surface engineering by a modified Staudinger reaction. *Science* 287: 2007-2010.

Schena M, Shalon D, Davis, R. Brown P. O. (1995) Quantitative monitoring of gene expression patterns with a cDNA microarray. *Science* 270: 467-470.

Simpson P C, Adam D R, Woolley T, Thorsen T, Johnston R, Sensabaugh G F, and Mathies R A. (1998) High-throughput genetic analysis using microfabricated 96-sample capillary array electrophoresis microplates. *Proc. Natl. Acad. Sci. U. S. A.* 95:2256-2261.

Smith L M, Sanders J Z, Kaiser R J, Hughes P, Dodd C, Connell C R, Heiner C, Kent SBH, Hood L E. (1986) Fluorescence detection in automated DNA sequencing analysis. *Nature* 321: 674-679.

Tabor S, Richardson C. C. (1987) DNA sequence analysis with a modified bacteriophage T7 DNA polymerase. *Proc. Natl. Acad. Sci. U.S.A.* 84: 4767-4771.

Tabor S. & Richardson, C C. (1995) A single residue in DNA polymerases of the *Escherichia coli* DNA polymerase I family is critical for distinguishing between deoxy- and dideoxyribonucleotides. *Proc. Natl. Acad. Sci. U.S.A.* 92: 6339-6343.

Turro N J. (1991) Modern Molecular Photochemistry; University Science Books, Mill Valley, Calif.

Velculescu V E, Zhang, I, Vogelstein, B. and Kinzler K W (1995) Serial Analysis of Gene Expression. *Science* 270: 484-487.

Welch M B, Burgess K, (1999) Synthesis of fluorescent, photolabile 3'-O-protected nucleoside triphosphates for the base addition sequencing scheme. *Nucleosides and Nucleotides* 18:197-201.

Woolley A T, Mathies R A. (1994) Ultra-high-speed DNA fragment separations using microfabricated capillary array electrophoresis chips. *Proc. Natl. Acad. Sci. USA.* 91: 11348-11352.

Woolley A T, Sensabaugh G F and Mathies R A. (1997) High-Speed DNA Genotyping Using Microfabricated Capillary Array Electrophoresis Chips, *Anal. Chem.* 69(11);2181-2186.

Yamakawa H, Ohara O. (1997) A DNA cycle sequencing reaction that minimizes compressions on automated fluorescent sequencers. *Nucleic. Acids. Res.* 25: 1311-1312.

Zhang X H, Chiang V L, (1996) Single-stranded DNA ligation by T4 RNA ligase for PCR cloning of 5'-noncoding fragments and coding sequence of a specific gene. *Nucleic Acids Res.* 24: 990-991.

Zhang B., Liu H. Karger B L. Foret F. (1999) Microfabricated devices for capillary electrophoresis-electrospray mass spectrometry. *Anal. Chem.* 71:3258-3264.

Zhu Z, Chao J, Yu H, Waggoner A S. (1994) Directly labeled DNA probes using fluorescent nucleotides with different length linkers. *Nucleic Acids Res.* 22: 3418-3422.

What is claimed is:

1. A nucleotide analogue which comprises:

(a) a base which is an adenine, an analogue of adenine, a cytosine, an analogue of cytosine, a guanine, an analogue of guanine, a thymine, an analogue of thymine, a uracil, or an analogue of uracil;

(b) a unique label attached through a cleavable linker to the base or to the analogue of the base;

(c) a deoxyribose;

(d) a —OR group at a 3'-position of the deoxyribose, wherein R is —CH$_2$OCH$_3$ or —CH$_2$CH=CH$_2$; and (e) a triphosphate group.

2. The nucleotide analogue of claim 1, wherein the unique label is a fluorescent moiety or a fluorescent semiconductor crystal.

3. The nucleotide analogue of claim 2, wherein the fluorescent moiety is 5-carboxyfluorescein, 6-carboxyrhodamine-6G, N,N,N',N'-tetramethyl-6-carboxyrhodamine, or 6-carboxy-X-rhodamine.

4. The nucleotide analogue of claim 1, wherein the unique label is a fluorescence energy transfer tag which comprises an energy transfer donor and an energy transfer acceptor.

5. The nucleotide analogue of claim 4, wherein the energy transfer donor is 5-carboxyfluorescein or cyanine, and wherein the energy transfer acceptor is selected from the group consisting of dichlorocarboxyfluorescein, dichloro-6-carboxyrhodamine-6G, dichloro-N,N,N',N'-tetramethyl-6-carboxyrhodamine, and dichloro-6-carboxy-X-rhodamine.

6. The nucleotide analogue of claim 1, wherein the unique label is a mass tag that can be detected and differentiated by a mass spectrometer.

7. The nucleotide analogue of claim 6, wherein the mass tag is a 2-nitro-α-methyl-benzyl group, a 2-nitro-α-methyl-3-fluorobenzyl group, a 2-nitro-α-methyl-3,4-difluorobenzyl group, or a 2-nitro-α-methyl-3,4-dimethoxybenzyl group.

8. The nucleotide analogue of claim 1, wherein the unique label is attached through a cleavable linker to a 5-position of cytosine or thymine or to a 7-position of deaza-adenine or deaza-guanine.

9. The nucleotide analogue of claim 1, wherein the cleavable linker between the unique label and the nucleotide analogue is cleavable by one or more of a physical means, a chemical means, a physical chemical means, heat, or light.

10. The nucleotide analogue of claim 9, wherein the cleavable linker is a photocleavable linker which comprises a 2-nitrobenzyl moiety.

11. The nucleotide analogue of claim 1, wherein the nucleotide analogue has the structure:

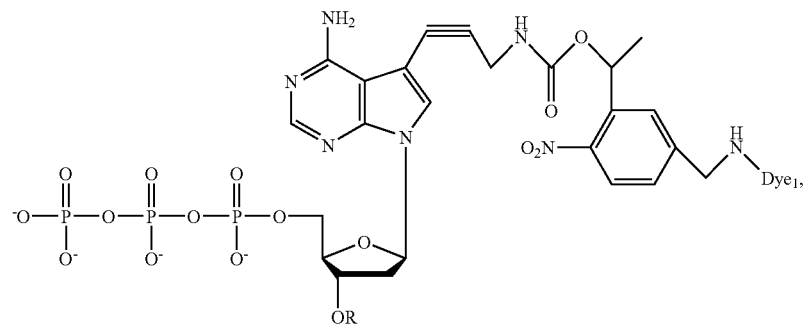
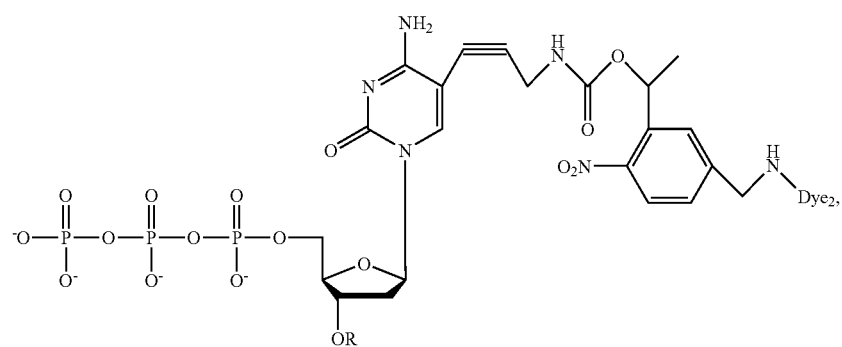
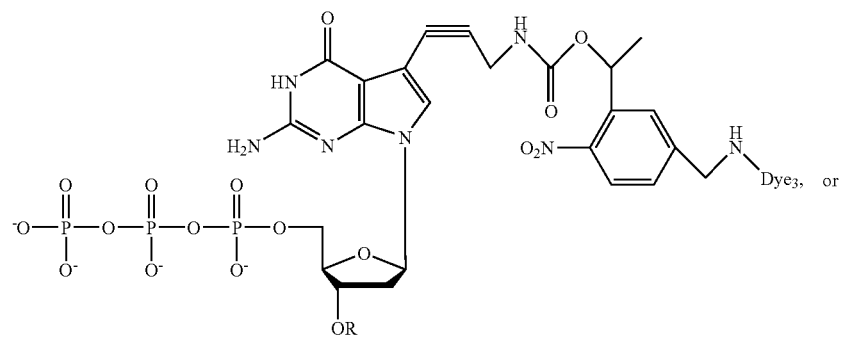
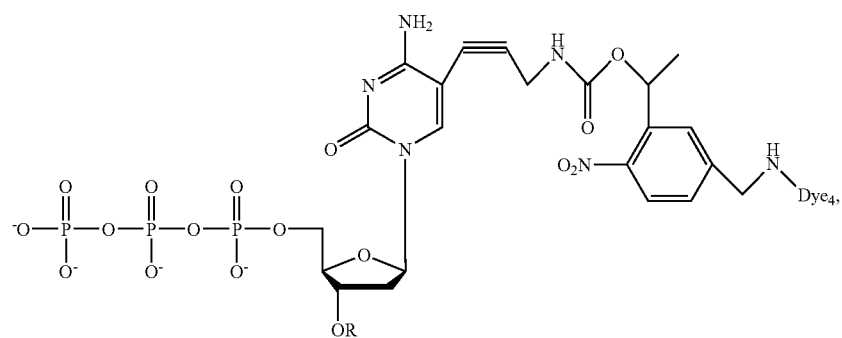

wherein Dye1, Dye2, Dye3, and Dye4 are four different dye labels; and wherein R is —CH$_2$OCH$_3$ or —CH$_2$CH=CH$_2$.
12. The nucleotide analogue of claim 11, wherein the nucleotide analogue has the structure:
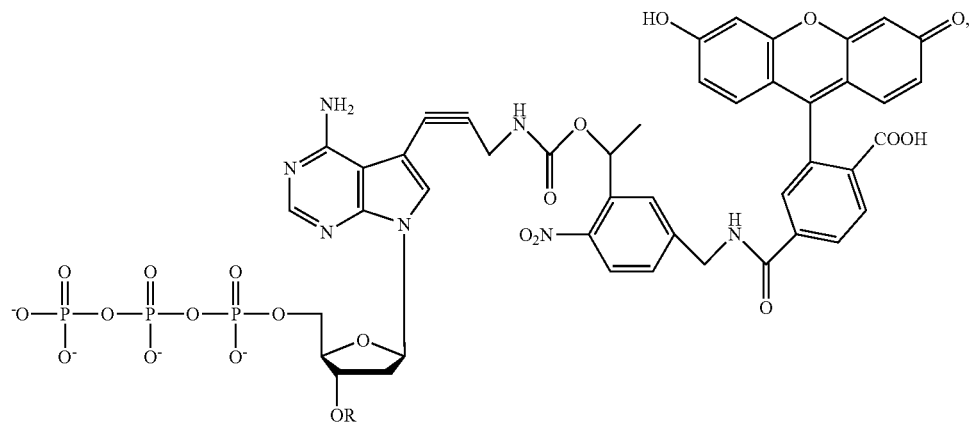
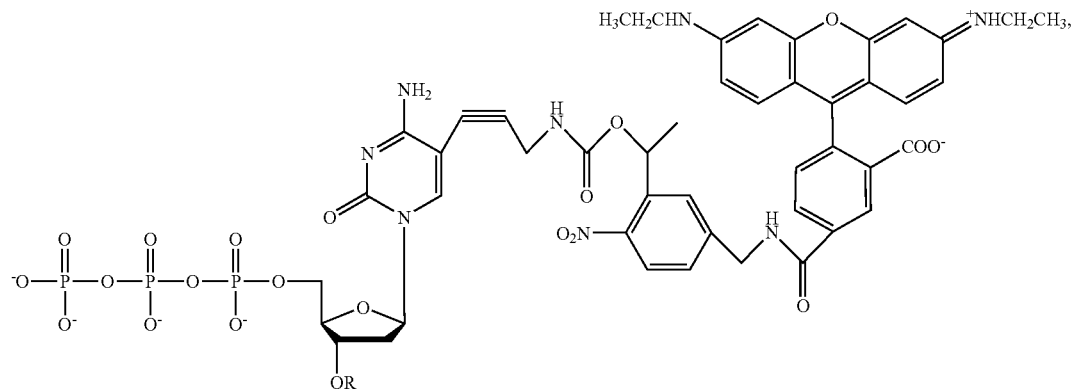
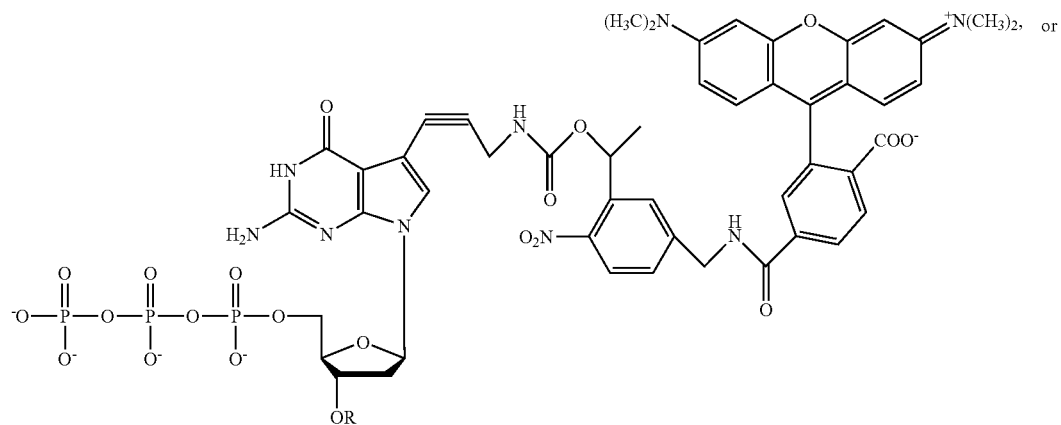

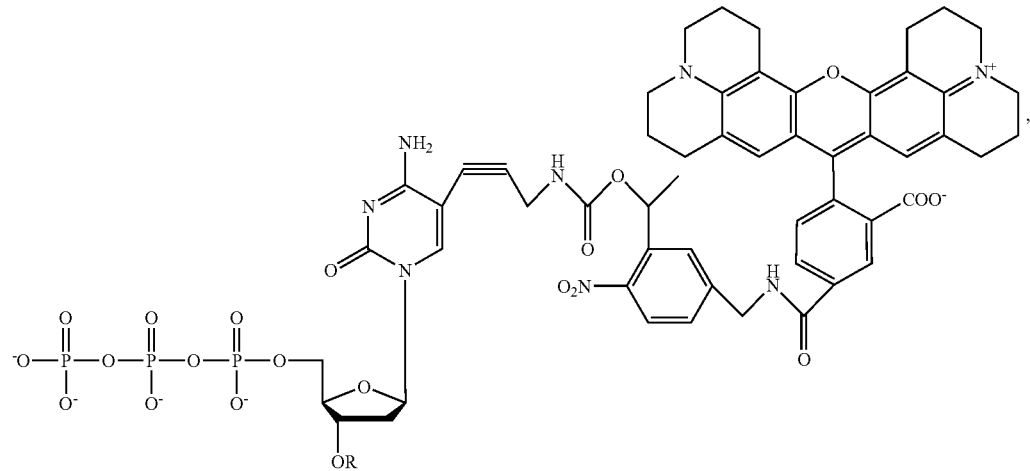
wherein R is —CH$_2$OCH$_3$ or —CH$_2$CH=CH$_2$.
13. The nucleotide analogue of claim 1, wherein the nucleotide analogue has the structure:
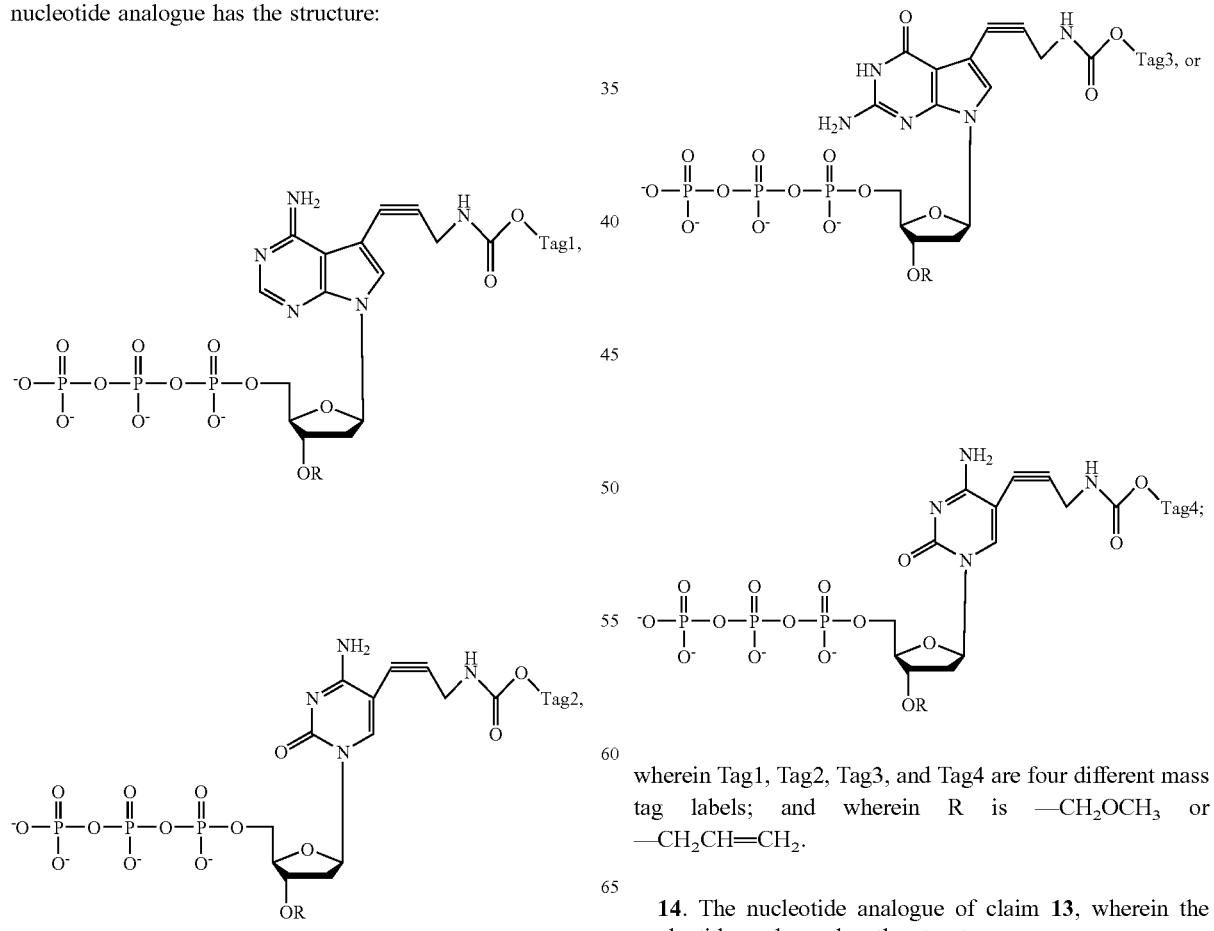
wherein Tag1, Tag2, Tag3, and Tag4 are four different mass tag labels; and wherein R is —CH$_2$OCH$_3$ or —CH$_2$CH=CH$_2$.
14. The nucleotide analogue of claim 13, wherein the nucleotide analogue has the structure:

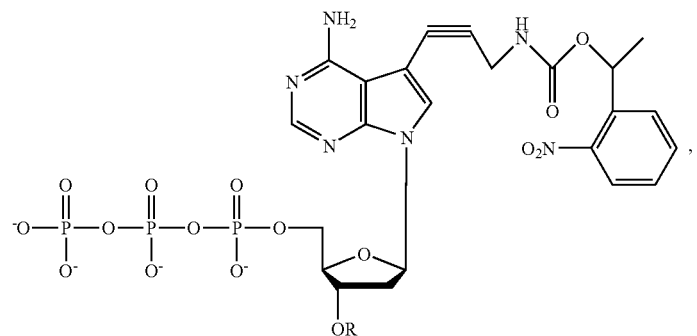
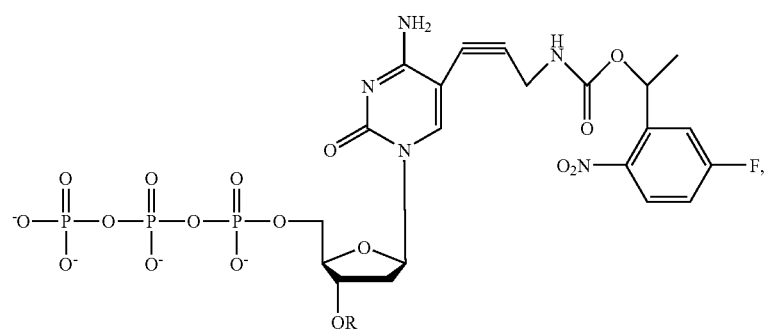
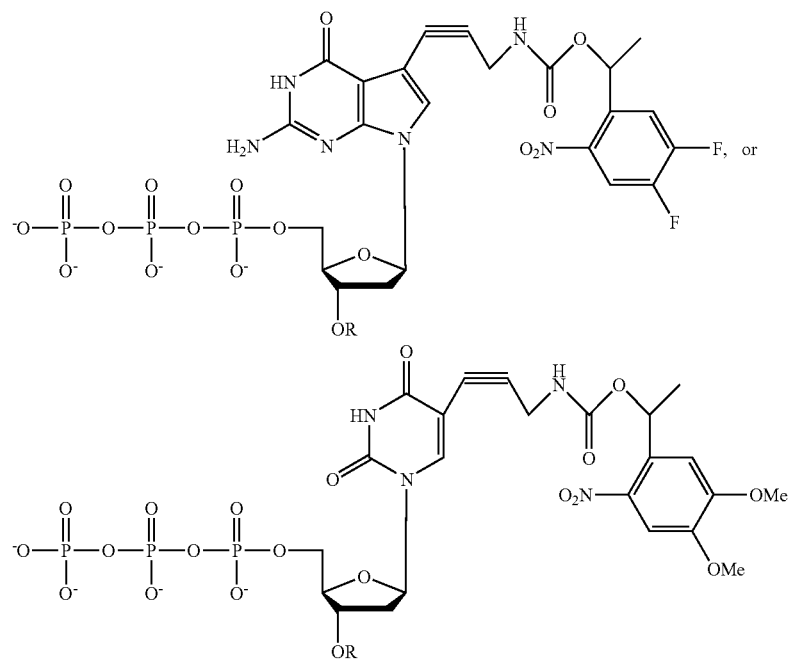
wherein R is —CH$_2$OCH$_3$ or —CH$_2$CH═CH$_2$.

15. A nucleotide analogue which comprises:
(a) a base which is an adenine, an analogue of adenine, a cytosine, an analogue of cytosine, a guanine, an analogue of guanine, a thymine, an analogue of thymine, a uracil, or analogue of uracil;
(b) a unique label attached through a cleavable linker to the base or to the analogue of the base;
(c) a deoxyribose;
(d) a —OR group at a 3'-position of the deoxyribose, wherein R is a cleavable chemical group; and
(e) a triphosphate group,
wherein the nucleotide analogue has the structure:

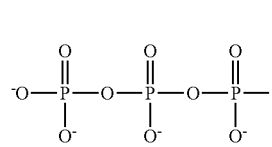
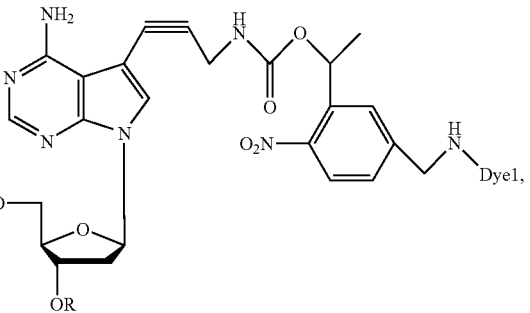

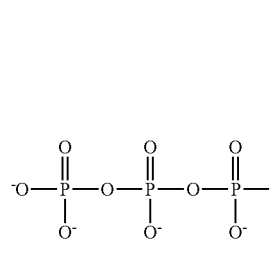
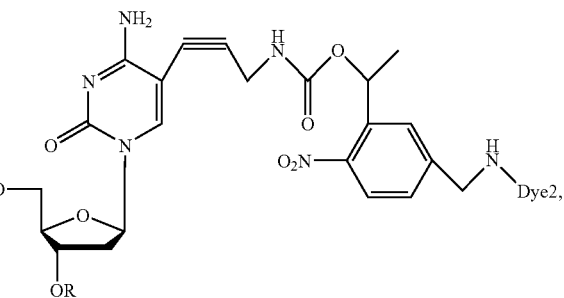

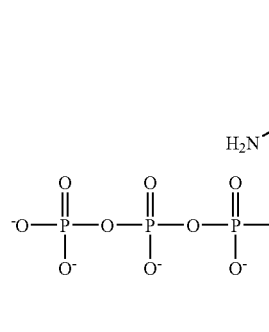
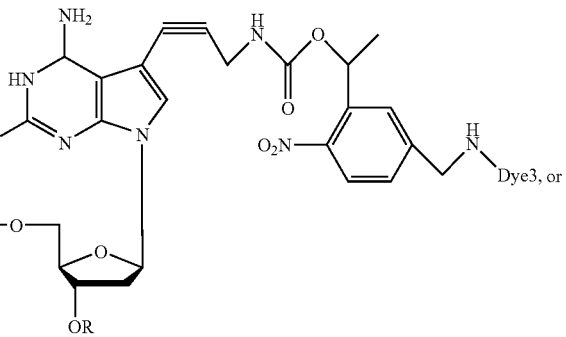

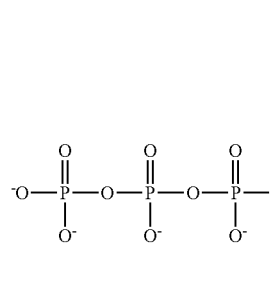
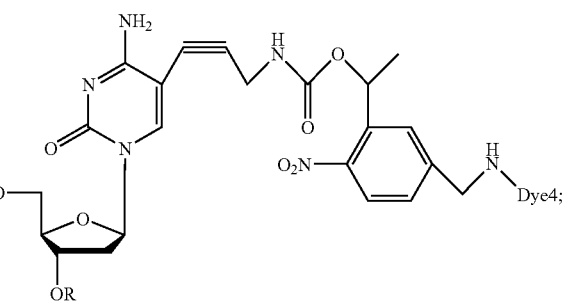

wherein Dye1, Dye2, Dye3, and Dye4 are four different dye labels.

16. The nucleotide analogue of claim 15, wherein the cleavable chemical group is cleavable by one or more of a physical means, a chemical means, a physical chemical means, heat, or light.

17. The nucleotide analogue of claim 15, wherein the dye is 5-carboxyfluorescein, 6-carboxyrhodamine-6G, N,N,N', N'-tetramethyl-6-carboxyrhodamine, or 6-carboxy-X-rhodamine.

18. The nucleotide analogue of claim 15, wherein R is —$CH_2OCH_3$ or —$CH_2CH$=$CH_2$.

* * * * *

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: template

<400> SEQUENCE: 1
acgtacgacg t                                                              11

<210> SEQ ID NO 2
<211> LENGTH: 101
<212> TYPE: DNA
<213> ORGANISM: Artificial Sequence
<220> FEATURE:
<223> OTHER INFORMATION: Description of Artificial Sequence: template

<400> SEQUENCE: 2
ttcctgcatg ggcggcatga acccgaggcc catcctcacc atcatcacac tggaagactc        60
cagtggtaat ctactgggac ggaacagctt tgaggtgcat t                           101
```